(12) United States Patent
Hogg et al.

(10) Patent No.: US 10,828,275 B2
(45) Date of Patent: Nov. 10, 2020

(54) SELECTIVE TARGETING OF PROCOAGULANT PLATELETS

(71) Applicant: NewSouth Innovations Pty Limited, New South Wales (AU)

(72) Inventors: Philip John Hogg, Malabar (AU); Vivien M. Y. Chen, Mosman (AU); Leonardo Pasalic, Glenfield (AU); Vu Minh Hua, Zetland (AU)

(73) Assignee: NewSouth Innovations Pty Limited, New South Wales (AU)

( * ) Notice: Subject to any disclaimer, the term of this patent is extended or adjusted under 35 U.S.C. 154(b) by 0 days.

(21) Appl. No.: 15/521,435

(22) PCT Filed: Oct. 26, 2015

(86) PCT No.: PCT/AU2015/000638
§ 371 (c)(1),
(2) Date: Apr. 24, 2017

(87) PCT Pub. No.: WO2016/061618
PCT Pub. Date: Apr. 28, 2016

(65) Prior Publication Data
US 2017/0326096 A1  Nov. 16, 2017

(30) Foreign Application Priority Data
Oct. 24, 2014 (AU) ................ 2014904259

(51) Int. Cl.
| | | |
|---|---|---|
| A61K 31/285 | (2006.01) | |
| G01N 33/86 | (2006.01) | |
| A61K 31/00 | (2006.01) | |
| C07F 9/66 | (2006.01) | |
| C07F 9/76 | (2006.01) | |
| C07F 9/78 | (2006.01) | |

(52) U.S. Cl.
CPC ............ *A61K 31/285* (2013.01); *A61K 31/00* (2013.01); *C07F 9/66* (2013.01); *C07F 9/76* (2013.01); *C07F 9/78* (2013.01); *G01N 33/86* (2013.01); *G01N 2500/04* (2013.01)

(58) Field of Classification Search
None
See application file for complete search history.

(56) References Cited

U.S. PATENT DOCUMENTS
| | | |
|---|---|---|
| 2007/0003799 A1 | 2/2007 | Hogg |
| 2007/0037995 A1 | 2/2007 | Hogg et al. |
| 2009/0031117 A1 | 12/2009 | Hogg |
| 2009/0311179 A1 | 12/2009 | Hogg |

FOREIGN PATENT DOCUMENTS
| | | |
|---|---|---|
| WO | 03/003011 A1 | 1/2003 |
| WO | 2003/003011 A1 | 1/2003 |

OTHER PUBLICATIONS

Jackson et al (Blood 116:2011-2018, 2010) (Year: 2010).*
Xie et al (Cell Death and Disease 4:e473, 2013) (Year: 2013).*
Fager et al (Arterioscler Thromb Vasc Biol 30:2400-2407, 2010) (Year: 2010).*
Roest et al (Transfus Med Hemother 40:117-125, 2013) (Year: 2013).*
Tait et al (Blood Cells, Molecules, and Diseases 25:271-278, 1999) (Year: 1999).*
Chen (Final Report: Kanematsu 2011) (Year: 2011).*
Hua et al., "Procoagulant role of necrotic platelets demonstrated using novel platelet necrosis marker", Blood, 2013, 122(21), 5 pages.
Hua et al., "Procoagulant platelets are undergoing cyclophilin D mediated necrosis with differential involvement in occlusive vs. non-occlusive models of thrombosis", Journal of Thrombosis and Haemostasis, 2015, vol. 13, Supp. SUPPL. 2, p. 165.
Pasalic et al., "A novel assay demonstrates procoagulant platelets are increased in patient undergoing coronary angiography with differential effects by anti-platelet and anticoagulant therapy", Journal of Thrombosis and Haemostasis, 2015, vol. 13, Supp. SUPPL. 2, 290-291.
Pasalic et al., "Characterisation of procoagulant platelets in whole blood using a novel cell death marker". Journal of Thrombosis and Haemostasis, 2015, vol. 13, Supp. SUPPL. 2, p. 657.
Pasalic et al., "A novel assay demonstrates procoagulant platelets are increased in patient undergoing coronary angiography with differential effects by anti-platelet and anti-coagulant therapy", Haematologica, 2015, vol. 100, Supp. SUPPL. 1, pp. 144-145.
Pasalic et al., "Characterization of procoagulant platelets in whole blood using a novel cell death marker", Haematologica, 2015, vol. 100, Supp. SUPPL. 1, 145-146.
Prodan et al., "Higher coated-platelet levels are associated with stroke recurrence following nonlacunar brain infarction", Journal of Cerebral Blood Flow & Metabolism, 2013, vol. 33, 287-292.
Kirkpatrick et al., "Coated-platelets improve prediction of stroke and transient ischaemic attack in asymptomatic internal carotid artery stenosis", Stroke, 2014, vol. 45, 2995-3001.
Grundler et al., "Platelet mitochondrial membrane depolarization reflects disease severity in patients with sepsis and correlates with clinical outcome", Critical Care, 2014, 18(R31), 1-9.
Schoenwaelder et al., "Two distinct pathways regulate platelet phosphatidylserine exposure and procoagulant function", Blood, 2009, 114(3), 663-666.
Jobe et al., "Critical role for the mitochondrial permeability transition pore and cyclophilin D in platelet activation and thrombosis", Blood, 2008, 111(3), 1257-1265.
Bouchard et al., "Measurement of procoagulant platelet subpopulations in whole blood: development of an assay for population-based studies", Thromb. Res., 2011, 127(1), 62-64.

(Continued)

*Primary Examiner* — Craig D Ricci
(74) *Attorney, Agent, or Firm* — McDonneell Boehnen Hulbert & Berghoff LLP

(57) ABSTRACT

The invention relates to a process for identifying procoagulant platelets both in vitro and in vivo, and the identification of compounds which selectively inhibit formation of procoagulant platelets.

7 Claims, 20 Drawing Sheets

(56) References Cited

OTHER PUBLICATIONS

Heemskerk et al., "Collagen but not fibrinogen surfaces induce bleb formation, exposure of phosphatidylserine, and procoagulant activity of adherent platelets: evidence for regulation by protein tyrosine kinase-dependent Ca2+ responses", Blood 90, 1997, 2615-2625.

Park et al., "Noninvasive imaging of cell death using an hsp90 ligand", Journal of the American Chemical Society, 2011, vol. 133, 2832-2835.

Park et al., "Optical Imaging of Treatment-Related Tumor Cell Death Using a Heat Shock Protein-90 Alkylator", Molecular Pharmaceutics, 2013, vol. 10, 3882-3891.

Xie et al., "Optical imaging of cell death in traumatic brain injury using a heat shock protein-90 alkylator", Cell Death & Disease 2013, 4(e473), 1-8.

Bevers et al., "Generation of prothrombin-converting activity and the exposure of phosphatidylserine at the outer surface of platelets", Eur. J. Biochem., 1982, 122(2), 429-436.

Fager et al., "Properties of procoagulant platelets: defining and characterizing the subpopulation binding a functional prothrombinase", Arteriosclerosis, Thrombosis, and Vascular Biology, 2010, 30(12), 2400-2407.

Dilda et al., "Optimization of the antitumor efficacy of a synthetic mitochondrial toxin by increasing the residence time in the cytosol", The Journal of Medicinal Chemistry, 2009, 52(20), 6209-6216.

Dilda et al., "Metabolism of the tumor angiogenesis inhibitor 4-(N-(S-Glutathionylacetyl)amino)phenylarsonous acid", The Journal of Biological Chemistry, 2008, 283(51), 35428-35434.

Hagenbuch, et al., "The superfamily of organic anion transporting polypeptides", Biochimica et Biophysica Acta, 2003, 1609(1), 1-18.

Niessen et al., "Human platelets express organic anion-transporting peptide 2B1, an uptake transporter for atorvastatin", Drug Metabolism and Disposition, 2009, 37(5), 1129-1137.

Kobayashi et al., "Involvement of human organic anion transporting polypeptide OATP-B (SLC21A9) in pH-dependent transport across intestinal apical membrane", The Journal of Pharmacology and Experimental Therapeutics, 2003, 306(2), 703-708.

Nakagawa et al., "Cyclophilin D-dependent mitochondrial permeability transition regulates some necrotic but not apoptotic cell death.", Nature, 2005, vol. 434, 652-658.

McCormack et al., "Role of calcium ions in regulation of mammalian intramitochondrial metabolism", Physiological Reviews., 1990, 70(2), 391-425.

Falati et al., "Real-time in vivo imaging of platelets, tissue factor and fibrin during arterial thrombus formation in the mouse", Nature Medicine, 2002, 8(10), 1175-1181.

Dubois et al., "Thrombin-initiated platelet activation in vivo is vWF independent during thrombus formation in a laser injury model", The Journal of Clinical Investigation, 2007, 117(4), 953-960.

Dubois et al., "Glycoprotein Vl-dependent and -independent pathways of thrombus formation in vivo", Blood, 2006, 107(10), 3902-3906.

Voronov et al., "Simulation of intrathrombus fluid and solute transport using in vivo clot structures with single platelet resolution", Annals of Biomedical Engineering, 2013, 41(6), 1297-1307.

Stalker et al., "Hierarchical organization in the hemostatic response and its relationship to the platelet-signaling network", Blood, 2013, 121(10), 1875-1885.

Dale et al., "Stimulated platelets use serotonin to enhance their retention of procoagulant proteins on the cell surface", Nature, 2002, 415(6868), 175-179.

Abaeva et al., "Procoagulant platelets form an alpha-granule protein-covered "cap" on their surface that promotes their attachment to aggregates", 2013, The Journal of Biological Chemistry, 288(41), 29621-29632.

Bratosin et al., "Novel fluorescence assay using calcein-AM for the determination of human erythrocyte viability and aging", Cyometry Part A, 2005, 66(1), 78-84.

Hemker et al., "Calibrated automated thrombin generation measurement in clotting plasma", Pathophysiology of Haemostasis and Thrombosis, 2003, 33(1), 4-15.

Schinzel et al., "Cyclophilin D is a component of mitochondrial permeability transition and mediates neuronal cell death after focal cerebral ischemia", Proc. Natl. Acad. Sci., 2005, 102(34), 12005-12010.

Tiedt et al.,. "Pf4-Cre transgenic mice allow the generation of lineage-restricted gene knockouts for studying megakaryocyte and platelet function in vivo", Blood, 2007, 109(4), 1503-1506.

Bolte et al., "A guided tour into subcellular colocalization analysis in light microscopy", Journal of Microscopy, 2006, 224(Pt 3), 213-232.

* cited by examiner

A

B

C

E

FeCl₃ injury orthogonal view

Platelets

F

FeCl₃ injury 3D reconstruction

Fibrin

Platelets/GSAO
Platelets/GSAO/fibrin

US 10,828,275 B2

SELECTIVE TARGETING OF PROCOAGULANT PLATELETS

This application is a US national phase of International Application No. PCT/AU2015/000638, filed Oct. 26, 2015, which claims priority to Australian Application No. 2014904259, filed Oct. 24, 2014.

FIELD

The present invention relates to a process for identifying procoagulant platelets in vitro or in vivo, and the identification of compounds which selectively inhibit formation of procoagulant platelets.

PRIORITY

The present application claims priority from Australian provisional patent application AU 2014904259, the entire contents of which are incorporated herein by cross-reference.

BACKGROUND

Hemostasis is the physiological response to vascular injury to control blood loss. Vascular injury initiates rapid activation and aggregation of platelets in the process of primary hemostasis, resulting in an unstable platelet plug. Secondary hemostasis involves activation of the plasma borne coagulation factors and is required to form a fibrin meshwork to stabilise the platelet plug. When this process occurs in excess, or at the wrong site, thrombosis occurs. Thrombosis is the pathological process of vascular occlusion by excess blood clot. It can occur in the arterial or venous systems, leading to clinical outcomes including myocardial infarction, stroke, deep venous thrombosis and as such, thrombosis remains the most common cause of death in industrialised nations.

Activated platelets have a dual role in hemostasis and thrombosis. They aggregate to form the platelet plug and also provide the surface for the assembly of the coagulation factors. A subset of activated platelets, which have been termed 'procoagulant platelets', have distinct properties including the ability to support thrombin generation (Jackson, 2011). There is evidence that disturbances in this subset of platelets may be correlated to clinical outcome. Patients with a higher level of procoagulant platelets following a large-artery stroke had a higher risk of stroke recurrence (Prodan et al., 2013). Similarly, procoagulant platelet levels appear to predict stroke or transient ischaemic attack (TIA) in patients with asymptomatic carotid artery stenosis (Kirkpatrick et al., 2014). Furthermore, in patients with sepsis, platelet mitochondrial membrane depolarization, which is a pre-requisite for formation of procoagulant subset of platelets, correlated with disease severity and disease outcome (Grundler et al., 2014).

Excess procoagulant activity can tip the balance from physiological hemostasis to pathological thrombosis which means that platelet procoagulant activity is a profoundly important concept. Elevated levels of 'coated' platelets, defined as platelets with high levels of retained procoagulant proteins, have been demonstrated in patients with ischaemic stroke and recurrent ischaemic stroke, while low levels correlate with haemorrhagic complications of stroke (Prodan et al., 2013). Identifying and understanding this subset is particularly important. It has been differentially proposed that the procoagulant 'coated' platelet is formed via activation of apoptosis pathways (Schoenwaelder et al., 2009), or necrosis pathways through cyclophilin D-dependent mitochondrial permeability transition pore formation (Jobe et al, 2008). Most studies concur that combination thrombin and collagen stimulation is required for maximal generation of the procoagulant phenotype.

The study of the physiological and pathological role of the procoagulant platelet in vivo, though, has been thwarted by the lack of a suitable marker. Traditionally, the procoagulant phenotype has been identified by classic morphology under phase contrast or differential interference contrast microscopy, and by measuring sustained calcium response using calcium-sensitive dyes (Bouchard et al., 2011; Heemskerk et al., 1997). While this is possible in specialised laboratories using high end microscopy, only superficial vascular beds can be studied. Use of annexin V or lactadherin to study phosphatidylserine-positive platelets is problematic since only a subset of platelets elaborating phosphatidylserine are procoagulant and the labeling probes are inhibitory to the process being studied in the doses required for in vivo imaging.

Accordingly, there is a need for a method of measuring procoagulant platelets which would be of broad utility for examining contribution of platelets and potential therapeutic interventions in coronary artery disease, stroke, venous thromboembolism, autoimmune vasculitis, sepsis and many other conditions characterized by arterial or venous thrombosis. Most existing methods are based on a washed platelet system or platelet rich plasma, which requires the time-consuming and labor-intensive isolation of platelets from whole blood, thereby limiting their utility in population-based studies.

The present invention provides a process for identifying the procoagulant platelets both in vitro and in vivo. Further, the present invention provides a process for selectively inhibiting the formation of procoagulant platelets.

SUMMARY

According to a first aspect of the invention there is provided a process for identifying procoagulant platelets, comprising contacting a platelet with a compound and determining whether the compound binds to the platelet, wherein the compound is an arsenoxide (or arsenoxide equivalent) compound.

According to a second aspect of the invention there is provided a process for identifying a patient at risk of developing a prothrombotic or thrombotic condition, comprising contacting a platelet from said patient with a compound and determining whether the compound binds to the platelet, wherein the compound is an arsenoxide (or arsenoxide equivalent) compound.

With reference to the first and second aspects of the invention, in one embodiment, contacting the platelet with the compound may occur in vivo or in vitro. In another embodiment, contacting the platelet with the compound may occur in whole blood. In another embodiment, contacting the platelet with the compound may occur within a human subject.

Also with reference to the first and second aspects of the invention, the process may further comprise determining the proportion of procoagulant platelets in a sample. The proportion of procoagulant platelets in a sample may be indicative of a prothrombotic or thrombotic condition. The prothrombotic or thrombotic conditions may include: infection, sepsis, systemic inflammatory response syndrome, multi organ failure, thrombotic thrombocytopenia purpura, haemolytic uraemia syndrome, vascularisation, renal failure, ischaemic repercussion injury, solid organ transplant rejection, cardiovascular disease, stroke, venous thromboembolism, autoimmune disorders, sickle cell disease, inflammatory bowel disease, acute lung injury, malignancy, myocardial infarction (primary and secondary), embolic stroke, ischaemic stroke, thrombotic stroke, deep vein thrombosis (DVT), thromboembolism, portal vein thrombosis, renal vein thrombosis, jugular vein thrombosis, Budd-Chiari syndrome, Paget-Schroetter disease, cerebral venous sinus thrombosis, arterial thrombosis or arterial embolis.

According to a third aspect of the invention there is provided a process for identifying a compound which inhibits formation of procoagulant platelets, wherein said process comprises contacting a sample comprising platelets with a compound and determining whether the compound inhibits formation of procoagulant platelets.

According to a fourth aspect of the invention there is provided a process for screening a plurality of compounds to identify a compound which selectively inhibits formation of procoagulant platelets, wherein said process comprises contacting a sample comprising platelets with the plurality of compounds, determining whether any of the compounds inhibit formation of procoagulant platelets, and if so, separately determining for each of the plurality of compounds whether the compound inhibits formation of procoagulant platelets.

With reference to the third and fourth aspects of the invention, in one embodiment, inhibition of formation of procoagulant platelets may occur by inhibiting the mitochondrial necrosis pathway. In another embodiment inhibition of formation of procoagulant platelets may be determined by comparing the proportion of procoagulant platelets before contacting the platelets with the compound with the proportion of procoagulant platelets after contacting the platelets with the compound. In a further embodiment, the proportion of procoagulant platelets may be determined by the process for identifying procoagulant platelets according to the first aspect.

With further reference to the first and second aspect of the invention, in one embodiment the trivalent arsenoxide compound may be a dithiol reactive compound.

In a further embodiment, the arsenoxide (or arsenoxide equivalent) compound may have the formula (I):

A-[(XBX')nB'—Y]p     (I)

wherein

A comprises at least one pendant group which may be substantially cell-membrane impermeable;

(XBX')nB' comprises a suitable linker group, where n is an integer selected from 0, 1, 2, 3, 4, 5, 6, 7, 8, 9, 10, 11, 12, 13, 14, 15, 16, 17, 18, 19 and 20;

Y comprises at least one arsenoxide or arsenoxide equivalent; and p is an integer selected from 1, 2, 3, 4, 5, 6, 7, 8, 9, and 10.

In one embodiment, the compound of formula (I) may have more than 6 carbon atoms.

The following features relate to Formula (I):

In one embodiment, A may be selected from the group consisting of natural, unnatural and synthetic amino acids, hydrophilic amines, peptides and polypeptides, including dipeptides, tripeptides, tetrapeptides, pentapeptides, sugar residues such as monosaccharides, disaccharides and oligosaccharides (including substituted variants), and thiol containing proteins, or a combination thereof. For example, A may be selected from the group consisting of glutathione, glucosamine, cysteinylglycine, cysteic acid, aspartic acid, glutamic acid, lysine, and arginine, wherein the sulfur atom of each sulfur containing compound may be optionally oxidised to form a sulfoxide or sulfone. In other embodiments, A may comprise a sugar residue, disaccharide or oligosaccharide residue such as, for example, glucose, fructose, mannose, xylose, lyxose, galactose, hexose, sucrose, sorbose, galactosyl-sucrose, sorbitol, mannitol, xylitol, etc. In other embodiments, A may be a hydrophilic amine such as a primary, secondary, or tertiary alkyl-, aryl- or aralkyl-amine, or a heterocyclic amine such as pyridine, pyrrole, imidazole etc.

Amino acids are known to those of skill in the art and are listed, for instance in standard reference texts, such as King and Stansfield, A Dictionary of Genetics, 4th Edition, Oxford University Press, 1990, the contents of which are incorporated herein by reference. For example, the amino acids may be α, β or γ amino acids. The present invention also includes the L- and D-forms of amino acids. Examples of amino acids include glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine and histidine.

In one embodiment, A may be selected from the group consisting of tri-acid ureas, peptides including dipeptides, tripeptides, tetrapeptides, and pentapeptides. For example, glutathione, Cys-Glu-Gly, Arg-Gly-Asp-Cys, Val-Thr-Cys-Gly, Gly-Gly-Cys, Lys-Glu-Gly, Arg-Gly-Asp-Lys, Val-Thr-Lys-Gly, Gly-Gly-Lys, Ser-Glu-Gly, Arg-Gly-Asp-Ser, Val-Thr-Ser-Gly, Gly-Gly-Ser, Asp-Glu-Gly, Arg-Gly-Asp-Asp, Val-Thr-Asp-Gly, Gly-Gly-Asp, Glu-Glu-Gly, Arg-Gly-Asp-Glu, Val-Thr-Glu-Gly, Gly-Gly-Glu, etc, pressinoic acid, small acid molecules such as 3-mercapto-1-propane-sulfonic acid, mercaptopropionic acid, mercapto succinic acid; small alcohols such as 1-thio-beta-D-glucose, 3-mercapto-1,2-propanediol; small amines, including for example, primary, secondary and tertiary alkyl-, aryl- and aralkyl substituted amines; and heteroaromatic compounds such as 5-mercapto-1-tetrazolacetic acid, 2-mercaptopyridine, and 2-aminopyridine.

In one embodiment, A is a tripeptide. For example, A may be glutathione and in one form the compound may be represented by Formula (II):

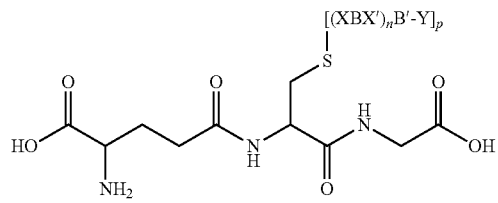

wherein (XBX')nB' comprises any suitable linker group, and Y comprises an arsenoxide or an arsenoxide equivalent.

In one embodiment, p is an integer selected from 1 to 5. For example, p may be 1, 2, 3, 4, or 5. In one embodiment p is 1 or 2. In another embodiment, p is 1.

In one embodiment, n is an integer from 0 to 15. For example, n may be 0, 1, 2, 3, 4, 5, 6, 7, 8, 9, 10, 11, 12, 13, 14, or 15. In one embodiment n is an integer selected from 0 to 10. In another embodiment n is an integer selected from 0 to 5, for example, n may be 0, 1, 2, 3, 4, or 5.

In one embodiment, X is selected from the group consisting of —NR, —S(O)—, —S(O)O—, —S(O)$_2$—, —S(O)$_2$O—, —C(O)—, —C(S)—, —C(O)O—, C(S)O—, —C(S)S—, —P(O)(R$_1$)—, and —P(O)(R$_1$)O—, or is absent;

B is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkenylene, C$_6$-C$_{12}$ arylene, heteroarylene and C$_2$-C$_{10}$ acyl;

X' is selected from the group consisting of —NR—, —O—, —S—, —Se—, —S—S—, S(O)—, —OS(O)—, OS(O)O—, —OS(O)$_2$, —OS(O)$_2$O—, —S(O)O—, —S(O)$_2$—, —S(O)$_2$O—, —OP(O)(R$_1$)—, —OP(O)(R$_1$)O—, —OP(O)(R$_1$)OP(O)(R$_1$)O—, —C(O)—, —C(S)—, —C(O)O—, C(S)O—, —C(S)S—, —P(O)(R$_1$)—, —P(O)(R$_1$)O—, and

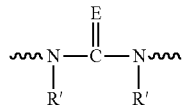

or is absent; wherein E is O, S, Se, NR or N(R)$_2$$^+$;

n is 0, 1 or 2; and

B' is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkenylene, C$_6$-C$_{12}$ arylene, and heteroarylene or is absent; and wherein each R is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, OR$_2$ and C$_2$-C$_{10}$ acyl;

R' is the same as R or two R' may be taken together with the nitrogen atoms to which they are attached to form a 5 or 6-membered saturated or unsaturated heterocyclic ring;

each R$_1$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, halo, OR$_2$ and N(R)$_2$;

each R$_2$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl and —C(O)R$_5$;

each R$_5$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, C$_1$-C$_{10}$ alkoxy, C$_3$-C$_{10}$ alkenyloxy, C$_3$-C$_{10}$ alkynyloxy, C$_3$-C$_{10}$ cycloalkyloxy, C$_5$-C$_{10}$ cycloalkenyloxy, C$_3$-C$_{10}$ heterocycloalkyloxy, C$_5$-C$_{10}$ heterocycloalkenyloxy, C$_6$-C$_{12}$ aryloxy, heteroaryloxy, C$_1$-C$_{10}$ alkylthio, C$_3$-C$_{10}$ alkenylthio, C$_3$-C$_{10}$ alkynylthio, C$_3$-C$_{10}$ cycloalkylthio, C$_5$-C$_{10}$ cycloalkenylthio, C$_3$-C$_{10}$ heterocycloalkylthio, C$_5$-C$_{10}$ heterocycloalkenylthio, C$_6$-C$_{12}$ arylthio, heteroarylthio, OH, SH and N(R)$_2$;

wherein for each instance that B and/or B' is arylene, the substituents directly attached to the respective arylene rings (including arsenoxide or arsenoxide equivalent) ray be at any available position, and for example, may be in a para-, meta- or ortho-relationship; and wherein each alkylene, alkenylene, alkynylene, cycloalkylene, cycloalkenylene, heterocycloalkylene, heterocycloalkenylene, arylene, heteroarylene and acyl may be independently substituted with hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, cyano, cyanate, isocyanate, OR)$_{2a}$, SR$_6$, nitro, arsenoxide, —S(O)R$_3$, —OS(O)R$_3$, —S(O)$_2$R$_3$, —OS(O)$_2$R$_3$, —P(O)R$_4$R$_4$, —OP(O)R$_4$R$_4$, —N(R")$_2$, —NRC(O)(CH$_2$)$_m$Q, —C(O)R$_5$;

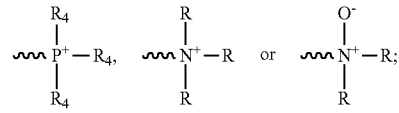

wherein R, R$_1$ and R$_5$ are as defined above; and

R$_{2a}$ is selected from the group consisting of hydrogen, C$_1$-C$_5$ alkyl, C$_2$-C$_5$ alkenyl, C$_2$-C$_5$ alkynyl, C$_3$-C$_{10}$ cycloalkyl, C$_5$-C$_{10}$ cycloalkenyl, C$_6$-C$_{12}$ aryl, —S(O)R$_3$, —S(O)$_2$R$_3$, —P(O)(R$_4$)$_2$, N(R)$_2$ and —C(O)R$_5$;

each R$_3$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, C$_1$-C$_{10}$ alkoxy, C$_3$-C$_{10}$ alkenyloxy, C$_3$-C$_{10}$ alkynyloxy, C$_3$-C$_{10}$ cycloalkyloxy, C$_5$-C$_{10}$ cycloalkenyloxy, C$_3$-C$_{10}$ heterocycloalkyloxy, C$_5$-C$_{10}$ heterocycloalkenyloxy, C$_6$-C$_{12}$ aryloxy, heteroaryloxy, C$_1$-C$_{10}$ alkylthio, C$_3$-C$_{10}$ alkenylthio, C$_3$-C$_{10}$ alkynylthio, C$_3$-C$_{10}$ cycloalkylthio, C$_5$-C$_{10}$ cycloalkenylthio, C$_3$-C$_{10}$ heterocycloalkylthio, C$_5$-C$_{10}$ heterocycloalkenylthio, C$_6$-C$_{12}$ arylthio, heteroarylthio and N(R)$_2$;

each R$_4$ is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, C$_1$-C$_{10}$ alkoxy, C$_3$-C$_{10}$ alkenyloxy, C$_3$-C$_{10}$ alkynyloxy, C$_3$-C$_{10}$ cycloalkyloxy, C$_5$-C$_{10}$ cycloalkenyloxy, C$_3$-C$_{10}$ heterocycloalkyloxy, C$_5$-C$_{10}$ heterocycloalkenyloxy, C$_6$-C$_{12}$ aryloxy, heteroaryloxy, C$_1$-C$_{10}$ alkylthio, C$_3$-C$_{10}$ alkenylthio, C$_3$-C$_{10}$ alkynylthio, C$_3$-C$_{10}$ cycloalkylthio, C$_5$-C$_{10}$ cycloalkenylthio, C$_3$-C$_{10}$ heterocycloalkylthio, C$_5$-C$_{10}$ heterocycloalkenylthio, C$_6$-C$_{12}$ arylthio, heteroarylthio, halo and N(R)$_2$;

R$_6$ is selected from the group consisting of C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, C$_1$-C$_{10}$ alkylthio, C$_3$-C$_{10}$ alkenylthio, C$_3$-C$_{10}$ alkynylthio, C$_3$-C$_{10}$ cycloalkylthio, C$_5$-C$_{10}$ cycloalkenylthio, C$_3$-C$_{10}$ heterocycloalkylthio, C$_5$-C$_{10}$ heterocycloalkenylthio, C$_6$-C$_{12}$, arylthio, heteroarylthio, —S(O)R$_3$, —S(O)$_2$R$_3$ and —C(O)R$_5$;

R" is the same as R or two R" taken together with the N atom to which they are attached may form a saturated, unsaturated or aromatic heterocyclic ring system;

Q is selected from halogen and —OS(O)$_2$Q$_1$; wherein Q$_1$ is selected from C$_1$-C$_4$ alkyl, C$_1$-C$_4$ perfluoroalkyl, phenyl, p-methylphenyl; and m is 1, 2, 3, 4, or 5.

In another embodiment, X is selected from the group consisting of NH, —C(O)—, —C(S)—, —C(O)O—, C(S)O—, and —C(S)S—, or is absent;

B is selected from the group consisting of C$_1$-C$_5$ alkylene, C$_2$-C$_5$ alkenylene, C$_2$-C$_5$ alkynylene, C$_3$-C$_{10}$ cycloalkylene, C$_5$-C$_{10}$ cycloalkenylene, C$_6$-C$_{12}$ arylene and C$_2$-C$_5$ acyl;

X' is selected from the group consisting of —O—, —S—, —NR—, —S—S—, —S(O)—, —P(O)(R$_1$)—, —OP(O)(R$_1$)—, OP(O)(R$_1$)O—, —OP(O)(R$_1$)OP(O)(R$_1$)O—, —C(O)—, —C(S)—, —C(O)O—, C(S)O—, —C(S)S—, —Se—,

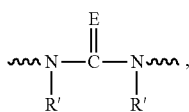

or is absent; wherein E is O, S or $N(R)_2^+$;

n is 0, 1 or 2; and

B' is $C_1$-$C_5$ selected from the group consisting of alkylene, $C_2$-$C_5$ alkenylene, $C_2$-$C_5$ alkynylene, $C_3$-$C_{10}$ cycloalkylene, $C_5$-$C_{10}$ cycloalkenylene, and $C_6$-$C_{12}$ arylene, or is absent; and wherein each R is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $OR_2$ and $C_2$-$C_{10}$ acyl;

R' is the same as R;

each $R_1$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, $OR_2$ and $N(R)_2$;

each $R_2$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, and $-C(O)R_5$;

each $R_5$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, OH, SH, and $N(R)_2$;

wherein for each instance that B and/or B' is arylene, the substituents directly attached to the respective arylene rings (including arsenoxide or arsenoxide equivalent), may be at any available position, and for example, may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, cyano, halo, cyanate, isocyanate, $OR_{2a}$, $SR_6$, nitro, arsenoxide, $-S(O)R_3$, $-OS(O)R_3$, $-S(O)_2R_3$, $-OS(O)_2R_3$, $-P(O)R_4R_4$, $-OP(O)R_4R_4$, $-N(R'')_2$, $NRC(O)(CH_2)_mQ$, $-C(O)R_5$,

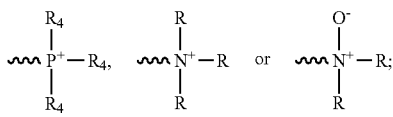

wherein R, $R_1$ and $R_5$ are as defined above; and $R_{2a}$ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $-S(O)R_3$, $-S(O)_2R_3$, $-P(O)(R_4)_2$, $N(R)_2$ and $-C(O)R_5$;

each $R_3$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio and $N(R)_2$;

each $R_4$ is independently selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_5$ alkynyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_5$ alkynylthio, $C_3$-$C_5$ cycloalkylthio, $C_5$-$C_5$ cycloalkenylthio, $C_6$-$C_{12}$ arylthio, halo and $N(R)_2$;

$R_6$ is independently selected from the group consisting of $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, $C_1$-$C_5$ alkylthio, $C_3$-$C_5$ alkenylthio, $C_3$-$C_5$ alkynylthio, $C_3$-$C_{10}$ cycloalkylthio, $C_5$-$C_{10}$ cycloalkenylthio, $C_6$-$C_{12}$ arylthio, $-S(O)R_3$, $-S(O)_2R_3$ and $-C(O)R_5$, R" is the same as R;

Q is selected from the group consisting of halogen and $-OS(O)_2Q_1$; wherein $Q_1$ is selected from $C_1$-$C_4$ alkyl, $C_1$-$C_4$ perfluoroalkyl, phenyl, p-methylphenyl; and m is 1, 2, 3, 4 or 5.

In another embodiment, X is absent;

B is selected from the group consisting of $C_1$-$C_5$ alkylene, $C_6$-$C_{12}$ arylene and $C_2$-$C_5$ acyl;

X' is selected from the group consisting of $-O-$, $-S-$, $-NR-$, $-S-S-$, $-S(O)-$, $-S(O)_2-$, $-P(O)(R_1)-$, $-C(O)-$, $-C(S)-$, $-C(O)O-$, $C(S)O-$, $-Se-$, and

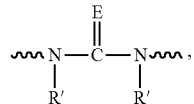

or absent; wherein E is O, S or $N(R)_2^+$;

n is 0, 1 or 2; and

B' is $C_1$-$C_5$ alkylene, $C_6$-$C_{12}$ arylene or is absent; and wherein each R is independently selected from the group consisting of hydrogen, $C_1$-$C_5$ alkyl, $C_3$-$C_{10}$ cycloalkyl, $C_6$-$C_{12}$ aryl, $OR_2$ and $C_2$-$C_5$ acyl;

R' is the same as R;

each $R_1$ is independently selected from the group consisting of hydrogen, $C_1$-$C_5$ alkyl, $C_3$-$C_{10}$ cycloalkyl, $C_6$-$C_{12}$ aryl, halo, $OR_2$ and $N(R)_2$;

each $R_2$ is independently selected from the group consisting of hydrogen, $C_1$-$C_5$ alkyl, $C_3$-$C_{10}$ cycloalkyl, $C_6$-$C_{12}$, aryl and $-C(O)R_5$;

each $R_5$ is independently selected from the group consisting of hydrogen, $C_1$-$C_5$ alkyl, $C_2$-$C_5$ alkenyl, $C_3$-$C_{10}$ cycloalkyl, $C_5$-$C_{10}$ cycloalkenyl, $C_6$-$C_{12}$ aryl, $C_1$-$C_5$ alkoxy, $C_3$-$C_5$ alkenyloxy, $C_3$-$C_{10}$ cycloalkyloxy, $C_5$-$C_{10}$ cycloalkenyloxy, $C_6$-$C_{12}$ aryloxy, $C_1$-$C_5$ alkylthio, $C_3$-$C_5$ alkenylthio, $C_3$-$C_{10}$ cycloalkylthio, $C_5$-$C_{10}$ cycloalkenylthio, $C_6$-$C_{12}$ arylthio, OH, SH and $N(R)_2$, wherein for each instance that B and/or B' is arylene, the substituents directly attached to the respective arylene rings (including arsenoxide or arsenoxide equivalent) may be at any available position on the respective ring(s) and, for example, may be in a para-, meta- or ortho-relationship, and wherein each alkylene, alkenylene, alkynylene, cycloalkylene, cycloalkenylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, $OR_{2a}$, $SR_6$, nitro, arsenoxide, $-S(O)R_3$, $-OS(O)R_3$, $-S(O)_2R_3$, $-OS(O)_2R_3$, $-P(O)R_4R_4$, $-OP(O)R_4R_4$, $-N(R'')_2$, $-NRC(O)(CH_2)_mQ$, $-C(O)R_5$,

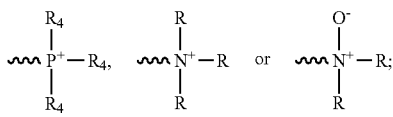

wherein R, $R_1$ and $R_5$ are as defined above; and $R_{2a}$ is selected from the group consisting of hydrogen, $C_1$-$C_5$ alkyl, $C_3$-$C_{10}$ cycloalkyl, $C_6$-$C_{12}$ aryl, $-S(O)R_3$, $-S(O)_2R_3$, $-P(O)(R_4)_2$ and $-C(O)R_5$, each $R_3$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, $C_1$-$C_5$ alkylthio, $C_3$-$C_{10}$ cycloalkylthio, $C_6$-$C_{12}$ arylthio and $N(R)_2$;

each $R_4$ is independently selected from the group consisting of hydrogen, $C_1$-$C_5$ alkyl, $C_3$-$C_{10}$ cycloalkyl, $C_6$-$C_{12}$ aryl, $C_1$-$C_5$ alkoxy, $C_3$-$C_{10}$ cycloalkyloxy, $C_6$-$C_{12}$ aryloxy, halo and $N(R)_2$;

$R_6$ is selected from the group consisting of $C_1$-$C_5$ alkyl, $C_3$-$C_{10}$ cycloalkyl, $C_6$-$C_{12}$ aryl, $C_1$-$C_5$ alkylthio, $C_3$-$C_{10}$ cycloalkylthio, $C_6$-$C_{12}$ arylthio, —S(O)$R_3$, —S(O)$_2R_3$ and —C(O)$R_5$, R" is the same as R;

Q is selected from halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4, or 5.

In a further embodiment, X is absent;

B is selected from the group consisting of $C_1$-$C_5$ alkylene, $C_6$-$C_{12}$ arylene and $C_2$-$C_5$ acyl;

X' is selected from the group consisting of —O—, —S—, —NR—, —C(O)—, and —C(O)O—, or is absent;

n is 1; and

B' is $C_1$-$C_5$ alkylene, $C_6$-$C_{12}$ arylene or is absent; and

R is selected from the group consisting of hydrogen, $C_1$-$C_5$ alkyl, $C_6$-$C_{12}$ aryl and $C_2$-$C_5$ acyl;

wherein for each instance that B and/or B' is arylene, the substituents directly attached to the respective arylene rings (including arsenoxide or arsenoxide equivalent), may be at any available position on the respective ring(s) and, for example, may be in a para-, meta- or ortho-relationship, and wherein each alkylene, arylene, and acyl may be independently substituted with hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, halo, cyano, cyanate, isocyanate, $OR_{2a}$, $SR_6$, nitro, arsenoxide, —S(O)$R_3$, —S(O)$_2R_3$, —P(O)$R_4R_4$, —N(R")$_2$, —NRC(O)(CH$_2$)$_m$Q, —C(O)$R_5$,

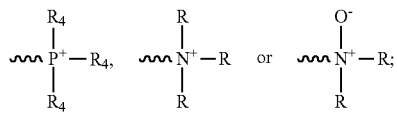

wherein each R is independently selected from the group consisting of hydrogen, $C_1$-$C_5$ alkyl, $C_6$-$C_{12}$ aryl and $C_2$-$C_5$ acyl;

$R_{2a}$ is selected from the group consisting of hydrogen, $C_1$-$C_5$ alkyl, $C_6$-$C_{12}$ aryl, —S(O)$R_3$, —S(O)$_2R_3$, —P(O)(R$_4$)$_2$ and —C(O)$R_5$;

each $R_3$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, and $C_6$-$C_{12}$ arylthio;

each $R_4$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, halo and $N(R)_2$;

each $R_5$ is independently selected from the group consisting of hydrogen, $C_1$-$C_5$ alkyl, $C_6$-$C_{12}$ aryl, $C_1$-$C_5$ alkoxy, $C_6$-$C_{12}$ aryloxy, $C_1$-$C_5$ alkylthio, $C_6$-$C_{12}$ arylthio, OH, SH and $N(R)_2$;

$R_6$ is selected from the group consisting of $C_1$-$C_5$ alkyl, $C_6$-$C_{12}$ aryl, $C_1$-$C_5$ alkylthio, $C_6$-$C_{12}$ arylthio, —S(O)$R_3$, —S(O)$_2R_3$ and —C(O)$R_5$, R" is the same as R above;

Q is selected from halogen and —OS(O)$_2Q_1$; wherein $Q_1$ is selected from $C_1$-$C_4$ alkyl, $C_1$-$C_4$ perfluoroalkyl, phenyl, p-methylphenyl; and m is 1, 2, 3, 4, or 5.

In yet another embodiment, X is absent;

B is $C_2$-$C_5$ acyl;

X' is NR;

n is 1;

B' is phenylene; and

R is H;

wherein the substituents directly attached to the phenylene ring may be at any available position, as illustrated, for example, by Formula (III):

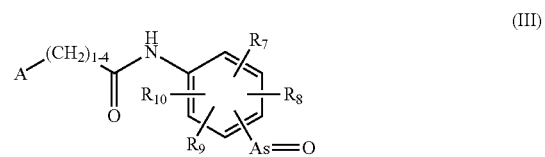

(III)

wherein $R_7$ to $R_{10}$ are independently selected from the group consisting of hydrogen, $C_1$-$C_5$ alkyl, $C_6$-$C_{12}$ aryl, halogen, hydroxy, amino, nitro, carboxy, $C_1$-$C_5$ alkoxy, —OS(O)$_2R_3$ and —NHC(O)CH$_2$Q wherein Q is halogen, —OS(O)$_2$CH$_3$, —OS(O)$_2$C$_6$H$_5$ and —OS(O)$_2$-p tolyl; and wherein, when any one of $R_7$ to $R_{10}$ is $C_1$-$C_5$ alkyl, $C_6$-$C_{12}$ aryl, $C_1$-$C_5$ alkoxy, —OS(O)$_2R_3$ it is capable of forming a fused ring with the phenylene; and further wherein, at least one of $R_7$ to $R_{10}$ is $C_1$-$C_5$ alkyl, $C_6$-$C_{12}$ aryl, $C_1$-$C_5$ alkoxy, or —OS(O)$_2R_3$, in combination with at least any one other of $R_7$ to $R_{10}$, is capable of forming a fused ring with the phenylene.

More typically, $R_7$ to $R_{10}$ are independently selected from the group consisting of hydrogen, halogen, hydroxy, amino, nitro, cyano, carboxy, $C_1$-$C_5$ alkoxy, methyl, ethyl, isopropyl, tert-butyl, phenyl and —NHC(O)CH$_2$Q wherein Q is halogen, —OS(O)$_2$CH$_3$, —OS(O)$_2$C$_6$H$_5$ and —OS(O)$_2$-p tolyl.

For example, when the pendant group A is glutathione, the compound of formula (III) may be represented as

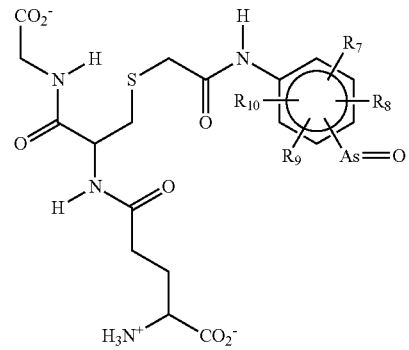

Further, when B' is arylene, the substituents attached to the arylene ring may be at any available position on the arylene ring. For example, the substituents may be in a meta- or para-relationship relative to the —As=O group.

In another embodiment, an arsenoxide compound used in accordance with the present invention is selected from the following compounds:

11 12
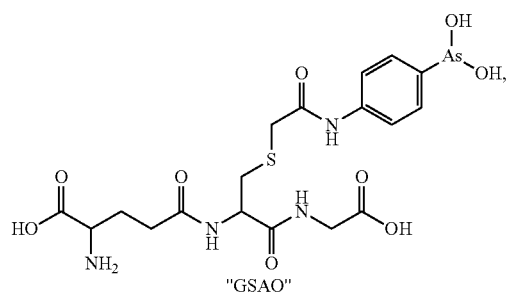
1
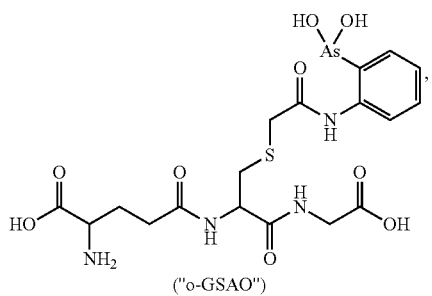
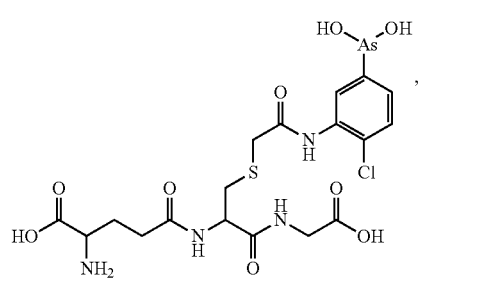
2 3
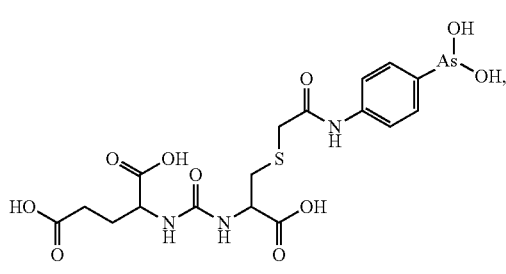
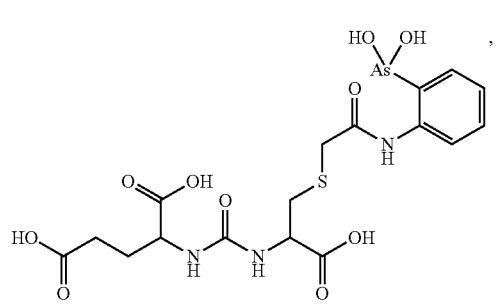
4 5
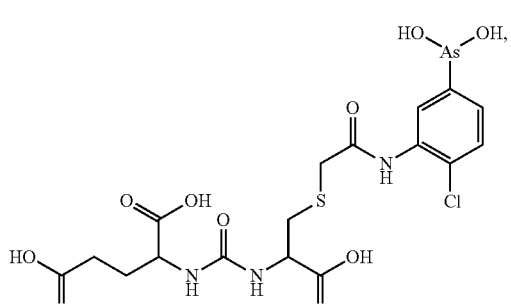
6
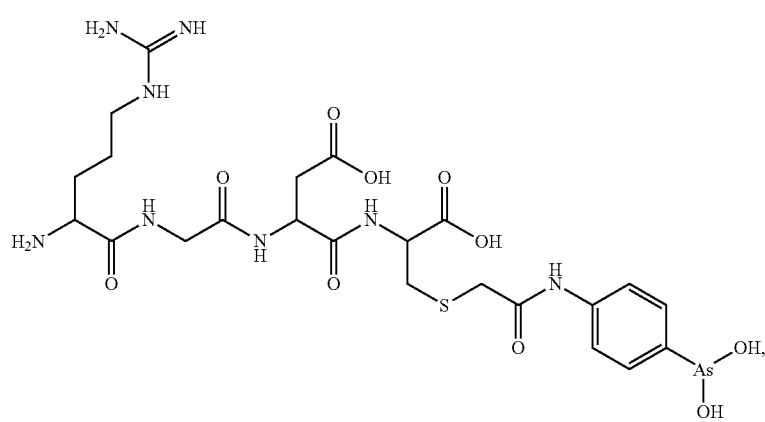
7 8
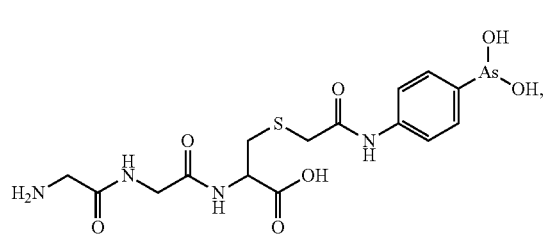
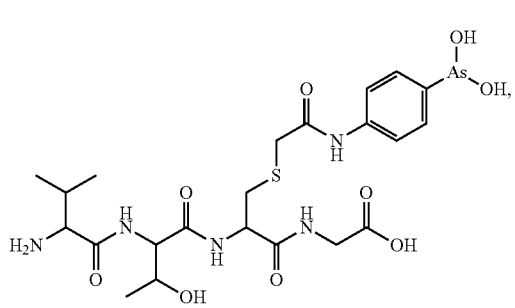

-continued
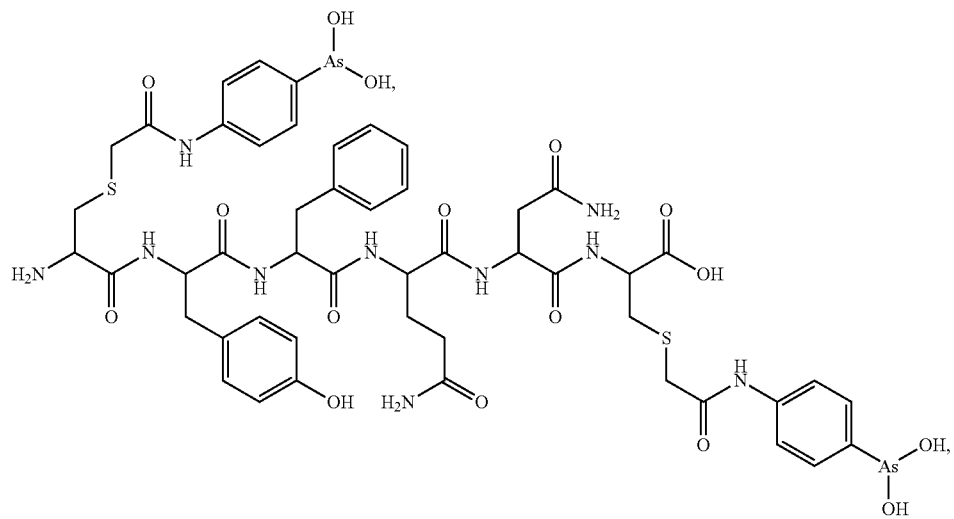
9
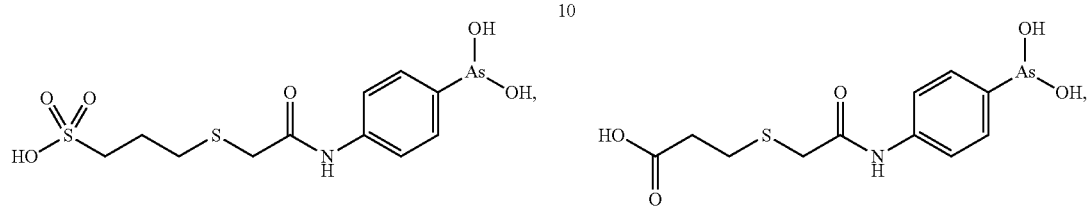
10
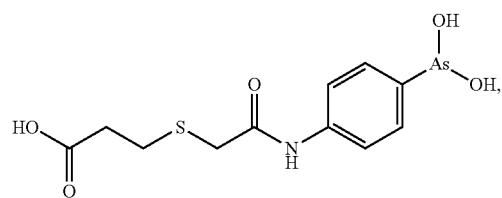
11
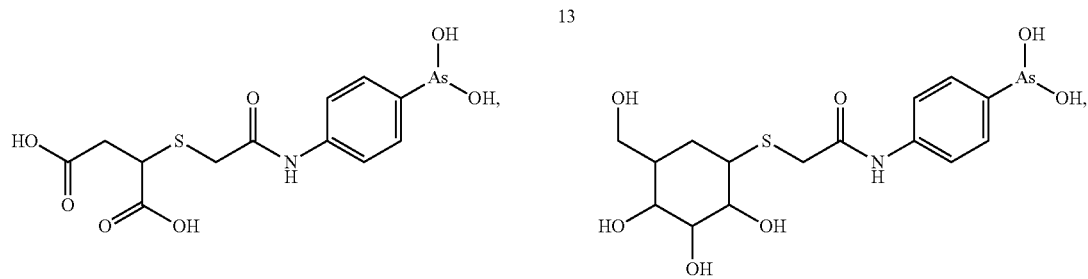
13
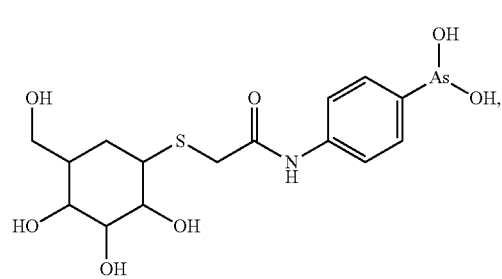
14
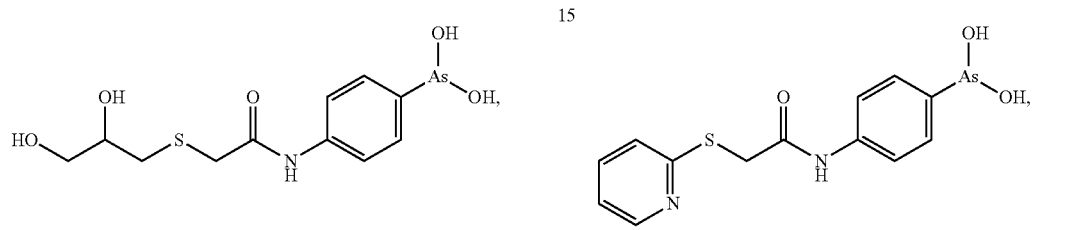
15
20
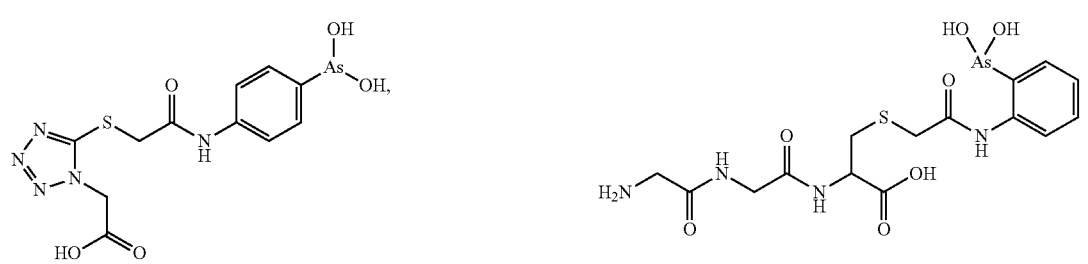
21
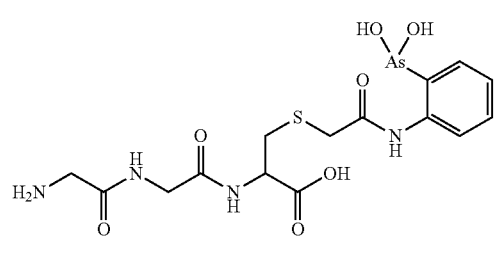
22
and

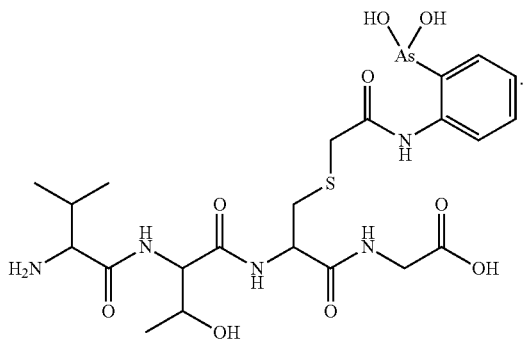

Other compounds which may interact with procoagulant platelets include compounds according to Formula (IV) illustrated below:

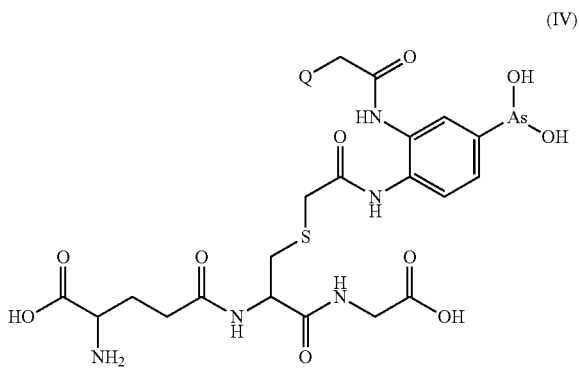

wherein Q is any halogen.

Another form of an arsenoxide compound which may interact with procoagulant platelets is a compound according to Formula (V):

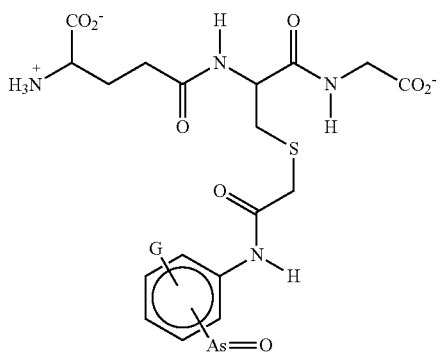

wherein G is selected from the group consisting of hydrogen, halogen, hydroxy, amino, nitro, cyano, carboxy, $C_1$-$C_5$ alkoxy, $C_1$-$C_5$ alkyl and $C_6$-$C_{12}$, aryl and —NHC(O)CH$_2$Q, wherein Q is halogen, —OS(O)$_2$CH$_3$, —OS(O)$_2$C$_6$H$_5$ or —OS(O)$_2$-p tolyl.

Typically, G is selected from the group consisting of hydrogen, halogen, hydroxy, amino, nitro, carboxy, $C_1$-$C_5$ alkoxy, methyl, ethyl, isopropyl, tert-butyl, phenyl, and —NHC(O)CH$_2$Q, wherein Q is the group consisting of halogen, —OS(O)$_2$CH$_3$, —OS(O)$_2$C$_6$H$_5$ and —OS(O)$_2$-p tolyl.

In one embodiment, in a compound of Formula (V), G is hydroxy, fluorine, amino, or nitro.

In another embodiment, group G is in an ortho-, meta-, or para-relationship to the arsenoxide group. For example, in another embodiment G is in an ortho- or para-relationship to the arsenoxide group.

Typically the activity of the arsenic atom may be modified by the group G, when G and the arsenic atom are in an ortho or para relationship to one another. For example, when G is an electron donating group such as OH (ionised to O⁻ at physiological pH), the arsenic atom may be deactivated towards dithiols and may become more selective, for example, only reacting with very reactive dithiols. Alternatively, when G is an electron withdrawing group, such as NO$_2$, electron density may be drawn away from the arsenic atom, making it more reactive to dithiols. Selective inhibition of some redox proteins and not others may be achieved by manipulation of G.

Another form of an arsenoxide compound capable of interacting with procoagulant platelets is a compound according to Formula (VI):

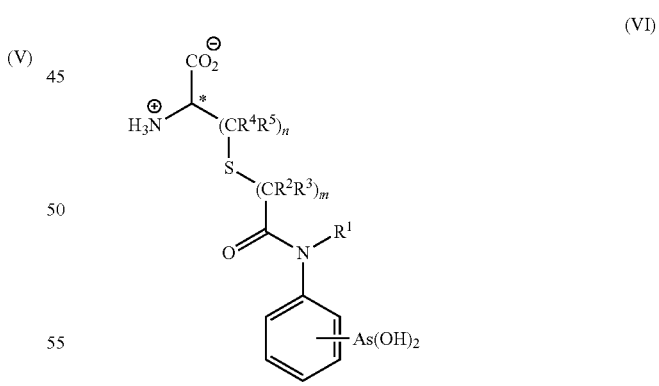

wherein
the As(OH)$_2$ group may be ortho-, meta- or para- to the N-atom on the phenyl ring;
$R^1$ is selected from hydrogen and $C_{1-3}$ alkyl;
$R^2$ and $R^3$ may be the same or different and are independently selected from hydrogen, optionally substituted $C_{1-3}$ alkyl, optionally substituted cyclopropyl, optionally substituted $C_{2-3}$ alkenyl; and optionally substituted $C_{1-3}$ alkoxy;
$R^4$ and $R^5$ may be the same or different and are independently selected from hydrogen, optionally substituted $C_{1-3}$ alkyl, optionally substituted cyclopropyl, optionally substituted $C_{2-3}$ alkenyl; and optionally substituted $C_{1-3}$ alkoxy;

m is an integer selected from 1, 2 and 3;

n is an integer selected from 1, 2 and 3;

* indicates a chiral carbon atom; and salts and hydrates thereof.

In one embodiment, optional substituents may be the same or different and are independently selected from $C_{1-3}$ alkyl, cyclopropyl, $C_{1-3}$ alkoxy, —$CH_2$—$(C_{1-3})$alkoxy, $C_{6-10}$ aryl, —$CH_2$-phenyl, halo, hydroxyl, hydroxy($C_{1-3}$)alkyl, and halo-($C_{1-3}$)alkyl, e.g, $CF_3$, $CH_2CF_3$. In one embodiment the optional substituents are independently selected from hydroxyl, methoxy, halo, methyl, ethyl, propyl, cyclopropyl, $CH_2OH$ and $CF_3$. In one embodiment there are no optional substituents.

In one embodiment, the $As(OH)_2$ group may be ortho- or para- to the N-atom on the phenyl ring. In one embodiment, the $As(OH)_2$ group is para- to the N-atom on the phenyl ring.

In another embodiment the $As(OH)_2$ group is ortho- to the N-atom on the phenyl ring.

In one embodiment, $R^1$ may be hydrogen, methyl or ethyl. In one embodiment $R^1$ is hydrogen.

In one embodiment, $R^2$ and $R^3$ may be the same or different. $R^2$ and $R^3$ may be independently selected from hydrogen, $C_{1-3}$ alkyl, $C_{2-3}$ alkenyl, $C_{1-3}$ alkoxy, halo($C_{1-3}$) alkoxy, hydroxy($C_{1-3}$)alkyl and halo($C_{1-3}$)alkyl. In a preferred embodiment $R^2$ and $R^3$ may be independently selected from hydrogen, methyl, ethyl, methoxy, vinyl, $CH_2OH$, $CF_3$ and $OCF_3$. In another preferred embodiment $R^2$ and $R^3$ may be independently selected from hydrogen, methyl and ethyl. In another embodiment $R^2$ is methyl and $R^3$ is hydrogen. In another embodiment $R^2$ and $R^3$ are both hydrogen.

In one embodiment, $R^4$ and $R^5$ may be the same or different. $R^4$ and $R^5$ may be independently selected from hydrogen, $C_{1-3}$ alkyl, $C_{2-3}$ alkenyl, $C_{1-3}$ alkoxy, halo($C_{1-3}$) alkoxy, hydroxy($C_{1-3}$)alkyl and halo-($C_{1-3}$)alkyl. In a preferred embodiment $R^4$ and $R^5$ may be independently selected from hydrogen, methyl, ethyl, methoxy, vinyl, hydroxy($C_{1-3}$)alkyl, $CF_3$ and $OCF_3$. In another preferred embodiment $R^4$ and $R^5$ may be independently selected from hydrogen, methyl, ethyl and $CH_2OH$. In another embodiment $R^4$ is methyl or ethyl and $R^5$ is hydrogen or methyl. In another embodiment $R^4$ is methyl and $R^5$ is hydrogen. In another embodiment $R^4$ and $R^5$ are both hydrogen. In another embodiment $R^4$ and $R^5$ are both methyl.

In one embodiment, m is 1 or 2. In another embodiment n is 1 or 2. In another embodiment m and n are both 1.

In one embodiment of compounds of formula (VI), the $As(OH)_2$ group is ortho- or para- to the N-atom on the phenyl ring; $R^1$ is hydrogen or methyl; $R^2$ and $R^3$ are independently selected from hydrogen, $C_{1-3}$ alkyl, $C_{2-3}$ alkenyl, $C_{1-3}$ alkoxy, halo-($C_{1-3}$)alkoxy, hydroxy($C_{1-3}$)alkyl and halo($C_{1-3}$)alkyl; $R^4$ and $R^5$ are independently selected from hydrogen, $C_{1-3}$ alkyl, $C_{2-3}$ alkenyl, $C_{1-3}$ alkoxy, halo ($C_{1-3}$)alkoxy, hydroxy($C_{1-3}$)alkyl and halo($C_{1-3}$)alkyl; m is 1 or 2; and n is 1 or 2.

In another embodiment of compounds of formula (VI), the $As(OH)_2$ group is ortho- or para- to the N-atom on the phenyl ring; $R^1$ is hydrogen or methyl; $R^2$ and $R^3$ are independently selected from hydrogen, methyl, ethyl, methoxy, vinyl, $CH_2OH$, $CF_3$ and $OCF_3$; $R^4$ and $R^5$ are independently selected from hydrogen, methyl, ethyl, $CH_2OH$, methoxy, vinyl, $CF_3$ and $OCF_3$; m is 1; and n is 1.

In a further embodiment of compounds of formula (VI), the $As(OH)_2$ group is ortho- or para- to the N-atom on the phenyl ring; $R^1$ is hydrogen or methyl; $R^2$ and $R^3$ are independently selected from hydrogen, methyl and ethyl; $R^4$ and $R^5$ are independently selected from hydrogen, methyl and ethyl; m is 1; and n is 1.

In another embodiment of compounds of formula (VI), the $As(OH)_2$ group is ortho- or para- to the N-atom on the phenyl ring; $R^1$ is hydrogen or methyl; $R^2$ is hydrogen or methyl; $R^3$ is hydrogen or methyl; $R^4$ is hydrogen, methyl or ethyl; $R^5$ is hydrogen or methyl; m is 1; and n is 1.

In another embodiment of compounds of formula (VI), the $As(OH)_2$ group is para- to the N-atom on the phenyl ring; $R^1$ is hydrogen; $R^2$ is hydrogen or methyl; $R^3$ is hydrogen; $R^4$ is hydrogen or methyl; $R^5$ is hydrogen or methyl; m is 1; and n is 1.

In a particular embodiment of the invention the compound of formula (VI) is:

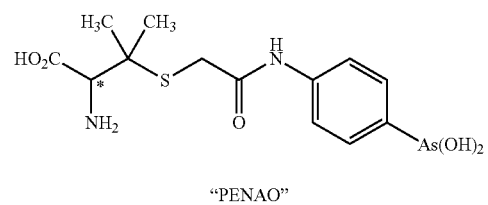

"PENAO"

This compound is referred to herein as "Penicillamine-arsenoxide".

In another embodiment of the invention the compound of formula (VI) is:

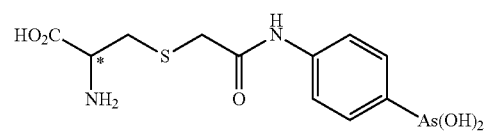

This compound may be referred to herein as "cysteinyl-phenylarsenoxide".

Typically, in the arsenoxide compounds capable of interacting with procoagulant platelets, the arsenoxide group (—As=O) may be replaced by an arsenoxide equivalent.

An arsenoxide equivalent is defined herein as any dithiol reactive species that shows essentially the same affinity towards dithiols as —As=O. Typically, arsenoxide equivalent includes dithiol reactive entities, such as As, Ge, Sn and Sb species. More typically an arsenoxide equivalent can be represented by -$D(Z_1)(Z_2)$. Arsenoxide equivalents are expected to exhibit identical or substantially identical activity to that of the corresponding arsenoxide.

Typically, for arsenoxide equivalents of the form -$D(Z_1)(Z_2)$, D will be, for example, As, RSn, Sb, or RGe, and $Z_1$ and $Z_2$ will be labile groups (i.e. groups easily displaced under physiological conditions). $Z_1$ and $Z_2$, may be identical or different, and may either be connected or independent from each other (bound only to the arsenic atom).

Suitable arsenoxide equivalents include the following:

wherein $Z_1$ and $Z_2$ are selected from the group consisting of OH, $C_1$-$C_{10}$ alkoxy, $C_6$-$C_{10}$ aryloxy, $C_1$-$C_{10}$ alkylthio, $C_6$-$C_{10}$ arylthio, $C_1$-$C_{10}$ alkylseleno, arylseleno, F, Cl, Br and I;

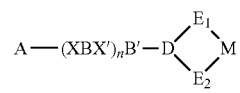

wherein $E_1$=$E_2$=O, $E_1$=O and $E_2$=S or $E_1$=$E_2$=S; M is R''' and R'''' are independently selected from the group consisting of hydrogen, $C_1$-$C_{10}$ alkyl, $C_6$-$C_{12}$ aryl, halogen, $C_1$-$C_{10}$ alkoxy, $C_6$-$C_{10}$ aryloxy, hydroxy and carboxy; and n=1 to 10.

For arsenoxide equivalents of the form $D(Z_1)(Z_2)$, when D is As and $Z_1$ and $Z_2$ are OH, the arsenoxide equivalent may be in equilibrium with polymeric species, as depicted below.

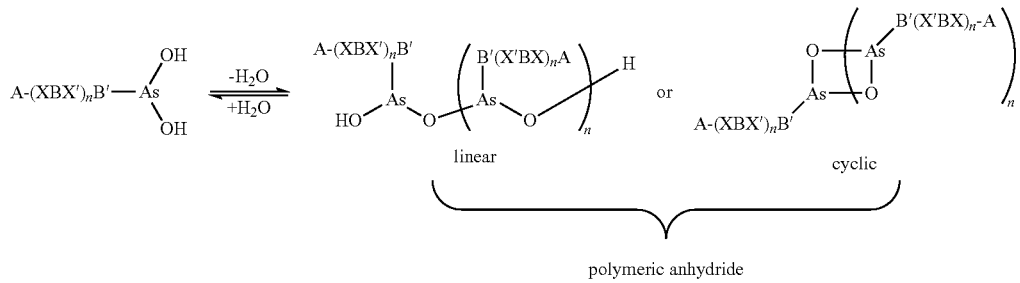

polymeric anhydride

In respect of the equilibrium depicted above, arsenic is one of many elements whose hydroxy species exist in equilibrium with the corresponding polymeric anhydrides (Doak & Freedman, 1970). Therefore, arsenoxide compounds may actually exist as low or medium molecular weight polymers (eg n=3 to 6). However, the dehydration reaction is reversible, and therefore soluble polymeric anhydrides are expected to behave as arsenoxide equivalents, that is, they are expected to bind to closely spaced dithiols in substantially the same way as the monomeric —As(OH)$_2$ species.

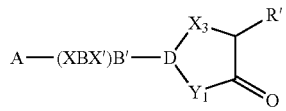

wherein $X_3$=NH, $Y_1$=O; $X_3$=$Y_1$=O or $X_3$=S, $Y_1$=O, and R' is selected from the group consisting of hydrogen, $C_1$-$C_{10}$ alkyl, $C_6$-$C_{12}$ aryl, and carboxy, or is one of the twenty amino acid side chains;

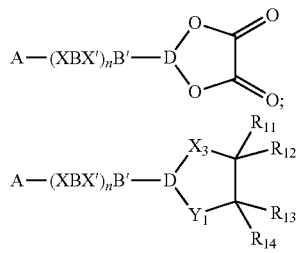

wherein $X_3$=$Y_1$=O; $X_3$=NH, $Y_1$=O; $X_3$=S, $Y_1$=O; $X_3$=$Y_1$=NH; or $X_3$=S, $Y_1$ NH; or $X_3$=S, $Y_1$=NH and $R_{11}$ to $R_{14}$ are selected from the group consisting of hydrogen, $C_1$-$C_{10}$ alkyl, $C_6$-$C_{12}$ aryl, and $CO_2H$;

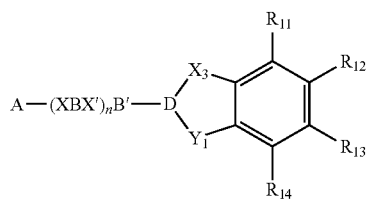

wherein $X_3$=$Y_1$=O, or $X_3$=NH, $Y_1$=O; and $R_{11}$ to $R_{14}$ are selected from the group consisting of hydrogen, $C_1$-$C_{10}$ alkyl, $C_6$-$C_{12}$ aryl, halogen, $C_1$-$C_{10}$ alkoxy, and $CO_2H$.

Typically, (XBX')B' is as defined above.

With reference to the first and second aspects of the invention, in one embodiment the platelet may be a P-selectin+ platelet.

With reference to the second and third aspects of the invention, in one embodiment the platelets may be P-selectin+ platelets.

The invention also provides an arsenoxide (or arsenoxide equivalent) compound for use in identifying a patient at risk of developing a prothrombotic or thrombotic condition.

Abbreviations and Definitions

The following are some definitions that may be helpful in understanding the description of the present invention. These are intended as general definitions and should in no way limit the scope of the present invention to those terms alone, but are put forth for a better understanding of the following description.

Unless the context requires otherwise or specifically stated to the contrary, integers, steps, or elements of the invention recited herein as singular integers, steps or elements clearly encompass both singular and plural forms of the recited integers, steps or elements.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

In the context of this specification, GSAO refers to 4-(N—(S-glutathionylacetyl)amino)phenylarsinous acid.

The term "arsenical" as used herein, includes any compound that contains arsenic.

The term "acyl" as used herein, includes monovalent and divalent alkyl, alkenyl, alkynyl, cycloalkyl and cycloalkenyl moieties possessing a terminal carbonyl substituent wherein attachment may occur at the hydrocarbon moiety, the carbonyl moiety or both.

The term "alkyl" as used herein, includes within its meaning monovalent, saturated, straight and branched chain hydrocarbon radicals.

The term "alkenyl" as used herein, includes within its meaning, monovalent, straight and branched chain hydrocarbon radicals having at least one double bond.

The term "alkynyl" as used herein, includes within its meaning, monovalent, straight and branched chain hydrocarbon radicals having at least one triple bond.

The term "alkylene" as used herein, includes within its meaning divalent, saturated, straight chain hydrocarbon radicals.

The term "alkenylene" as used herein, includes within its meaning, divalent, straight chain hydrocarbon radicals having at least one double bond.

The term "alkynylene" as used herein, includes within its meaning, divalent, straight chain hydrocarbon radicals having at least one triple bond.

The term "alkoxy" as used herein refers to straight chain or branched alkyloxy (i.e, O-alkyl) groups, wherein alkyl is as defined above. Examples of alkoxy groups include methoxy, ethoxy, n-propoxy, and isopropoxy.

The term "amino" as used herein refers to groups of the form —$NR^aR^b$ wherein $R^a$ and $R^b$ are individually selected from hydrogen, optionally substituted ($C_{1-4}$)alkyl, optionally substituted ($C_{2-4}$)alkenyl, optionally substituted ($C_{2-4}$) alkynyl, optionally substituted ($C_{6-10}$ aryl and optionally substituted aralkyl groups, such as benzyl. The amino group may be a primary, secondary or tertiary amino group.

In the context of this specification the term "arsenoxide" is synonymous with "arsinous acid" and refers to the moiety $As(OH)_2$, which may also be represented as As=O.

The term "amino acid" as used herein includes naturally and non-naturally occurring amino acids, as well as substituted variants thereof. Thus, (L) and (D) forms of amino acids are included in the scope of the term "amino acid". The term "amino acid" includes within its scope glycine, alanine, valine, leucine, isoleucine, methionine, proline, phenylalanine, tryptophan, serine, threonine, cysteine, tyrosine, asparagine, glutamine, aspartic acid, glutamic acid, lysine, arginine, and histidine. The backbone of the amino acid residue may be substituted with one or more groups independently selected from ($C_{1-6}$)alkyl, halogen, hydroxy, hydroxy($C_{1-6}$)alkyl, aryl, e.g, phenyl, aryl($C_{1-3}$)alkyl, e.g, benzyl, and ($C_{3-6}$)cycloalkyl.

The term "aryl" as used herein, includes within its meaning monovalent, single, polynuclear, conjugated and fused aromatic hydrocarbon radicals.

The term "arylalkyl" or variants such as "aralkyl" as used herein, includes within its meaning monovalent ("aryl") and divalent ("arylene"), single, polynuclear, conjugated and fused aromatic hydrocarbon radicals attached to divalent, saturated, straight or branched chain alkylene radicals. Examples of arylalkyl groups include benzyl.

The term "arylene" as used herein, includes within its meaning divalent, single, polynuclear, conjugated and fused aromatic hydrocarbon radicals.

The term "closely spaced dithiol" as used herein, includes within its meaning thiols that are chemically vicinal, as well as thiols brought into spacial apposition by virtue of molecular conformation.

The term "cycloalkyl" as used herein, includes within its meaning monovalent, saturated, monocyclic, bicyclic, polycyclic or fused polycyclic hydrocarbon radicals.

The term "cycloalkylene" as used herein, includes within its meaning divalent, saturated, monocyclic, bicyclic, polycyclic or fused polycyclic hydrocarbon radicals.

The term "cycloalkenyl" as used herein, includes within its meaning monovalent, saturated, monocyclic, bicyclic, polycyclic or fused polycyclic hydrocarbon radicals having at least one double bond.

The term "cycloalkenylene" as used herein, includes within its meaning divalent, saturated, monocyclic, bicyclic, polycyclic or fused polycyclic hydrocarbon radicals having at least one double bond.

The term "halogen" or variants such as "halide" or "halo" as used herein refers to fluorine, chlorine, bromine and iodine.

The term "heteroaryl" as used herein, includes within its meaning monovalent, single, polynuclear, conjugated and fused aromatic radicals having 1 to 12 atoms wherein 1 to 6 atoms are heteroatoms selected from O, N and S.

The term "heteroarylene" or "heteroaryl" as used herein, includes within its meaning divalent, single, polynuclear, conjugated and fused aromatic radicals having 1 to 12 atoms wherein 1 to 6 atoms are heteroatoms selected from O, N and S.

The term "heteroatom" or variants such as "hetero-" as used herein refers to O, N, NH and S.

The term "heterocycloalkyl" as used herein, includes within its meaning monovalent, saturated, monocyclic, bicyclic, polycyclic or fused radicals wherein 1 to 5 atoms are heteroatoms selected from O, N or S.

The term "heterocycloalkylene" as used herein, includes within its meaning divalent, saturated, monocyclic, bicyclic, polycyclic or fused polycyclic radicals wherein 1 to 5 atoms are heteroatoms selected from O, N or S.

The term "heterocycloalkenyl" as used herein, includes within its meaning monovalent, saturated, monocyclic, bicyclic, polycyclic or fused polycyclic radicals having at least 1 double bond and wherein 1 to 5 atoms are heteroatoms selected from O, N or S.

The term "heterocycloalkenylene" as used herein, includes within its meaning divalent, saturated, monocyclic, bicyclic, polycyclic or fused polycyclic radicals having at least one double bond and wherein 1 to 5 atoms are heteroatoms selected from O, N or S.

The term "optionally substituted" as used herein means the group to which this term refers may be unsubstituted, or may be substituted with one or more groups independently selected from alkyl, alkenyl, alkynyl, cycloalkyl, cycloalkenyl, heterocycloalkyl, halo, haloalkyl, haloalkynyl, hydroxyl, hydroxyalkyl, alkoxy, thioalkoxy, alkenyloxy, haloalkoxy, haloalkenyloxy, $NO_2$, $NR^aR^b$, nitroalkyl, nitroalkenyl, nitroalkynyl, nitroheterocyclyl, alkylamino, dialkylamino, alkenylamine, alkynylamino, acyl, alkenoyl, alkynoyl, acylamino, diacylamino, acyloxy, alkylsulfonyloxy, heterocycloxy, heterocycloamino, haloheterocycloalkyl, alkylsulfenyl, alkylcarbonyloxy, alkylthio, acylthio, phosphorus-containing groups such as phosphono and phosphinyl, aryl, heteroaryl, alkylaryl, aralkyl, alkylheteroaryl, cyano, cyanate, isocyanate, $CO_2H$, $CO_2$alkyl, $C(O)NH_2$, —$C(O)NH(alkyl)$, and —$C(O)N(alkyl)_2$. Preferred substituents include $C_{1-3}$ alkyl, $C_{1-3}$ alkoxy, —$CH_2$—($C_{1-3}$) alkoxy, $C_{6-10}$ aryl, e.g., phenyl, —$CH_2$-phenyl, halo, hydroxyl, hydroxy($C_{1-3}$)alkyl, and halo-($C_{1-3}$)alkyl, e.g., $CF_3$, $CH_2CF_3$. Particularly preferred substituents include $C_{1-3}$ alkyl, $C_{1-3}$ alkoxy, halo, hydroxyl, hydroxy($C_{1-3}$)alkyl, e.g., $CH_2OH$, and halo-($C_{1-3}$)alkyl, e.g., $CF_3$, $CH_2CF_3$.

In the context of this specification the term "administering" and variations of that term including "administer" and "administration", includes contacting, applying, delivering or providing a compound or composition of the invention to an organism, or a surface by any appropriate means.

In the context of this specification the term "effective amount" includes within its meaning a sufficient but non-toxic amount of a compound or composition of the invention to provide a desired effect. Thus, the term "therapeutically effective amount" includes within its meaning a sufficient but non-toxic amount of a compound or composition of the invention to provide the desired therapeutic effect. The exact amount required will vary from subject to subject depending on factors such as the species being treated, the sex, age and general condition of the subject, the severity of the condition being treated, the particular agent being administered, the mode of administration, and so forth. Thus, it is not possible to specify an exact "effective amount". However, for any given case, an appropriate "effective amount" may be determined by one of ordinary skill in the art using only routine experimentation.

In the context of this specification, the term "arsenoxide equivalent" refers to any dithiol reactive species that shows essentially the same affinity towards dithiols as —As=O or As(OH)$_2$, and the term includes, for example, groups comprising a transition element, and any trivalent arsenical that is either hydrolysed to —As=O or —As(OH)$_2$ when dissolved in an aqueous medium (such as cell culture buffers and the fluids contained in the organism being treated).

In the context of this specification the term "substantially cell membrane impermeable group" refers to any group which limits the rate at which a compound passes through a cell membrane and into the cell. A substantially cell membrane impermeable group may limit the rate of entry of a compound into a cell by virtue of one or more properties such as, for example, charge, size (molecular weight), polarity, lipophilicity, hydrophilicity, etc.

In the context of this specification the term "activated platelet" refers to platelets that aggregate to form the platelet plug and also provide the surface for the assembly of the coagulation factors.

In the context of this specification the term "procoagulant platelet" refers to a susbset of activated platelets that have distinct properties including the ability to support thrombin generation.

DESCRIPTION OF EMBODIMENTS

Figure 1:
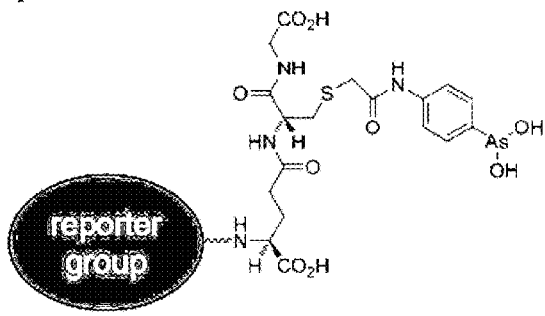
FIG. 1. GSAO labels a subpopulation of activated platelets. A. Structure of GSAO and site of conjugation of AF647, Oregon Green or biotin. B. Washed human platelets were stimulated with calcium ionophore (1 µM) and activation and plasma membrane compromise measured by flow cytometry. Activated platelets were detected from surface elaboration of P-selectin and plasma membrane compromise by labeling with GSAO-AF647 or negative control GSCA-AF647. C. Washed human platelets were left unstimulated or stimulated with thrombin (0.1 units/mL), collagen (5 µg/mL), or thrombin (0.1 units/mL) and collagen (5 µg/mL), and exposure of P-selectin and labeling with GSAO-AF647 measured by flow cytometry. D. Platelet stimulation with both thrombin and collagen results in significantly more labeling with GSAO-AF647 than with either agonist alone. E. Washed human platelets were stimulated with collagen or collagen-related peptide and co-labeling with P-selectin and GSAO-AF647 measured by flow cytometry.
Figure 1:
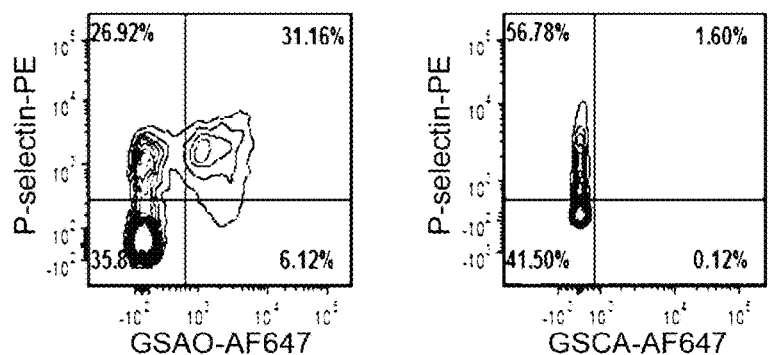
Figure 1:
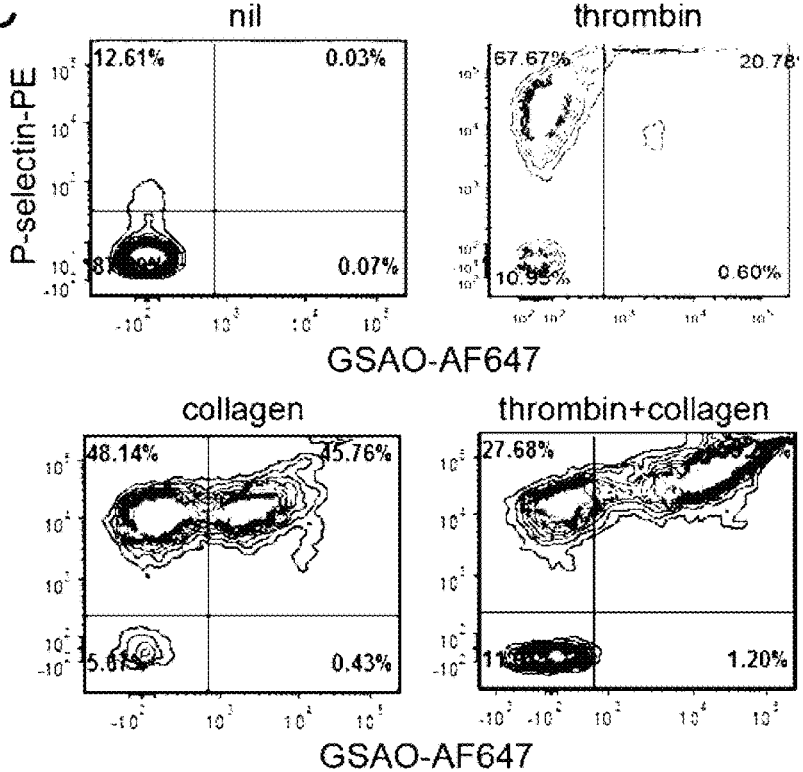
Figure 1:
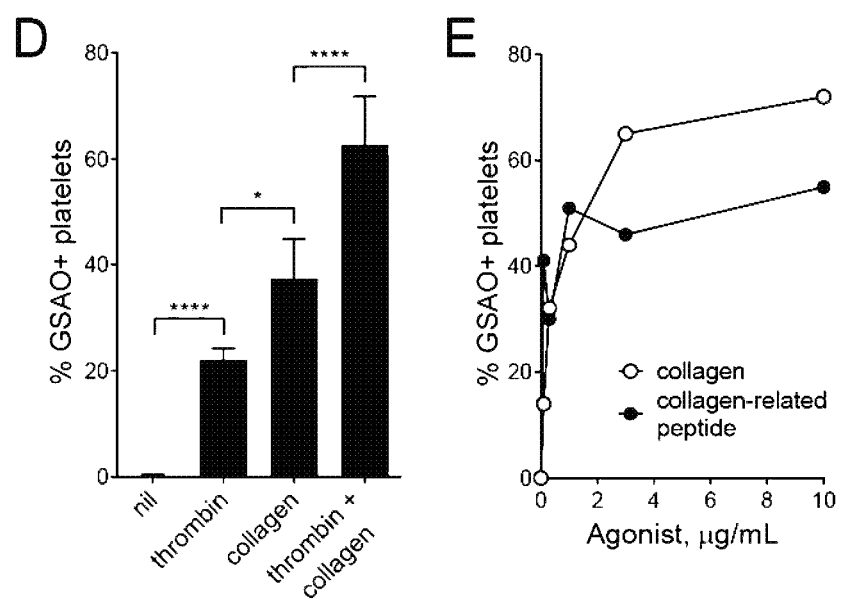

The present invention relates to a process for identifying procoagulant platelets in vitro or in vivo, and the identification of compounds which selectively inhibit formation of procoagulant platelets.

The concept of the procoagulant platelet is central to the current model of hemostasis postulated by the inventors. It localizes coagulation activation and fibrin formation to the activated platelet clot. Until now, it has been difficult to directly measure the functional contribution of procoagulant platelets to clot formation due to the lack of an effective marker that can be used in vitro and in vivo. Other markers include annexin V, mitochondrial membrane dyes, Factor Va staining and direct morphological visualisation by differential interference contrast microscopy. These have been problematic for a number of reasons including the imperfect correlation between all of these markers and the procoagulant population. Furthermore, function blocking probes such as annexin V and lactadherin may perturb the system that is being measured.

The present inventors have demonstrated that arsenoxide compounds, such as GSAO, specifically, rapidly and stably marks procoagulant necrotic platelets in vitro and in vivo and does not affect their function.

Using GSAO the inventors were able to show that necrotic platelets are generated within a few seconds of agonist stimulation in vitro and are procoagulant. They are also generated in vivo during formation of occlusive murine thrombi and provide a procoagulant surface. In addition, analysis of platelets from human subjects receiving aspirin indicates that procoagulant necrotic platelets form despite aspirin therapy, but are attenuated by inhibition of the necrosis pathway.

Arsenoxide compounds, such as GSAO, have several features that are particularly useful in a platelet necrosis marker. They complex with cytoplasmic proteins rather than DNA, the binding is independent of calcium and the interaction is covalent so the compound does not wash out. It also detects platelet membrane compromise within a few seconds and concentrates in the cytoplasm, which results in an exceptional signal to noise ratio. Importantly, arsenoxide compounds, such as GSAO, do not perturb measures of platelet function or coagulation in vitro or in vivo. In addition, an inert control compound, GSCA, provides for a high level of confidence with respect to specificity of GSAO labeling. Interestingly, the primary ligand identified in activated platelets, thromboxane A synthase-1, is a key regulator of haemostasis via the arachidonic acid pathway. This contrasts with the major ligand in necrotic mammalian cancer cells, heat shock protein-90.

In current models of hemostasis, the platelet surface provides a link between primary haemostasis and the localisation of coagulation and fibrin formation. Without the latter, bleeding complications occur, as evidenced by patients with Scott syndrome, a platelet function defect characterised by the failure to externalise phosphatidylserine and hence, failure to provide a surface for prothrombinase. The thrombogram profile in a study of cyclosporine treated platelets by the inventors mimicked that seen in Scott syndrome platelets with a significant decrease in peak thrombin and a lesser decrease in endogenous thrombin potential. However, while there is agreement with regards the functional importance of the 'procoagulant' platelet phenotype, there remains much debate about its identity.

The inventors have discovered that arsenoxide compounds, such as GSAO, in conjunction with the α-granule marker, P-selectin, can identify a population of platelets with features of necrosis that have a functionally procoagulant phenotype. The GSAO+ population (i.e. the population capable of biding to GSAO) has properties of the coated platelet, including high fibrinogen binding, and sustained high level intracellular calcium, which is characteristic of SCIP platelets. In addition, GSAO+ platelets undergo cyclophilin D-dependent opening of the mitochondrial permeability transition pore, which are the platelets described by Jobe and colleagues (Jobe et al., 2008). The time course studies indicate that the appearance of the necrotic platelet occurs within a few seconds after agonist stimulation. Indeed, a transition from the activated platelet to the necrotic platelet was not apparent. This suggests that platelets going down the necrotic pathway are committed early after stimulation and less likely to be merely the end stage of prolonged exposure to strong agonists.

The formation of necrotic platelets within the developing thrombus has been visualized in real time in murine arterioles. The necrotic platelets are spatially associated with sites of fibrin formation in the platelet aggregate, which implies that they are providing a procoagulant surface during thrombus formation. Furthermore, not all agonists initiating formation of the platelet aggregate result in platelet necrosis. It is interesting that the model resulting in an occlusive thrombus was associated with platelet necrosis, while very few necrotic platelets were generated in the non-occlusive thrombus model. It may be that necrotic platelets tip the balance from haemostatic thrombus formation to pathological occlusive thrombosis.

The use of a cell death imaging agent that complexes with cytoplasmic ligands, such as GSAO, to identify the apoptotic/necrotic cells in vitro and in vivo has previously been described (Park et al., 2011; Park et al., 2013; Xie et al., 2013). The in vitro studies were performed exclusively using washed human platelets. Methods based on washed platelets are very useful for defining mechanisms in in vitro studies, however a number of factors reduces the utility of this method in translational research (population based studies). Firstly, to isolate platelets, a relatively large volume of blood is needed, which can be particularly problematic when studying small rodent species (models of disease). Secondly, the preparation of washed platelets is a labor-intensive and time-consuming process that involves multiple washing and centrifugation steps. Technical expertise and constant practice are required to prevent introduction of processing artefacts. In addition, in washed platelet-based assays platelets are studied in a non-physiological matrix, and in the absence of other plasma and cellular factors, which are known to modulate platelet responses.

For example, platelets and leukocytes, primarily neutrophils and monocytes, feature a number of well-defined adhesion molecules (P-selectin/P-selectin glycoprotein ligand 1, GPIbα/αMβ2) and soluble factors (PF4-RANTES, CD40L TXA2), which enable a productive two-way communication. The cross-talk between platelets and leukocytes is precisely regulated and facilitates platelet and neutrophil activation/adhesion important in inflammation, hemostasis and thrombosis. Dysregulation of platelet-leukocyte interactions has been implicated in vascular injury in atherothrombosis. Potential pathogenetic role of dysregulated platelet-leukocyte collaboration has also been described in a number of disease models including deep vein thrombosis, immune mediated vasculitis, sickle cell disease, inflammatory bowel disease, acute lung injury and sepsis.

In one embodiment, the present invention provides a method to detect a procoagulant platelet subpopulation in whole blood using a novel marker of cell death and a rapid, flow cytometry-based assay. A notable advantage of this method is that it can be performed using as little as 100 µL, of whole blood without the need for specific technical skills, making it ideal for gaining new insights into the role of procoagulant platelets in health and disease. An innovation of the method is the use of an arsenoxide (or arsenoxide equivalent) compound, which in conjunction with the α-granule marker, P-selectin, can identify a population of platelets with features of necrosis that have a functionally procoagulant phenotype. Furthermore, this assay replicates native conditions more closely where platelets can productively interact with leukocytes and other constituents of whole blood.

The whole blood platelet necrosis assay was validated by measuring formation of procoagulant platelets in response to well-known agonist in humans and mice. The assay was able to reproducibly measure platelet propensity to necrosis in healthy human volunteers as well as in patients with ischaemic heart disease within a clinical setting. Consistent with previous reports, dual stimulation with thrombin and collagen resulted in the largest procoagulant platelet subpopulation, however the magnitude of this subpopulation was increased in patients compared to healthy volunteers. Furthermore, treatment with aspirin did not affect the necrotic platelet propensity, while combined treatment with aspirin and a P2Y12 inhibitor resulted in a blunted necrotic propensity in coronary artery disease patients after thrombin or thrombin/collagen stimulation.

As proof of principle the ability of bacteria to induce platelet necrosis in whole blood ex vivo was investigated. A methicillin resistant *S. aureus* strain (USA 300) enhanced the formation of procoagulant platelet subpopulation in response to thrombotic stimuli. This observation is in keeping with epidemiological evidence of increased risk of thrombosis in sepsis, and may be mediated by FcγRIIA, which is a key to platelet aggregation in response to bacteria, as well as a factor in hypercoagulability associated with systemic lupus erythematosus.

Accordingly, the whole blood platelet necrosis assay using arsenoxide (or arsenoxide equivalent) compounds is a favorable tool for detecting necrotic, procoagulant platelets rapidly and reproducibly by flow cytometry. It offers unprecedented potential for widespread application in studying the role of platelets in cardiovascular disease, venous thromboembolism, and other prothrombotic states such as malignancy, sepsis and autoimmune disorders.

Further advantages of the flow cytometry-based assay for detection of platelet necrosis in whole blood (WBPN) include a dramatic reduction in the volume of blood required, improvement of throughput, and enablement of the study of the behavior of platelets and interactions between platelets and leukocytes within a physiological matrix. These improvements make it more feasible to investigate potential pathological roles of necrotic platelets in large-scale clinical setting and will permit repeated measurement of the same animal resulting in less variability and reduction in the number of animals sacrificed. The application of the technique to quantifying platelet propensity to necrosis in humans and mice in several settings including cardiovascular and infectious disease is also demonstrated.

Disclosed herein is a process for identifying procoagulant platelets, comprising contacting a platelet with a compound and determining whether the compound binds to the platelet, wherein the compound is an arsenoxide (or arsenoxide equivalent) compound. The platelet may be a necrotic platelet, for example a P-selectin+ platelet. The platelet may not be an apoptotic platelet.

Also disclosed herein is a process for identifying a patient at risk of developing a prothrombotic or thrombotic condition, comprising contacting a platelet from said patient with a compound and determining whether the compound binds to the platelet, wherein the compound is an arsenoxide (or arsenoxide equivalent) moiety. The platelet may be a necrotic platelet, for example a P-selectin+ platelet. The platelet may not be an apoptotic platelet.

Platelets positive for P-selectin expression can be identified using standard techniques in the art (e.g. FACS, immunohistochemistry, and the like).

Arsenoxide (or arsenoxide equivalent) compounds used in accordance with the present invention and uses thereof have been disclosed in WO 01/21628, WO 02/74305, WO 03/39564, WO 04/42079, WO 08/052279 and WO 09/43114, the entire contents of which are incorporated herein by cross-reference.

Compounds used in accordance with the invention may themselves be labelled with a reporter compound, including hydrophilic fluorophores, a biotin label or radioisotopes. For example, fluorescent labelled compounds can be used or a fluorophore can be attached to the compound. Examples of suitable fluorophores include fluorescein and Cy™5.5. Subcellular localisation of compounds can be detected by standard techniques including confocal fluorescence microscopy. Alternatively, compounds can be attached to other detectable groups, eg biotin, and detected by staining with streptavidin, such as Streptavidin-Alexa Fluor 488.

A compound used in accordance with the invention may be administered in an amount effective to detect the presence of procoagulant platelets using standard imaging techniques known to those in the art. For example, such imaging techniques may include: single-photon emission computed tomography (SPECT), positron emission tomography (PET) and magnetic resonance imaging (MRI).

In a preferred embodiment, a compound used in accordance with the invention is administered by intravenous injection.

In one embodiment, the absolute number of procoagulant platelets in a given volume of blood is determined. The number of procoagulant platelets in the given volume of blood may be compared to the other platelets in the given volume. The relative number of procoagulant platelets may be indicative of a prothrombotic or thrombotic condition.

Also disclosed herein is a process for identifying a compound which inhibits formation of procoagulant platelets, wherein said process comprises contacting a sample comprising platelets with a compound and determining whether the compound inhibits formation of procoagulant platelets.

Further disclosed herein is a process for screening a plurality of compounds to identify a compound which selectively inhibits formation of procoagulant platelets, wherein said process comprises contacting a sample comprising platelets with the plurality of compounds, determining whether any of the compounds inhibit formation of procoagulant platelets, and if so, separately determining for each of the plurality of compounds whether the compound inhibits formation of procoagulant platelets.

Monitoring inhibition of formation of procoagulant platelets can be done using standard techniques known to those in the art. For example, such imaging techniques may include: single-photon emission computed tomography (SPECT), positron emission tomography (PET) and magnetic resonance imaging (MRI).

The necrotic platelet has implications for potential therapeutic intervention in thrombotic diseases. Ex vivo analysis of platelets from human subjects on aspirin therapy indicates that procoagulant necrotic platelets form despite aspirin therapy, but their numbers are reduced by inhibition of the mitochondrial necrosis pathway.

Blocking the procoagulant platelet is attractive in thrombosis, as it would not affect the platelet aggregate required for haemostasis, and unlike systemic anticoagulant therapy, the effect would be localised to those lesions that are more likely to be pathological. For example, patients that have persistent ischaemic events on anti-platelet therapy may benefit. In addition, testing peripheral blood for propensity to generate necrotic platelets may be a useful biomarker for prediction of recurrent ischaemic events, particularly for patients already on aspirin therapy.

Prothrombotic or thrombotic conditions may be venous or arterial in nature. These conditions may occur in mammals, including humans.

Examples of prothrombotic or thrombotic conditions include: infection, sepsis, systemic inflammatory response syndrome, multi organ failure, thrombotic thrombocytopenia purpura, haemolytic uraemia syndrome, vascularisation, renal failure, ischaemic repercussion injury, solid organ transplant rejection, cardiovascular disease, stroke, venous thromboembolism, autoimmune disorders, sickle cell disease, inflammatory bowel disease, acute lung injury, malignancy, myocardial infarction (primary and secondary), embolic stroke, ischaemic stroke, thrombotic stroke, deep vein thrombosis (DVT), thromboembolism, portal vein thrombosis, renal vein thrombosis, jugular vein thrombosis, Budd-Chiari syndrome, Paget-Schroetter disease, cerebral venous sinus thrombosis, arterial thrombosis and arterial embolis.

The present invention may also find use in identifying compounds which prevent thrombosis formation in the following situations: artificial/prosthetic vascular shunts and grafts; coronary stenting; prosthetic heart valves; cardiopulmonary bypass procedures; haemoperfusion and haemodialysis; venous thromboembolic disease following surgery; peripheral arterial disease; percutaneous transluminal coronary angioplasty, during pregnancy; during immobilization; after carotid surgery; cerebrovascular accidents such as transient ischaemic; progression of atherosclerosis; ischaemic conditions.

Whilst the arsenoxide (or arsenoxide equivalent) compounds used in accordance with the processes of the present invention may be administered alone, it is generally preferable that the compound be administered as a pharmaceutical composition/formulation. In general pharmaceutical formulations may be prepared according to methods which are known to those of ordinary skill in the art and accordingly may include a pharmaceutically acceptable carrier, diluent and/or adjuvant.

The carriers, diluents and adjuvants must be "acceptable" in terms of being compatible with the other ingredients of the formulation, and not deleterious to the recipient thereof.

Single or multiple administration of the arsenoxide (or arsenoxide equivalent) compounds used in accordance with the invention, or pharmaceutical compositions comprising said compounds, can be carried out with dose levels and pattern being selected by a physician. Regardless, the compounds or pharmaceutical compositions used in accordance with the present invention should be administered so as to provide a quantity of the compound sufficient to identify and/or quantify the presence of procoagulant platelets.

One skilled in the art would be able, by routine experimentation, to determine an effective, non-toxic amount of the arsenoxide (or arsenoxide equivalent) compounds or pharmaceutical compositions used in accordance with the invention which would be required to identify and/or quantify procoagulant platelets. Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 $mg/m^2$. Generally, an effective dosage is expected to be in the range of about 25 to about 500 $mg/m^2$, preferably about 25 to about 350 $mg/m^2$, more preferably about 25 to about 300 $mg/m^2$, still more preferably about 25 to about 250 $mg/m^2$, even more preferably about 50 to about 250 $mg/m^2$, and still even more preferably about 75 to about 150 $mg/m^2$.

In relation to arsenoxide (or arsenoxide equivalent) compounds used in accordance with the processes of the present invention, an effective dosage is in the range of about 0.0001 mg to about 100 mg GSAO per kg body weight per 24 hours, preferably about 0.001 mg to about 100 mg GSAO per kg body weight per 24 hours, more preferably about 0.01 mg to about 50 mg GSAO per kg body weight per 24 hours, even more preferably about 0.1 mg to about 20 mg GSAO per kg body weight per 24 hours, even more preferably still about 0.1 mg to about 10 mg GSAO per kg body weight per 24 hours.

Further, it will be apparent to one of ordinary skill in the art that the optimal quantity and spacing of individual dosages of a compound used in a system of the present invention will be determined by the form, route and site of administration, and the nature of the patient. Also, such optimum conditions can be determined by conventional techniques.

Delayed release formulations are also included in the scope of the present invention.

Further, it will be apparent to one of ordinary skill in the art that the optimal quantity of a compound used in accordance with the present invention will be determined by the form, route and site of administration, and the nature of the particular patient. Also, such optimum conditions can be determined by conventional techniques.

Typically, salts of arsenoxide (or arsenoxide equivalent) compounds used in accordance with the processes of the present invention will be pharmaceutically acceptable salts; although other salts may be used in the preparation of the compound or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of the arsenoxide (or arsenoxide equivalent) compounds used in accordance with the processes of the present invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the arsenoxide (or arsenoxide equivalent) compounds used in accordance with the processes of the present invention therefore include acid addition salts.

For example, S. M. Berge et al. describe pharmaceutically acceptable salts in detail in *J. Pharmaceutical Sciences*, 1977, 66:1-19. The salts can be prepared in situ during the final isolation and purification of the arsenoxide (or arsenoxide equivalent) compounds used in accordance with the processes of the present invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Also included within the scope of compounds useful in the processes of the present invention are prodrugs. Typically, prodrugs will be functional derivatives of the compounds used in the present invention which are readily converted in vivo to the required (active) compounds as used in the processes of the invention as active agents, such as therapeutic and/or diagnostic agents. Typical procedures for the selection and preparation of prodrugs are known to those of skill in the art and are described, for instance, in H. Bundgaard (Ed), *Design of Prodrugs*, Elsevier, 1985.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, *arachis* oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The pharmaceutical compositions representing a component of the processes of the invention may be administered by standard routes. In general, the compositions may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. Still generally, the compositions representing a component of the process of the invention may be in the form of a capsule suitable for oral ingestion, in the form of an ointment, cream or lotion suitable for topical administration, in a form suitable for delivery as an eye drop, in an aerosol form suitable for administration by inhalation, such as by intranasal inhalation or oral inhalation.

For administration as an injectable solution or suspension, non-toxic parenterally acceptable diluents or carriers can include, Ringer's solution, isotonic saline, phosphate buffered saline, ethanol and 1,2-propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin.

In addition these oral formulations may contain suitable flavouring and colourings agents. When used in capsule form the capsules may be coated with compounds such as glyceryl monostearate or glyceryl distearate which delay disintegration of the capsule.

Adjuvants typically include emollients, emulsifiers, thickening agents, preservatives, bactericides and buffering agents.

Solid forms for oral administration may contain binders acceptable in pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate, and the like.

The emulsions for oral administration may further comprise one or more emulsifying agents. Suitable emulsifying agents include dispersing agents as exemplified above, or natural gums such as guar gum, gum acacia or gum tragacanth.

The compositions for parenteral administration will commonly comprise an arsenoxide (or arsenoxide equivalent) compounds used in accordance with the processes of the present invention or a cocktail thereof dissolved in an acceptable carrier, such as water, buffered water, 0.4% saline, and 0.3% glycine etc, wherein such solutions are sterile and relatively free of particulate matter.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The invention will now be described in greater detail by reference to specific Examples which should not be construed as in any way limiting the scope of the invention.

EXAMPLES

Example 1

Rationale for the Platelet Necrosis Marker

GSAO is a tripeptide trivalent arsenical that has recently been characterized as an imaging agent for necrotic and late apoptotic nucleated cells (Park et al., 2011; Park et al., 2013; Xie et al., 2013) (FIG. 1A). When tagged with a reporter compound at the γ-glutamyl residue of the glutathione moiety, the compound is unable to cross the intact plasma membrane. However, when plasma membrane permeability changes in necrosis or late apoptosis, GSAO enters the cell and is retained in the cytoplasm by covalent bonding to proteins containing closely spaced cysteine thiols (Park et al., 2011). The intracellular protein targets for trivalent arsenicals vastly outnumber the extracellular targets. For instance, the intensity of GSAO labeling of dying/dead nucleated cells is at least 1000-fold higher than labeling of viable cells (Park et al., 2011). The present inventors reasoned that GSAO might also selectively label the anucleate necrotic/apoptotic platelet.

GSAO marking of dying/dead nucleated cells is compatible with a number of different reporter groups, including hydrophilic fluorophores, a biotin label or radioisotopes (Park et al., 2011; Park et al., 2013; Xie et al., 2013). Conjugates of GSAO with AF647, AF546 or Oregon Green were employed in this study. A GSAO control compound, GSCA (4-(N—((S-glutathionyl) acetyl)amino)benzoic acid), contains an inert carboxylic acid group in place of the chemically reactive As(III) in GSAO. GSCA has the same biodistribution as GSAO but does not react with proteins so washes out of cells.

Example 2

GSAO Labels a Subpopulation of Activated Platelets

Calcium ionophore treatment of platelets leads to a sustained rise in intracellular calcium and surface elaboration of phosphatidylserine, which are features of both the procoagulant and necrotic phenotype (Bevers et al., 1982). Washed human platelets were treated with calcium ionophore and labeled with GSAO-AF647 and an antibody against the α-granule marker, P-selectin. GSAO-AF647 was consistently retained in a subpopulation of platelets that coexpress P-selectin (FIG. 1B). Resting platelets not exposed to ionophore did not label with GSAO-AF647. The control compound, GSCA-AF647, showed no labeling of ionophore treated platelets.

Dual stimulation with thrombin and collagen is known to be superior to either agonist alone in the generation of the procoagulant platelet (Schoenwaelder et al., 2009; Jobe et al., 2008; Fager et al., 2010). To determine whether GSAO labeling reflects this agonist profile, washed human platelets were stimulated with thrombin, collagen, or both thrombin and collagen. Thrombin generated minimal GSAO+ platelets, collagen stimulation resulted in a moderate proportion, while simultaneous stimulation with thrombin and collagen resulted in a marked increase in GSAO+ platelets (FIGS. 1C and D). To determine if signalling through the collagen receptor, GPVI, was sufficient to generate the GSAO+ phenotype, the maximal proportion of GSAO+ platelets generated by collagen was compared with the GPVI specific activator, collagen related peptide. The majority of the collagen effect was recapitulated with the peptide (FIG. 1E).

Example 3

Figure 2:
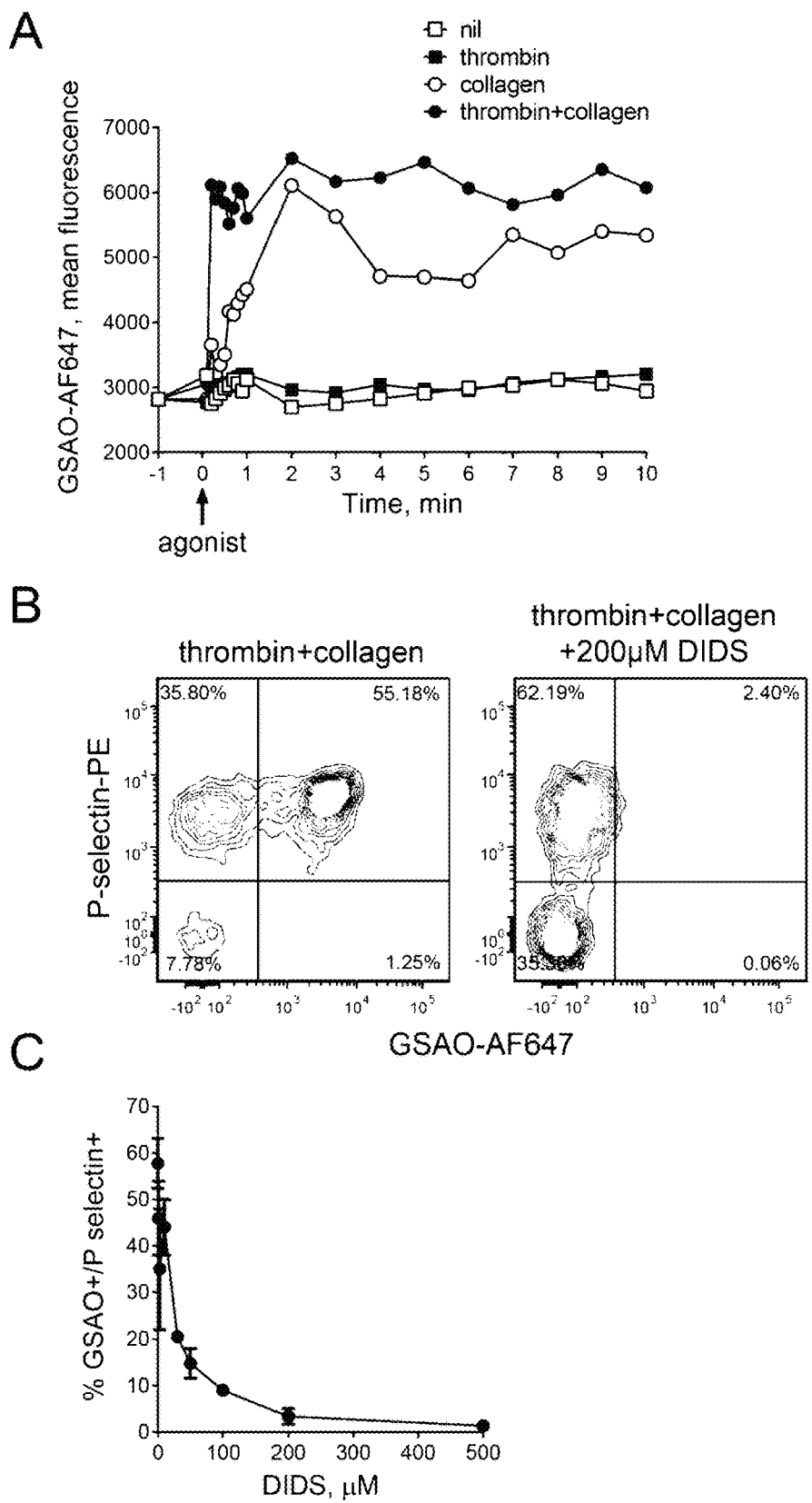
FIG. 2. GSAO rapidly enters the activated platelet subpopulation via an organic anion-transporting polypeptide. A. The kinetics of labeling of stimulated platelets with GSAO-AF647 was measured by time lapse flow cytometry. Flow plots are representative of n≥3 separate experiments, and bars and data points are from n≥3 separate experiments. *p<0.05, ****p<0.0001. B-C. Washed human platelets were stimulated with thrombin (0.1 units/mL) and collagen (5 µg/mL), incubated with 0-200 µM DIDS for 10 min, then exposure of P-selectin and labeling with GSAO-AF647 measured by flow cytometry. DIDS inhibited GSAO labelling of P-selectin+ activated platelets at a half-maximal concentration of ~30 µM. The data points and errors are the mean±range of 1-5 experiments.
Figure 3:
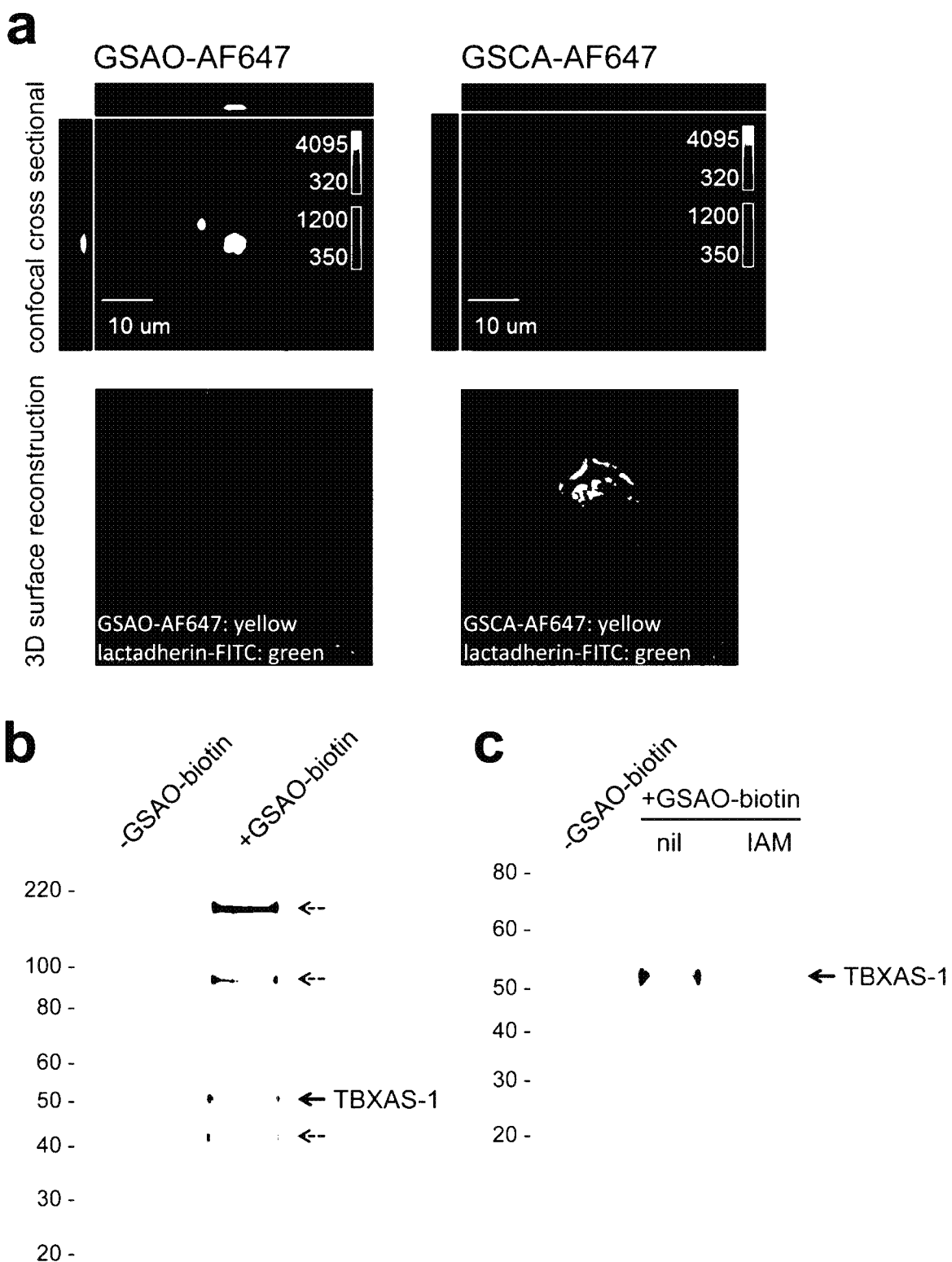
FIG. 3. GSAO concentrates in the cytoplasm of necrotic platelets complexed to thromboxane A synthase-1. A. Washed human platelets on collagen-coated coverslips were treated with thrombin (0.1 units/mL), washed, fixed and stained with GSAO-AF647, control GSCA-647 and lactadherin-FITC. The upper panels are orthogonal cross-sectional views of the platelets collected by confocal microscopy using a water dipping lens. Lactadherin (green) binding reflects phosphatidylserine externalization. GSAO-AF647 (yellow) is retained within the intracellular compartment, but not on the spread membrane surface. There is no labeling of platelets with control GSCA-AF647. The bottom panels are 3D reconstructions of lactadherin-positive spreading platelets showing the accumulation of GSAO-AF647 in the central cytoplasm. B. Thrombin and collagen stimulated platelets were incubated without or with GSAO-biotin. The labeled proteins were collected with streptavidin-coated beads, eluted with 2,3-dimercaptopropanol, resolved on SDS-PAGE and stained with Sypro Ruby. The major specific band was identified as thromboxane A synthase-1 (TBXAS-1) by mass spectrometry. The bands indicated by dashed arrows were also pulled down in the absence of GSAO-biotin. The positions of $M_r$ markers are indicated at left. C. Purified TBXAS-1 was incubated without and with GSAO-biotin and complex formation measured by blotting with streptavidin-peroxidase. To confirm thiol-dependent reaction of GSAO with TBXAS-1, the protein was incubated with the thiol alkylator, iodoacetamide (IAM), before labeling with GSAO-biotin. The positions of $M_r$ markers are indicated at left.

GSAO Rapidly Enters the Activated Platelet Subpopulation Via an Organic Anion-transporting Polypeptide The rate of GSAO+ platelet generation after agonist exposure was measured using time lapse flow cytometry. Results are reported for GSAO+ events based on lead in time prior to agonist exposure threshold. Resting platelets showed no increase in GSAO labeling over 10 min. Platelets exposed to thrombin demonstrate little GSAO labeling compared with unstimulated platelets. Collagen alone resulted in a gradual increase in GSAO labeling over 60 sec, while combination thrombin and collagen stimulation resulted in a rapid initial rise in GSAO labeling that peaked in 12 sec and was sustained over the 10 min of the experiment (FIG. 2A).

The organic anion-transporting polypeptide (OATP) family has been implicated in transport across the plasma membrane of organic anions in the same class as GSAO (Dilda et al., 2009; Dilda et al., 2008). Nine members of the OATP family have been reported in humans (Hagenbuch et al., 2003) and platelets express OATP2B1 (Niessen et al., 2009). DIDS is an inhibitor of OATP class B transporters (Kobayashi et al. 2003) and the present inventors tested its effect on GSAO labelling of agonist-stimulated platelets. DIDS inhibited GSAO labelling of P-selectin+ activated platelets (FIG. 2B) at a half-maximal concentration of ~30 μM (FIG. 2C). GSAO is retained in the platelet cytoplasm through covalent reaction with closely-spaced protein cysteine thiols (Park et al., 2011) (data not shown).

Example 4

Figure 4:
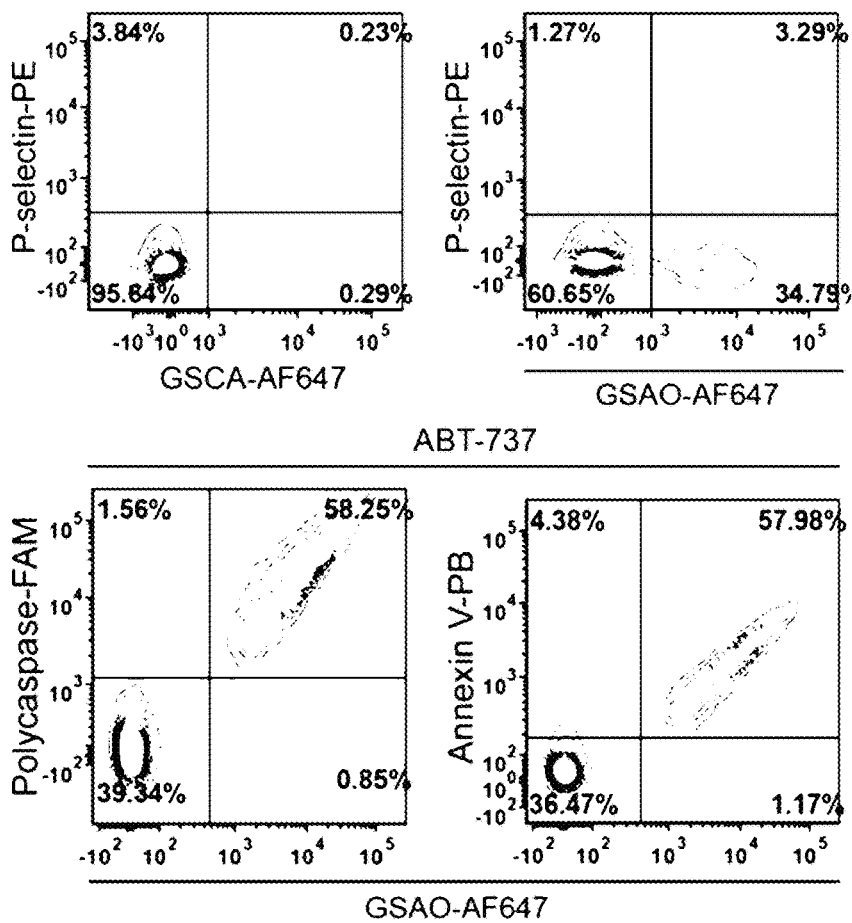
FIG. 4. Labeling with GSAO and exposure of P-selectin distinguishes necrotic from apoptotic platelets. A. Washed human platelets were incubated with 30 µM of the BH3 mimetic ABT-737 for 2 h and exposure of P-selectin and labeling with GSAO-AF647, control GSCA-AF647, polycaspase-FAM or annexin V-PB was measured by flow cytometry. B. Washed human platelets were incubated with increasing concentrations of ABT-737 for 2 h and labeling with GSAO-AF647 and exposure P-selection measured by flow cytometry. The percentage of GSAO+ platelets are graphed with respect to P-selectin exposure. C. Washed human platelets were preincubated with 200 µM of ZVAD-FMK or vehicle control for 15 min then incubated with 30 µM of ABT-737 for 2 h (part F), or stimulated with thrombin (0.1 units/mL) and collagen (5 µg/mL) for 10 min (part G). Labeling with GSAO-AF647 and exposure of P-selection was measured by flow cytometry. D. Washed human platelets from healthy donors (n=5-11) were untreated or stimulated with thrombin (0.1 units/mL), collagen (5 µg/mL), or thrombin (0.1 units/mL) and collagen (5 µg/mL) for 10 min. Labeling with GSAO-AF647 and exposure of P-selection was measured by flow cytometry and the results expressed as GSAO+ platelets that are P-selectin– or P-selection+. The error bars are mean±SD.
Figure 4:
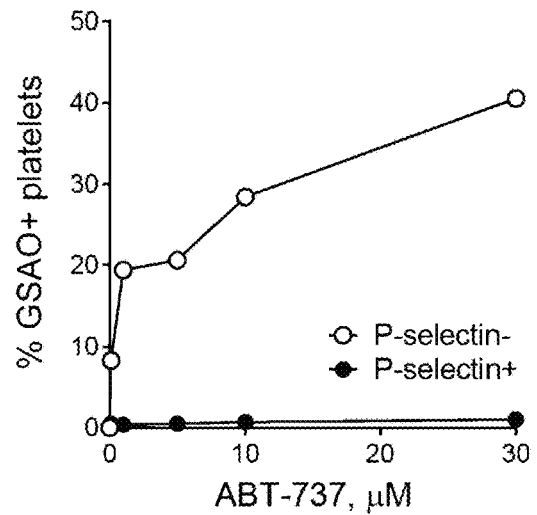
Figure 4:
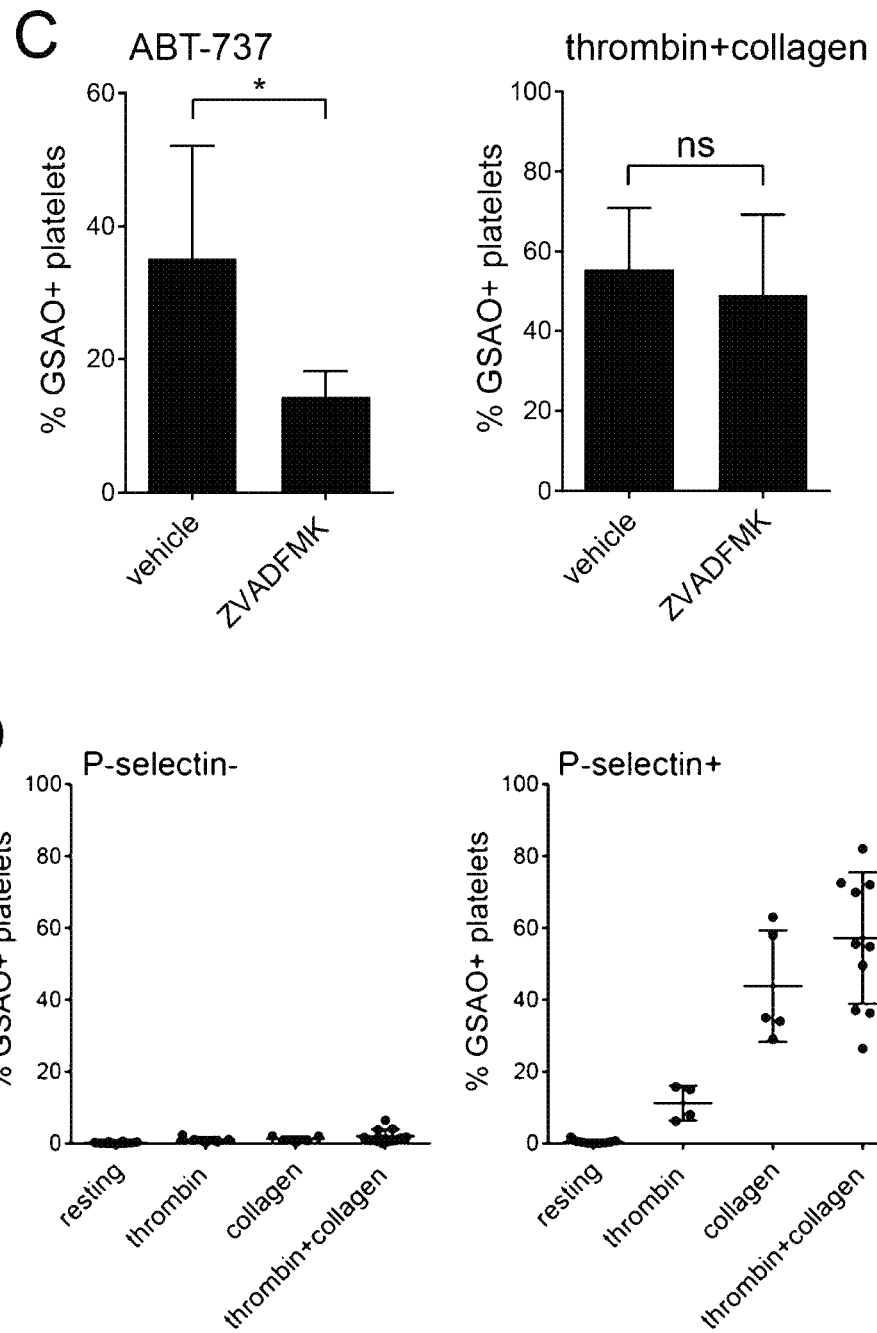

Labeling with GSAO and Exposure of P-selectin Distinguishes Necrotic from Apoptotic Platelets Bcl-$X_L$ dependent apoptosis is involved in regulation of platelet life span, although the role of platelet apoptosis in thrombosis is controversial. In order to determine if GSAO can differentiate agonist-induced necrotic versus apoptotic platelets, platelet apoptosis was triggered using the BH3 mimetic ABT-737. GSAO labelled P-selectin negative apoptotic platelets (FIGS. 4A and B). The GSAO+ population also labeled with a polycaspase marker and annexin V, both indicators of apoptotic cells. The pancaspase inhibitor, ZVADFMK, reduced ABT-737 induced GSAO+/P-selectin– platelets but had no effect on GSAO labeling of thrombin and collagen stimulated platelets (FIG. 4C), confirming that the agonist induced platelets are not undergoing apoptotic cell death. These results indicate that apoptotic platelets are GSAO+/P-selectin–, while necrotic platelets are GSAO+/P-selectin+(See Example 5). Washed platelets from healthy donors were untreated or stimulated with thrombin, collagen or thrombin and collagen and examined for apoptosis (GSAO+/P-selectin–) and necrosis (GSAO+/P-selectin+) (FIG. 4D). These agonists trigger platelet necrosis but not apoptosis.

Example 5

GSAO+/P-Selectin+ Procoagulant Platelets have Features Consistent with Cyclophilin D-Dependent Regulated Necrosis, not Apoptosis

| Features | Apoptosis | Necrosis | GSAO+/P-selectin+ platelet |
|---|---|---|---|
| Membrane integrity | Intact in early stages and loss in late stages | Early loss of membrane integrity | Loss of membrane integrity |
| Initiating stimulus | Ratio of Bcl-$X_L$ expression levels | External ligands | Physiological agonists |
| Structural morphology | Shrinkage and microparticle blebbing | Cellular swelling | Cellular swelling |
| Phosphatidylserine exposure | Present | Present | Present |
| Effect of calcium chelation | No inhibition | Inhibition | Inhibition |
| Active caspases | Dependent on execution of caspases | Not dependent on caspases, but may be present | Not dependent on caspases, but may be present |
| Formation of mPTP | Not characteristic | An early event | An early event |
| Loss of $\Delta\psi_m$ | A late event | An early event | An early event |
| Genetic ablation of factors | Bax/Bak knockout | CypD knockout RIP3 knockout | CypD knockout |
| Drug inhibition | Caspase inhibitors | Cyclosporine A | Cyclosporine A |

Example 6

Figure 5:
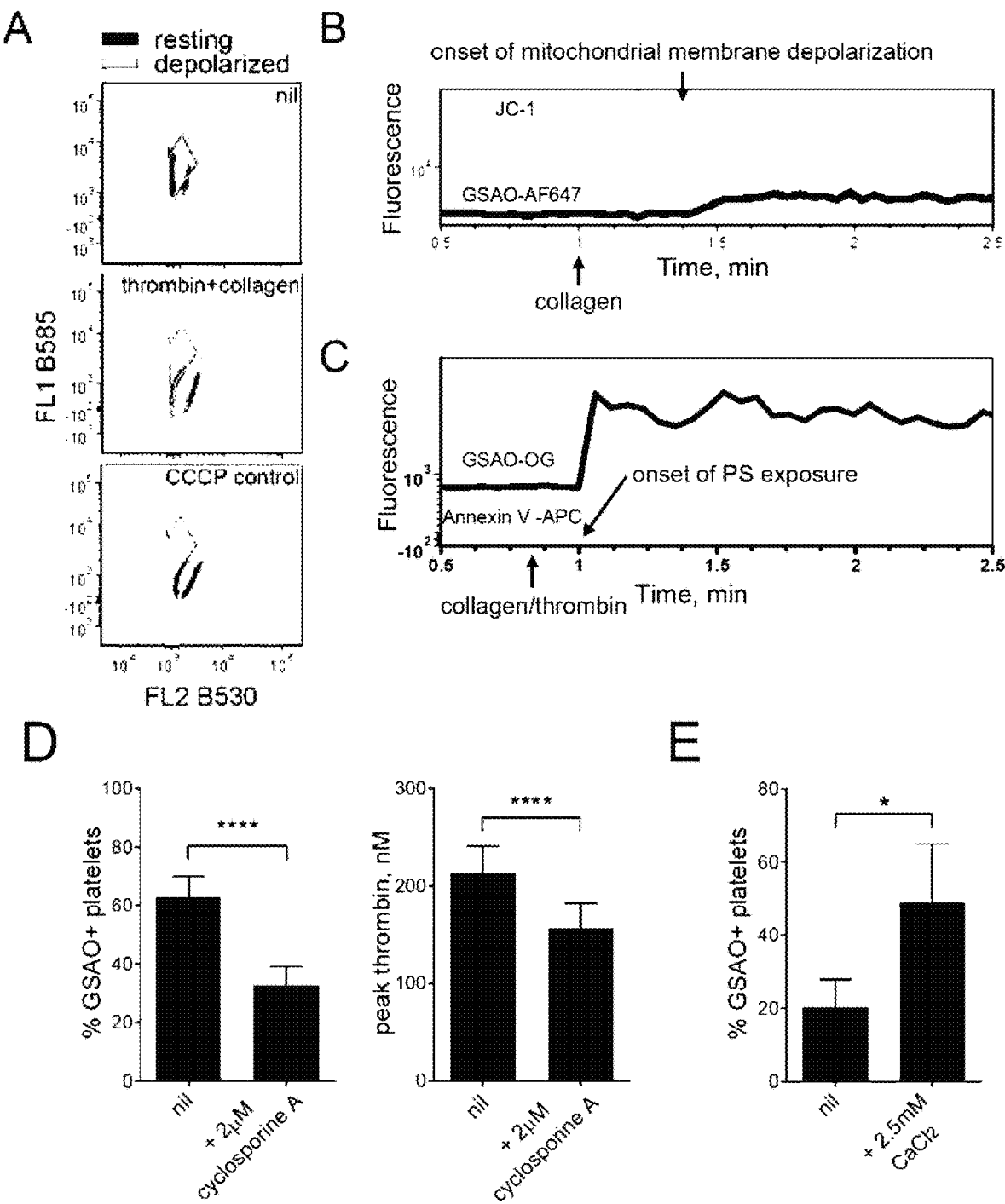
FIG. 5. GSAO marks platelets undergoing cyclophilin D-dependent necrosis. A. Washed human platelets were untreated or stimulated with thrombin (0.1 units/mL) and collagen (5 µg/mL) or the mitochondrial membrane disrupter CCCP (4 µM). Mitochondrial transmembrane potential was measured using the cationic dye, JC-1. The ratio of distribution of JC-1 between the mitochondria (red fluorescence) and cytosol (green fluorescence) reflects mitochondrial transmembrane potential. Results are representative of n≥3 separate experiments. B-C. The correlation between loss of platelet mitochondrial transmembrane potential (JC-1 loss of B585 fluorescence) or phosphatidylserine exposure (annexin V labeling) and labeling with GSAO-AF647 after collagen (5 µg/mL) or thrombin (0.1 units/mL) and collagen (5 µg/mL) stimulation was measured by time lapse flow cytometry. D. Washed human platelets were untreated or preincubated with the cyclophilin D inhibitor, cyclosporine A (CysA, 2 µM), for 15 min prior to stimulation with thrombin (0.1 units/mL) and collagen (5 µg/mL). Labeling with GSAO-AF647 was measured by flow cytometry and procoagulant potential assessed using the Calibrated Automated Thrombogram (n=3-6, ****p<0.0001). E. Washed human platelets were preincubated with $CaCl_2$ for 15 min and then untreated or stimulated with thrombin (0.1 units/mL) and collagen (5 µg/mL). Labeling with GSAO-AF647 was measured by flow cytometry (n=8, *p<0.05).
Figure 9:
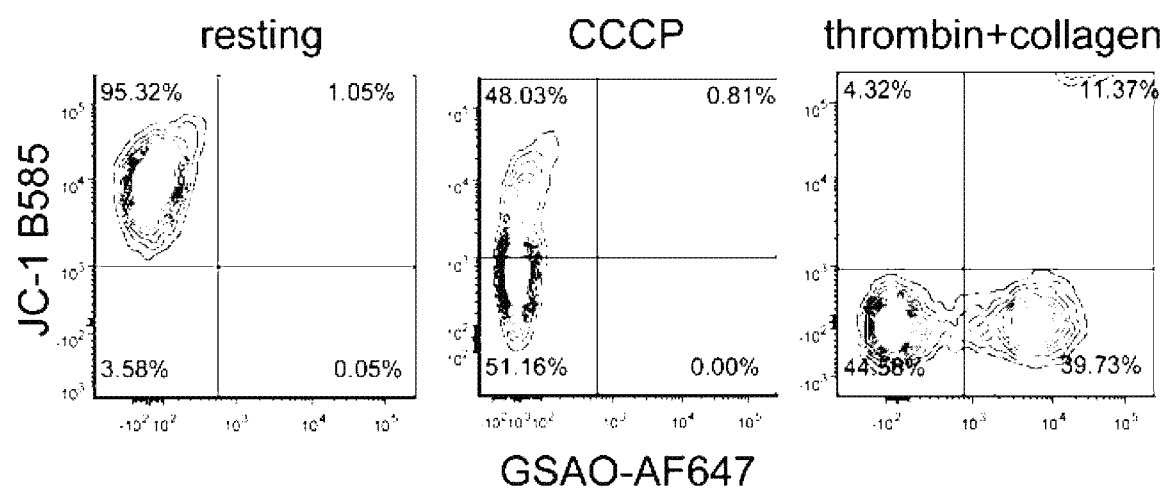
FIG. 9. Mitochondrial membrane disruption is not sufficient for GSAO labeling. Washed human platelets were left unstimulated, treated with CCCP (4 µM) or stimulated with thrombin (0.1 units/mL) and collagen (5 µg/mL), and loss of platelet mitochondrial transmembrane potential (JC-1 loss of B585 fluorescence) and labeling with GSAO-AF647 measured by flow cytometry.

GSAO+/Pselectin+ Marks Platelets Undergoing Cyclophilin D-dependent Necrosis The cyclophilin D-dependent regulated necrosis pathway is characterized by agonist stimulation, raised intracellular calcium, formation of the mitochondrial transition pore and loss of mitochondrial membrane potential. Dual agonist stimulation of platelets results in loss of mitochondrial transmembrane potential (FIG. 5A). The onset of mitochondrial depolarisation (FIG. 5B) and phosphatidylserine exposure (FIG. 5C) are coincident with GSAO labeling. Direct mitochondrial membrane depolarization using m-chlorophenylhydrazone (CCCP) does not result in GSAO labelling, indicating that GSAO entry into necrotic platelets is not triggered by direct mitochondrial perturbation (FIG. 9).

Figure 6:
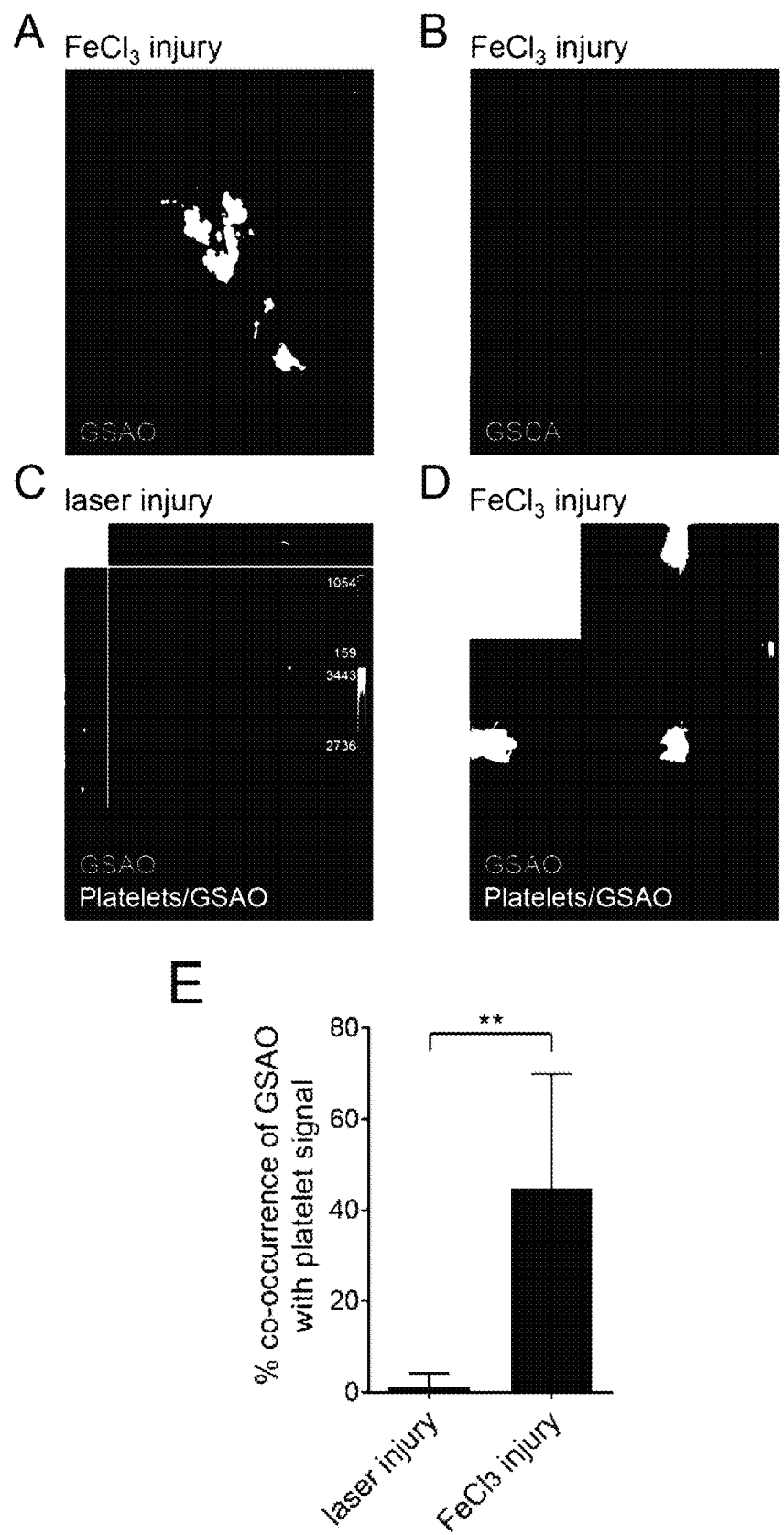
FIG. 6. GSAO+ platelets form in occluding murine thrombi and are attenuated with megakaryocyte directed deletion of the cyclophilin D gene. A-B. Dylight 649-conjugated anti-platelet CD42b antibody and GSAO-Oregon Green or control compound GSCA-Oregon green were injected into the murine circulation and thrombus initiated in the cremaster muscle arterioles by $FeCl_3$. Thrombi were captured by confocal intravital video microscopy and images are displayed as 3D reconstructions (maximum intensity projection mode). Occlusive thrombi incorporate GSAO-Oregon green, but not the control compound. C-E. Dylight 649-conjugated anti-platelet CD42b and GSAO-Oregon Green were injected into the murine circulation and thrombus initiated in the cremaster muscle arterioles by either laser (part C) or $FeCl_3$ (part D) injury. Thrombi were captured by confocal intravital video microscopy and images displayed as cross-sectional orthogonal views for single plane colocalization. There was minimal GSAO signal in the non-occlusive thrombus initiated by laser injury, but extensive signal in the occlusive thrombus initiated by $FeCl_3$ injury (part C, n=6-8 in 6-8 different mice, Manders correlation co-efficient, **p<0.01). F. Dylight 649-conjugated anti-platelet CD42b antibody, GSAO-AF546 and AF488-conjugated anti-fibrin antibody were injected into the murine circulation of wild-type (WT) or platelet-specific cyclophilin D-deficient (PF4Cre+CypD$^{F1/F1}$) mice and thrombus initiated in the cremaster muscle arterioles by $FeCl_3$ injury. Thrombi were captured by confocal intravital video microscopy and images analyzed for integrated GSAO, platelet and fibrin fluorescence (WT n=4, 29 thrombi; PF4Cre+CypD$^{F1/F1}$ n=3, 15 thrombi; *p<0.05, **p<0.001). G. Dylight 649-conjugated anti-platelet CD42b antibody, GSAO-Oregon Green and calcium sensing dye rhodamine 2 were injected into the murine circulation and thrombus initiated in the cremaster muscle arterioles by $FeCl_3$ injury. Thrombus was visualized 10 min after injury. Images are represented as cross-sectional orthogonal views of single confocal plane displaying platelets and GSAO (left) with rhodamine signal (right). Persistence of high calcium signal is demonstrated in the GSAO+ platelets consistent with necrotic cell death.
Figure 6:
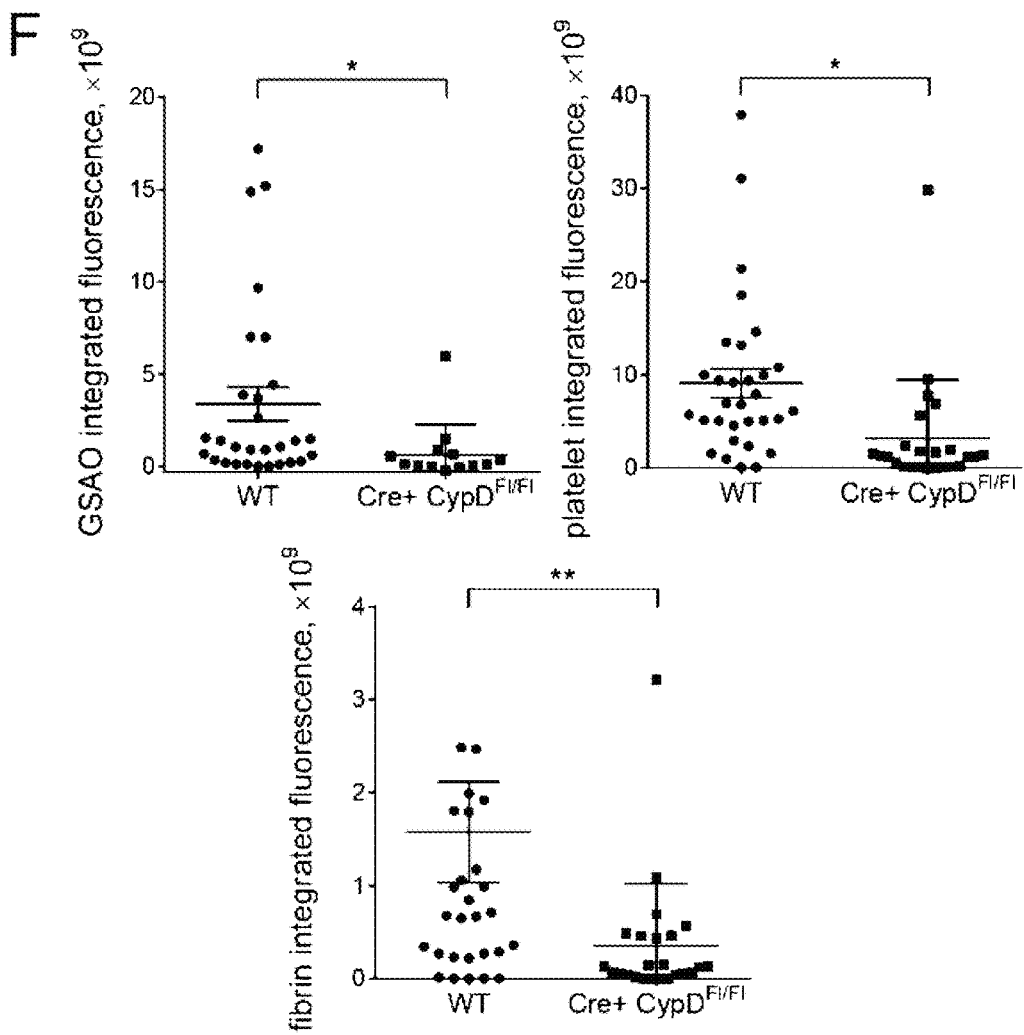
Figure 6:
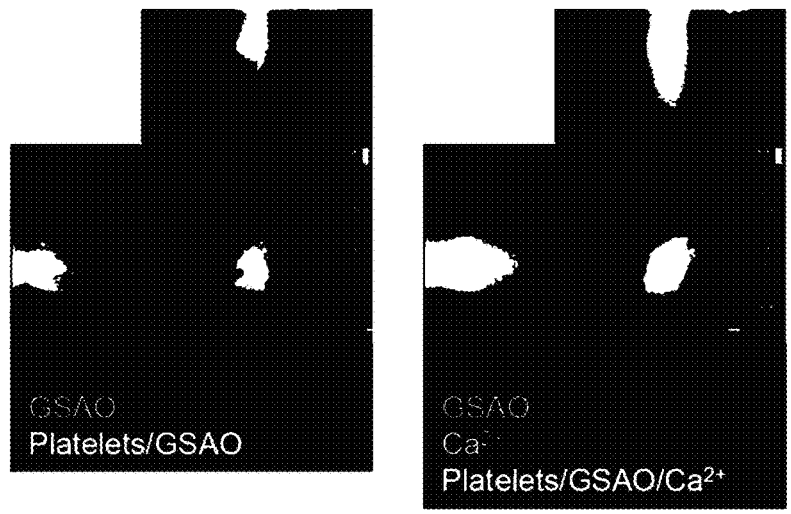

Cyclophilin D is involved in formation of the mitochondrial permeability transition pore, and inhibition of this protein blunts pore formation and necrosis (Nakagawa et al., 2005). Inhibiting cyclophilin D with cyclosporine A reduced GSAO labeling and procoagulant potential of agonist stimulated platelets (FIG. 5D). Increases in cytosolic calcium levels are an important event in cell necrosis, leading to a chain of molecular events resulting in bioenergetics failure (McCormack et al., 1990). As anticipated, addition of calcium promoted GSAO+ agonist stimulated platelets (FIG. 6F).

Example 7

Figure 10:
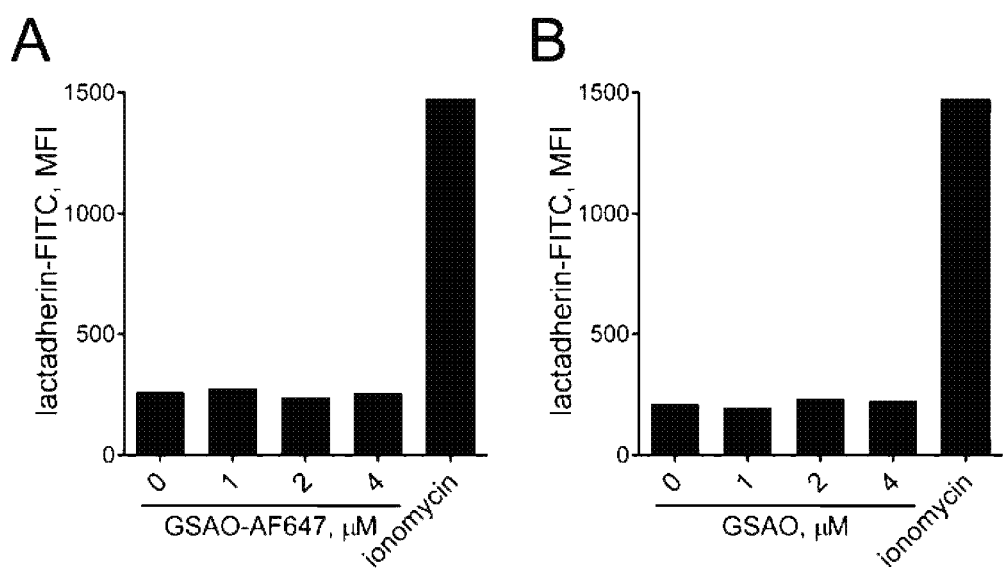
FIG. 10. GSAO alone does not trigger platelet apoptosis or necrosis. Washed human platelets were incubated with up to 4 µM labeled GSAO (part A) or unconjugated GSAO (part B) or 10 µM ionomycin for 10 min, washed, incubated with 0.1 µM lactadherin-FITC and analysed by flow cytometry. There was no GSAO-mediated increase in phosphatidylserine exposure in the platelets, which is a surrogate marker for apoptosis and necrosis. The maximum concentration of labeled GSAO used in the platelet studies was 1 µM.

GSAO+ Platelets Form in Occluding Murine Thrombi and are Attenuated with Megakaryocyte Directed Deletion of the Cyclophilin D Gene It is important that GSAO not interfere with thrombus formation for it to be used as an in vivo marker of procoagulant necrotic platelets. GSAO-AF647 or unconjugated GSAO does not trigger platelet apoptosis or necrosis (FIG. 10). GSAO-Oregon Green (1 µM) also had no effect on in vitro platelet aggregation in response to collagen, thrombin, ADP or epinephrine, and there was no effect on coagulation in a one-step clotting assay (data not shown). GSAO-AF750 (0.1 µg/g mouse) had no effect on platelet accumulation or fibrin formation in the murine laser injury model of thrombosis (data not shown).

Two methods of initiation of thrombosis in the murine cremaster arteriolar circulation were compared and contrasted to explore the functional relevance of GSAO+ platelets in vivo: (i) the endothelial stimulation laser injury model that is primarily dependent on thrombin for thrombus formation and not dependent on extravascular collagen exposure (Falati et al., 2002; Dubois et al., 2007), and (ii) the FeCl$_3$ chemical injury model (Dubois et al., 2006). Dylight-conjugated anti-platelet CD42b antibody, GSAO-Oregon Green, GSAO-AF546, GSAO-AF647 or appropriately labelled control compound GSCA were introduced to the murine circulation and arterioles injured and thrombi imaged within 10-30 min. Thrombus formation was imaged in real time by three laser confocal microscopy and 2D orthogonal sections and 3D-high resolution images were reconstructed. GSAO-AF750 is detectable in the murine circulation up to 3 h after intravenous injection and persists within necrotic lesions for at least 6 h (Xie et al., 2013), so thrombi are imaged well before GSAO is cleared from the circulation. A 3000 Da dextran tracer has been shown to permeate the shell and core of laser-induced platelet thrombi (Vonorov et al., 2013; Stalker et al., 2013). GSAO-fluorophore has a molecular mass of ~1500 Da and is expected to readily diffuse within thrombi.

Figure 11:
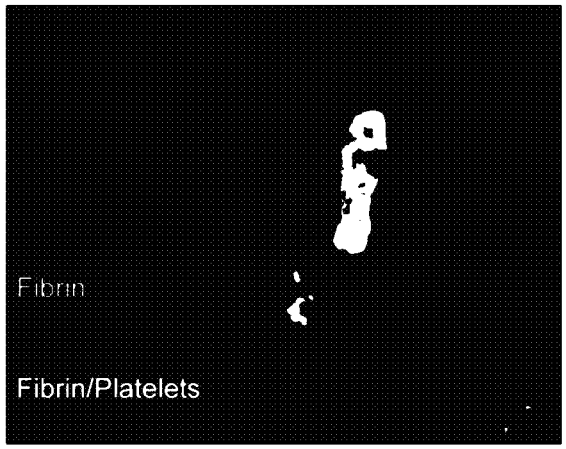
FIG. 11. Cyclophilin D deletion in platelets results in reduction in thrombus and fibrin formation. Dylight 649-conjugated anti-platelet CD42b antibody, GSAO-AF546 and AF488-conjugated anti-fibrin antibody were injected into the murine circulation of Cre-CypD$^{F1/F1}$ or Cre+CypD$^{F1/F1}$ mice and thrombus initiated in the cremaster muscle arterioles by $FeCl_3$ injury. Thrombi were captured by confocal intravital video microscopy and images are displayed as 3D reconstructions (maximum intensity projection mode).
Figure 11:
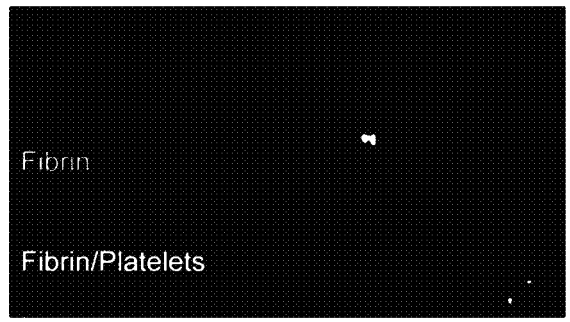

GSAO-Oregon Green labelled a subset of platelets within thrombi induced by FeCl$_3$ injury (FIG. 6A), while control GSCA-Oregon Green was not retained (FIG. 6B). There were minimal GSAO+ platelets in the non-occluding thrombi induced by laser injury (FIG. 6C). Approximately 1% of the platelet signal in the laser injury model co-occurred with the GSAO signal, compared to 44% in the occlusive platelet aggregates of the FeCl$_3$ injury model (range 11%-80%) (FIGS. 6D and E). There were reduced GSAO+ platelets in thrombi initiated by FeCl$_3$ injury in cyclophilin D-deficient mice, which associated with reduced platelets and fibrin (FIG. 6F and FIG. 11). GSAO+ platelets were also characterized by high intracellular calcium levels, which is consistent with necrosis (FIG. 6G).

Example 8

GSAO Marks Functionally Procoagulant Platelets

The relationship between the activated and procoagulant phenotype of platelets remains controversial (Dale et al., 2002; Abaeva et al., 2013). Procoagulant platelets are characterised by presence of phosphatidylserine on the platelet surface, surface binding of plasma derived activated clotting factors, ability to generate thrombin and promotion of fibrin formation. Regardless of the agonist stimulus, 100% of GSAO+ platelets were positive for α-granule P-selectin, which implies that α-granule release is a prerequisite for GSAO labeling after agonist stimulation (FIG. 1). Effectively all GSAO+ platelets bound annexin V indicating externalisation of phosphatidlyserine (FIGS. 7A & B), which is a hallmark of necrosis (Bratosin et al., 2005). Of note, a subpopulation of GSAO− platelets also bound annexin V so platelet necrosis is not required for exposure of phosphatidylserine.

Figure 7:
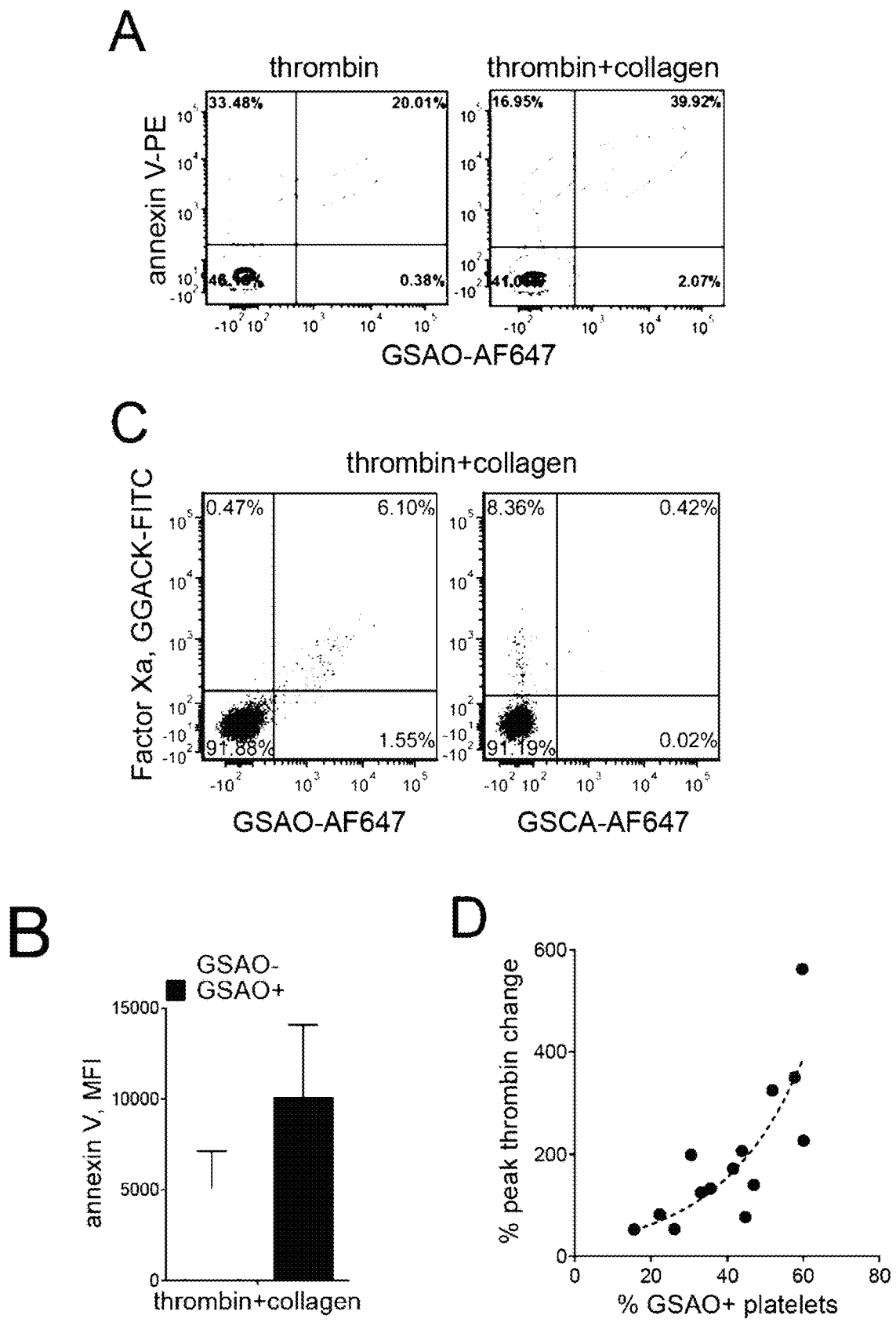
FIG. 7. GSAO marks functionally procoagulant platelets. A-B. Washed human platelets were stimulated with thrombin (0.1 units/mL) or thrombin (0.1 units/mL) and collagen (5 µg/mL) and phosphatidylserine externalization was assessed by annexin V binding. The mean fluorescence intensity of annexin V binding to GSAO- and GSAO+ platelets is shown in part B. Flow plots and bars are representative of n≥3 separate experiments. C. Platelet rich plasma was recalcified and stimulated with thrombin (1 units/mL) and collagen (5 µg/mL) with fibrin polymerization inhibition. FXa on the platelet surface was detected using the small molecule inhibitor, GGACK-FITC. 93% of the FXa+ platelets co-labeled with GSAO. D. Washed human platelets were stimulated with thrombin (0.1 units/mL) or thrombin (0.1 units/mL) and collagen (5 µg/mL) and their procoagulant potential assessed using the Calibrated Automated Thrombogram. Correlation between peak thrombin time and the percentage of GSAO+ positive platelets in the preparation (n=18). The dotted line is the non-linear least squares fit of the data to a single exponential ($r^2$=0.77, p<0.001). E. Dylight 649-conjugated anti-platelet CD42b antibody, GSAO-AF546 and AF488-conjugated anti-fibrin antibody were injected into the murine circulation and thrombus initiated in the cremaster muscle arterioles by $FeCl_3$ injury. Images are represented as cross-sectional orthogonal views of single confocal plane separately displaying GSAO and fibrin signal (left) and platelet signal (right). Fibrin signal preferentially localized with the GSAO+ platelets (representative image, n=9 images in 3 independent mice). F. 3D reconstruction of an occlusive thrombus.
Figure 7:
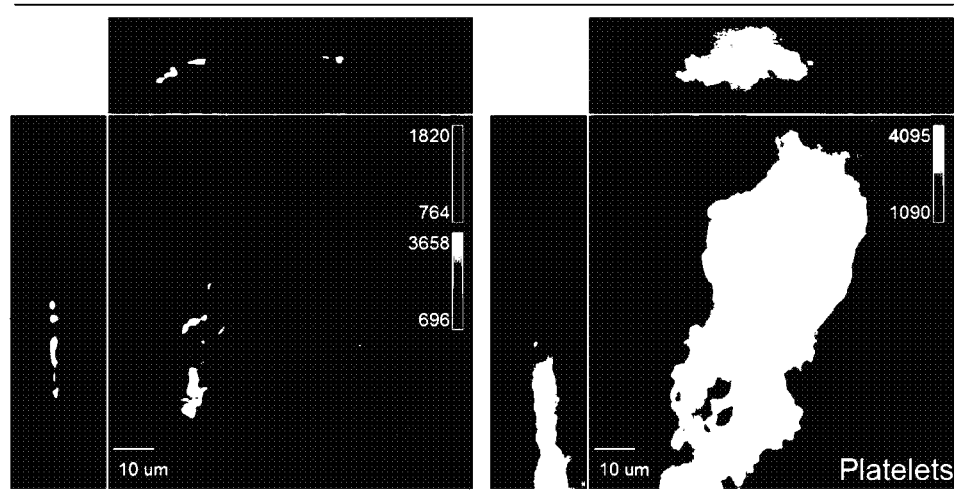
Figure 7:
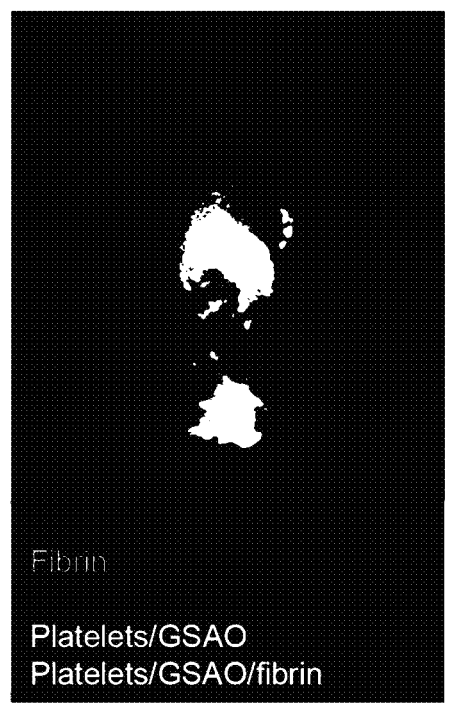

The synthetic covalent inhibitor of Factor Xa (FXa), FITC-labeled Glu-Gly-Arg chloromethyl ketone (GGACK-FITC), was used to detect this activated coagulation factor on the platelet surface. There was a high correlation ($\chi^2=15793$, $p<0.000$) between GSAO labeling and FXa on the agonist-activated platelet surface (FIG. 7C). The sensitivity and specificity for detection of FXa on the platelet surface by GSAO labeling is 99% and 91%, respectively. To assess the functional procoagulant potential of the GSAO+ agonist stimulated platelets, peak thrombin values were measured using the global coagulation assay, Calibrated Automated Thrombogram. There was an exponential correlation between the percentage change in peak thrombin and percentage change in GSAO+ platelets (FIG. 7D). These results demonstrate that GSAO+ necrotic platelets are functionally procoagulant.

To determine if GSAO+ platelets support coagulation in vivo, the present inventors looked for localization of GSAO+ platelets with fibrin within thrombi induced by $FeCl_3$ injury in murine cremaster arterioles. Fibrin is the end product of activation of the coagulation factors. Fibrin strands are shown adjacent to GSAO+ platelets in the 2D cross sectional sections (FIG. 7E). The triple localization of platelets, GSAO and fibrin is demonstrated by the white in the 3D reconstruction of an occlusive thrombus (FIG. 7F and Examples 10-15). These findings demonstrate that GSAO identifies procoagulant platelets in vitro and in vivo. Together, these results demonstrate that the GSAO+ platelets generated during thrombus formation form via the cyclophilin D-dependent necrosis pathway and are procoagulant.

Example 9

Figure 8:
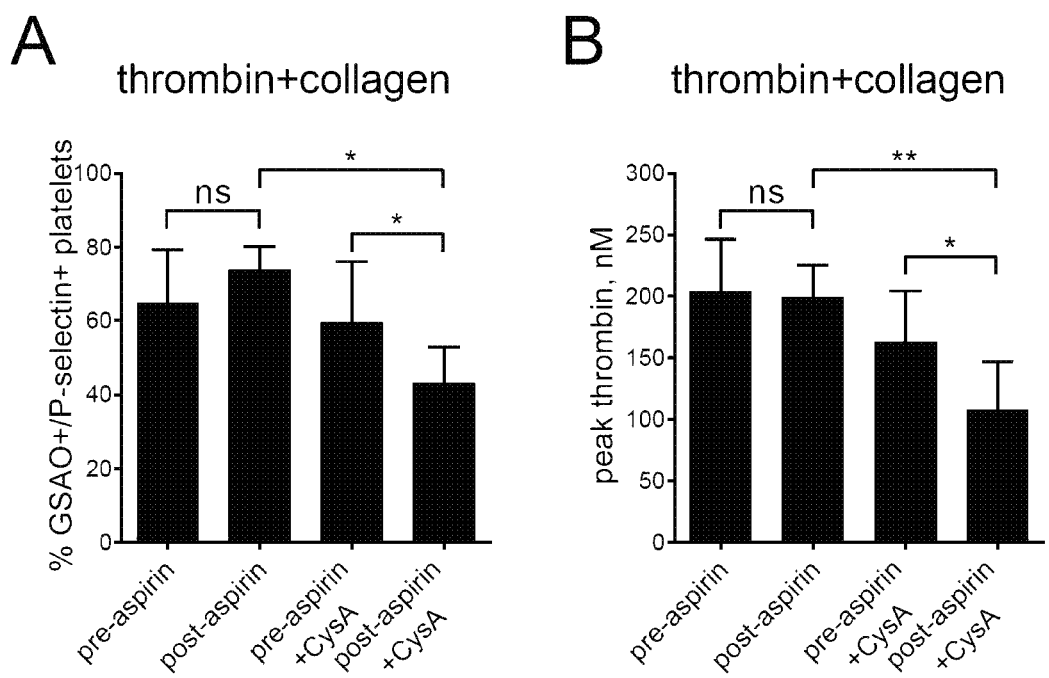
FIG. 8. Aspirin ingestion sensitizes platelets to cyclophilin D inhibition in human subjects. Platelets from healthy volunteers were examined before and after 7 days of aspirin ingestion. Washed platelets were activated with thrombin (0.1 units/mL) and collagen (5 µg/mL) and GSAO+/P-selectin+ necrotic platelets measured by flow cytometry (part A) and procoagulant potential assessed using the Calibrated Automated Thrombogram (part B). Aspirin ingestion resulted in no change in the GSAO+/P-selectin+ necrotic or procoagulant potential of activated platelets. CysA treatment of pre-aspirin platelets resulted in decrease in GSAO+/P-selectin+ necrotic platelets (n=5,* p<0.05) and procoagulant function (n=5, **p<0.01), and this effect was more pronounced in the post-aspirin platelets (n=5,* p<0.05).

Aspirin Ingestion Sensitizes Platelets to Cyclophilin D Inhibition in Human Subjects The standard pharmacological means for prevention of cardiovascular events is by inhibiting platelet cyclooxygenase-1 with aspirin, which suppresses platelet activation. To explore the possibility of targeting platelet activation (cyclooxygenase-1) and necrosis (cyclophilin D) pathways in combination, the effect of ex vivo cyclosporine A treatment on thrombin and collagen activation of platelets from healthy volunteers before and after 7 days of aspirin ingestion was compared. Aspirin ingestion resulted in no change in the GSAO+/P-selectin+ necrotic (FIG. 8A) or procoagulant (FIG. 8B) potential of activated platelets. However, cyclosporine A treatment of pre-aspirin platelets resulted in significant decrease in GSAO+/P-selectin+ necrotic platelets and corresponding procoagulant function, and this effect was significantly more pronounced in the post-aspirin platelets. These results indicate that targeting of platelet activation by aspirin alone does not affect formation of procoagulant platelets, but aspirin treatment sensitizes platelets to cyclophilin D blockade, thereby increasing the degree to which thrombin production can be inhibited.

Example 10

Platelet Mitochondrial Membrane Potential

Mitochondrial membrane potential was measured using the JC-1 cationic dye (5,5',6,6'-tetrachloro-1,1',3,3'-tetraethyl-imidacarbocyanine iodide, Sigma) (Life Technologies). Washed platelets were incubated with JC-1 (2 μM) for 30 min in the dark at 37° C., washed once and analyzed immediately on a BDFACS Canto II. On some occasions, washed platelets were incubated with the mitochondrial membrane disrupter 2-[2-(3-chlorophenyl)hydrazinylyidene]propanedinitrile (CCCP, 4 μM) for 10 min.

Example 11

Platelet Surface FXa

Platelet surface FXa was measured using FITC-labeled Glu-Gly-Arg chloromethyl ketone (FITC-GGACK, Haematologic Technologies). Platelet rich plasma was diluted 1:5 with modified Hepes/Tyrodes buffer supplemented with fibrin polymerisation inhibitor Gly-Pro-Arg-Pro (2.5 mM, Sigma) and $CaCl_2$ (4 mM), stimulated with thrombin and collagen as above, labeled with FITC-GGACK (6.5 μM) for 15 min then co-labeled with GSAO-AF647 or GSCA-AF647 (1 μIV). The labeled platelets were fixed (Pamfix, Platelet Solutions), washed and analyzed by flow cytometry on a BD Fortessa LSR.

Example 12

Platelet Procoagulant Potential

Thrombin generation capacity of agonist stimulated platelets was measured using the Calibrated Automated Thrombogram as described (Hemker et al., 2003) using the Fluorskan Ascent (Thermo Scientific). Agonist stimulated platelets were washed in phosphate-buffered saline and resuspended into the donor's own platelet poor plasma at $5\times10^4$/μL and recombinant tissue factor (0.3 μM, Innovin, Dade Behring) was added. Assays were performed in triplicate.

Example 13

Imaging and Analysis of Murine Thrombi

This study was approved by the University of New South Wales Animal Care & Ethics Committee (ACEC 13/47A). C57BL/6J mice were obtained from The Jackson Laboratory. Cyclophilin D megakaryocyte-specific knockout mice were provided by Benjamin Kile (Walter & Eliza Hall Institute). The Cyclophilin D conditional knockout allele (Ppif$^{tm1Mmos}$/J) has been previously described (Schinzel et al., 2005). Originally constructed in 129X1/SvJ-derived RW4 embryonic stem cells, mice carrying the Ppif$^{tm1Mmos}$/J a mutation had been backcrossed several generations to C57BL/6 prior to being crossed with the Pf4-Cre transgenic strain (Tiedt et al., 2007). The latter was generated in, and maintained on, the C57BL/6 background.

Intravital video microscopy of the cremaster muscle microcirculation was performed using a VIVO Intravital Imaging System (Intelligent Imaging Innovations) consisting of an upright Zeiss Axio Examiner fitted with a motorised stage, piezo controlled z focus and 63x/1.0NA water immersion Plan Apo Objective (Zeiss). Imaging was though spinning disc confocal (Yokogawa, CSUX1-M1L-E) and digital images were captured with a Hamamatsu 9300 CCD camera connected to a VS4-1845 Image Intensifier GEN III (Video Scope International). Platelet marker Dylight 649-conjugated anti-CD42b antibody (0.1 µg/g mouse, Emfret Analytics), GSAO-Oregon Green or GSAO-AF546 (0.1 µg/g mouse) and rhodamine-2 (2 µg/g mouse, Life Technologies) or AF488-conjugated anti-fibrin antibody (0.5 µg/g mouse, clone 59D8 kindly supplied by Bruce and Barbara Furie, Beth Israel Deaconess Medical Centre, Harvard Medical School, MA), were injected into the murine circulation in different combinations. The animal was kept at 37° C. using a warming blanket; muscle was continuously bathed with a bicarbonate buffered physiological solution heated to 37° C. which also served as the imaging medium. Data was captured digitally from 3 fluorescence channels, using 488 nm, 561 nm and 640 nm laser stack excitation. The microscope system was controlled and images were analyzed using Slidebook 5.5 (Intelligent Imaging Innovations).

Thrombi were triggered in cremaster muscle arterioles using two modes of injury. A cremaster arteriolar (30- to 60-µm diameter) vessel wall was injured with a Vector galvanometer-based point 532 nm pulsed laser (Intelligent Imaging Innovations). Laser was focused through the microscope objective, parfocal with the focal plane. 4D data acquisition was initiated both prior to and after a single laser pulse for each injury. In separate experiments, filter paper saturated with 8% $FeCl_3$ was applied to the mouse cremaster muscle for 3 min. The paper was removed and the tissue was washed using bicarbonate-buffered saline solution. 3D data acquisition was initiated prior to and after filter paper application. Z Stacks of XY planes (0.55 µm intervals) were imaged using a spinning-disk confocal scanner (Yokogawa CSU X1) using a pizeo focus drive. To quantitate signal in each thrombus, a threshhold value for each fluorescence channel was calculated independently within a non-thrombus involved portion of the vessel. A segment mask was created above threshold for each channel in each z plane and the cumulative integrated fluorescence calculated for each thrombus. Background value was multiplied by volume in voxels, background subtracted and the net integrated fluorescence calculated for each channel in each thrombus. 3D models of platelet aggregates and cross-sectional orthogonal views were rendered within Intelligent Imaging Innovation software.

Example 14

Aspirin Study Participants and Protocol

This study was approved by the University of New South Wales Human Research Ethics Advisory Committee (HC132219), conducted according to the Declaration of Helsinki and all volunteers gave written informed consent. Five healthy volunteers aged 25-45 years were recruited. Prior to starting the study, all volunteers abstained from aspirin or non-steroidal anti-inflammatory drugs (NSAIDS), or other anti-platelet therapies for 14 days. Volunteers received 100 mg enteric coated aspirin daily for 7 days. Blood was collected and washed platelets assessed at baseline, day 0, and again at day 7 of treatment.

Example 15

Statistical Analysis

Parametric paired t test was used to evaluate differences between different agonist stimulated groups and the effect of aspirin, cyclophilin D inhibition and pancaspase inhibition on stimulated platelets. Statistical significance was defined as p values of less than 0.05. Sensitivity and specificity were calculated using a 2×2 table and correlation measured by Pearson's Chi-squared analysis. Colocalization of signals in 3D confocal microscopy imaging of thrombi was determined using the Mander's overlap coefficient with a threshold set to the estimated background value (Image J JaCOP plugin software) (Bolte and Cordelieres, 2006).

Example 16

Whole Blood Assay for Necrotic Platelet Potential

Experiments using genetically modified mice indicate that formation of procoagulant platelets is dependent on the cyclophilin D necrosis pathway, but independent of the $Bcl_{XL}$ apoptosis pathway. In healthy volunteers, the strong platelet agonists, thrombin and collagen, induce formation of procoagulant platelets via a mechanism that is largely independent of protease activated receptors. Patients with coronary artery disease have a heightened procoagulant platelet potential and are sensitised to thrombin and ADP stimulation. The procoagulant platelet potential in these patients is insensitive to aspirin, which targets platelet aggregation, but modified by P2Y12 antagonists.

Blood from healthy human volunteers was drawn from an antecubital fossa vein using a 21-gauge needle into evacuated sterile collection tubes containing 0.109 M sodium citrate. Following no or minimal tourniquet application, the initial 2 mL of blood was discarded to avoid pre-analytical activation of platelets. The tube was gently mixed by inversion six times. Murine blood samples were collected by cardiac puncture under isoflurane anesthesia. Following midline abdominal and bilateral subcostal surgical incisions to expose the heart, blood was drawn from the left ventricle through a 25G needle into a 1 mL syringe containing sodium citrate (0.109 M) resulting in a blood to citrate ratio of 9:1. The needle was removed and the blood was gently expelled from the syringe into a sterile microcentrifuge tube and mixed gently by pipetting up and down 5 times.

Following collection, tubes were kept upright at room temperature and blood was assayed within 15 min of collection. Incubation and staining steps were performed in a sterile 96-well polypropylene plate. Citrated whole blood (15 µL) was diluted with Hepes buffered saline, pH 7.35 (30 µL) containing a final concentration of fibrin polymerization inhibitor GPRP (2.5 mM) and $CaCl_2$ (2.5 mM). Agonist(s) were added in 5 µL volume to a final volume of 50 µL, incubated for 10 min at room temperature, and the reaction quenched by diluting with Hepes buffered saline to a final volume of 150 µL. Aliquots (20 µL) of diluted stimulated whole blood were labelled for 15 min at room temperature with GSAO-AF647 (2 µM), CD62P-PE, CD45-BUV395 and CD41a-BV510 in 100 µL final volume. GSCA-AF647 (2 µM) and mouse $lgG_1$ κ isotype control PE served as controls for GSAO and anti-CD62P antibody, respectively. Cells were then fixed with two volumes of PamFix for 5 min. Fixed stained cells were transferred to 5 mL FACS tubes and washed once with ten volumes of Hepes buffered saline containing 0.35% human serum albumin. Cells were pelleted (1,500 g for 8 min) and resuspended in the same buffer.

Figure 12:
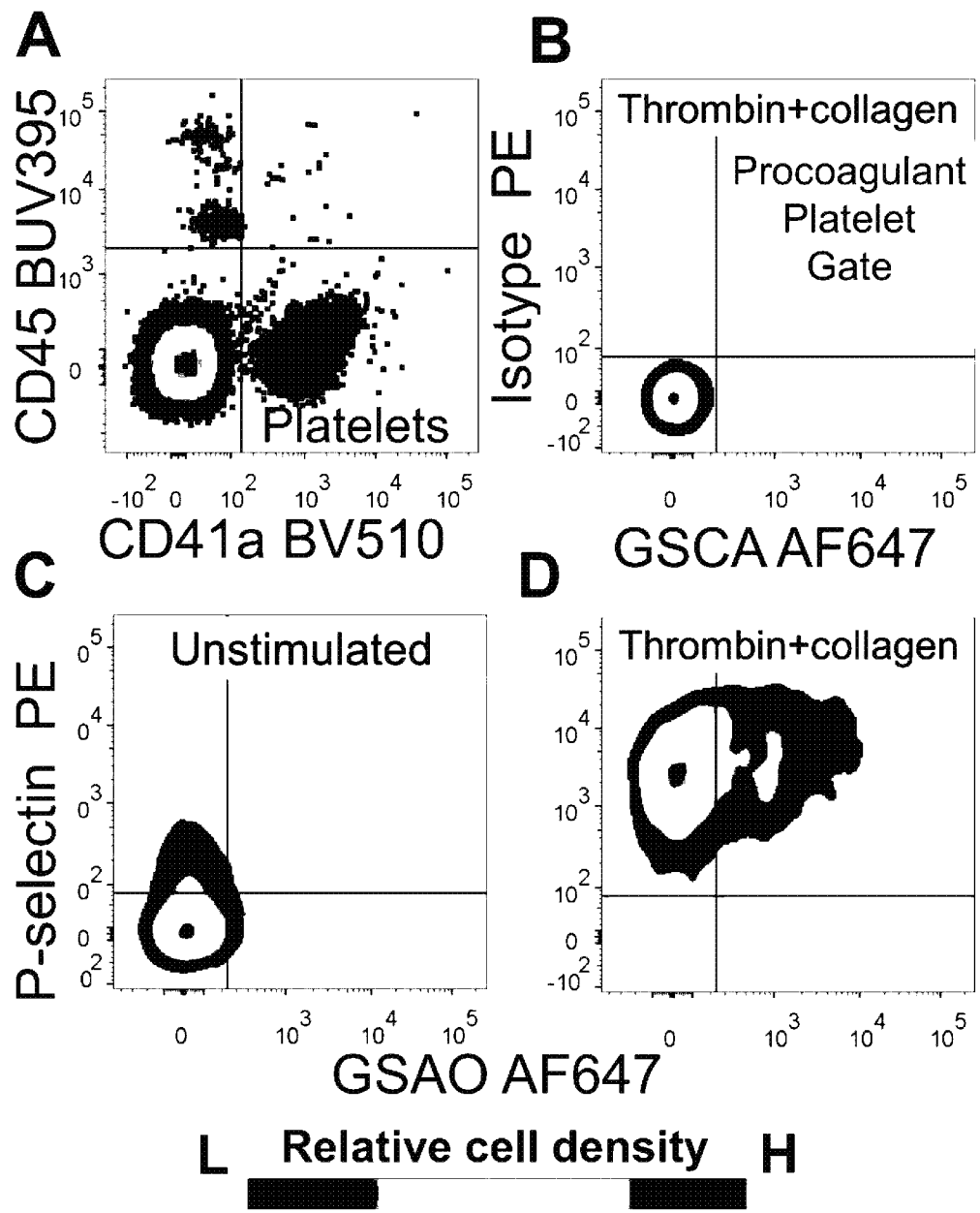
FIG. 12. Gating strategy for detection of procoagulant platelets in human whole blood. A. Platelets were identified as CD41a positive and CD45 negative events. B. Threshold values for P-selectin and GSAO fluorescence were set using agonist stimulated sample stained with control IgG isotype and GSCA respectively. C. At rest, very few platelets show the procoagulant phenotype (P-selectin+/GSAO+). D. Following stimulation with thrombin and collagen a significant proportion of platelets exhibited procoagulant phenotype.

Fixed cells were analyzed by flow cytometry 1 to 3 h after fixation at an average event rate of 2000 events per sec in an LSRFortessa flow cytometer, equipped with either four (405 nm, 488 nm, 561 nm and 640 nm) or five (395 nm) lasers (BD Biosciences). Using the lowest forward scatter threshold of 200, 5,000-10,000 events in the platelet gate (defined as CD41a positive but CD45 negative population) were acquired. Flow cytometry data were exported in the FSC 3.0 format and analysis was performed using FlowJo vX 10.0.7r2 (Tree Star). The gating strategy and analysis is described in detail in FIG. 12.

Example 16

Assay for Procoagulant Platelet Potential in Human Blood

Figure 13:
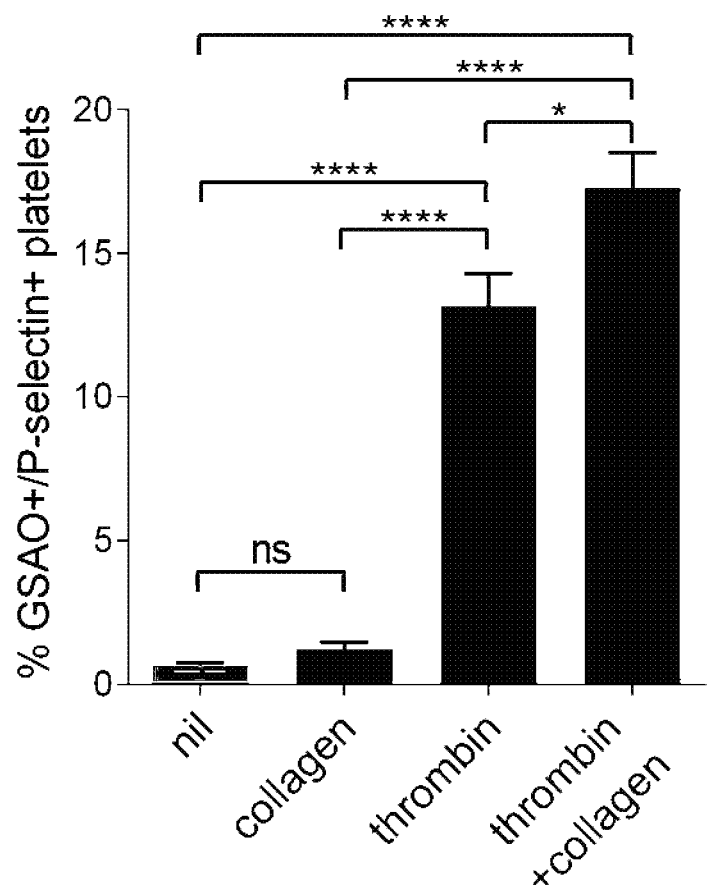
FIG. 13. Assay for procoagulant platelet potential in human blood. A. Thrombin was the most potent inducer of procoagulant platelets. Exposure to thrombin at 2 U/mL resulted in significant proportion of procoagulant platelets (13.2±1.1%), whereas collagen at 10 µg/mL was significantly less potent (1.2±0.2%). The maximal response (17.3±1.3%) was observed after stimulation with combination of thrombin and collagen. Results are mean±SEM from 16-35 donors. One-way ANOVA, α=0.05%, Holm-Sidak multiple comparisons correction. *, p<0.05; ****, p<0.0001.

Thrombin is the most potent inducer of procoagulant platelets in human blood (FIG. 13). Treatment with thrombin resulted in significantly more GSAO+/P-selectin+ platelets than treatment with collagen. The maximal response was observed after stimulation with combination of thrombin and collagen.

Example 17

Assay for Procoagulant Platelet Potential in Mouse Blood

Figure 14:
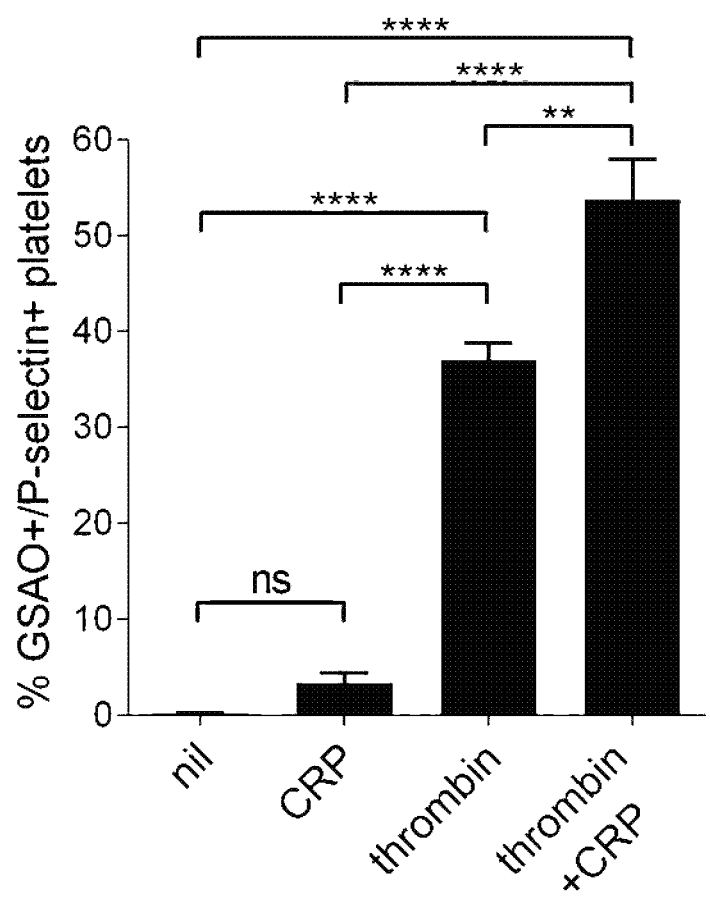
FIG. 14. Assay for procoagulant platelet potential in mouse blood. Thrombin at 2 U/mL is the most potent inducer of murine procoagulant platelets. Collagen related peptide (CRP) at 500 ng/mL is significantly less potent than thrombin but synergizes with thrombin. Bars and errors are mean±SEM of n=3 C57B16 bloods. One-way ANOVA. , p<0.01; **, p<0.0001.

Thrombin is also the most potent inducer of procoagulant platelets in murine blood (FIG. 14). Collagen related peptide is significantly less potent than thrombin but it synergizes with thrombin.

Example 18

Figure 15:
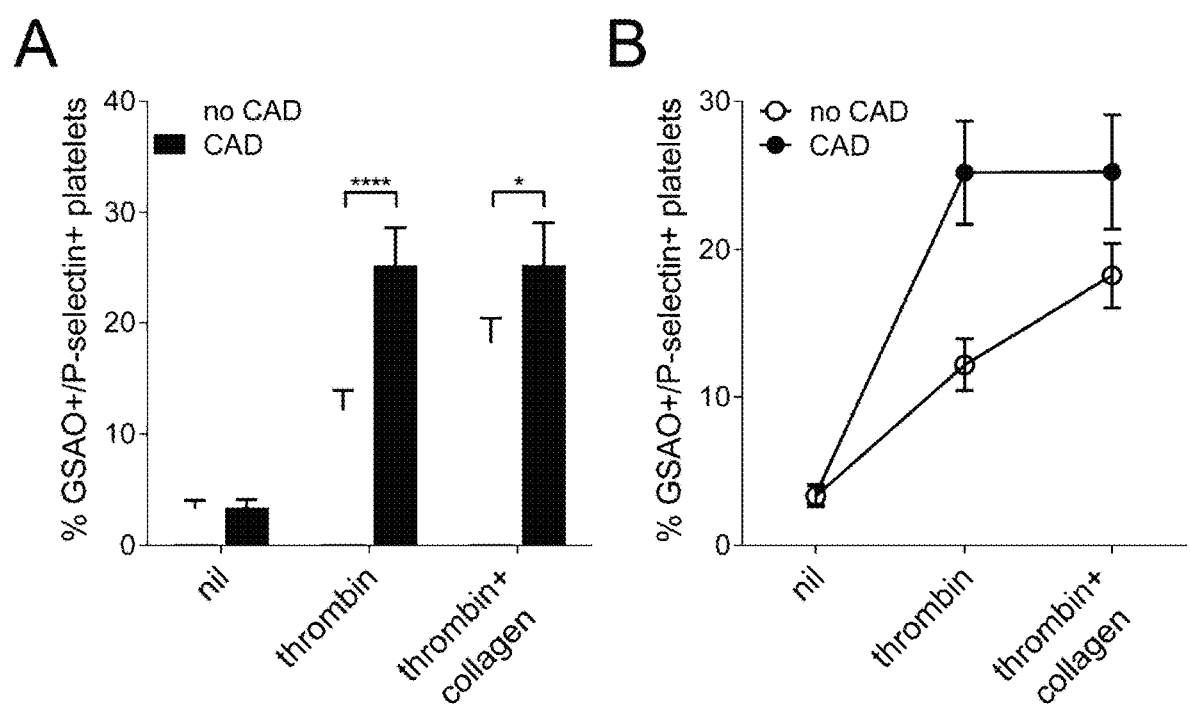
FIG. 15. Coronary artery disease (CAD) is associated with a heightened procoagulant platelet potential. Heparinfree initial peripheral artery sample from patients with no history of treatment with P2Y12 inhibitors were used in this analysis. A. Platelets from patients with CAD showed increased stimulus-induced procoagulant platelet potential compared to those without CAD. Two-way ANOVA analysis with Tukey correction for multiple comparisons, two-tailed tests with a significance level of 5% were used. Bars and errors are mean±SEM of n=11 with no CAD and n=16 with CAD. *, p<0.05; ****, p<0.0001. B. In contrast to patients with no CAD, platelets from CAD patients did not require additional stimulation with collagen to reach the maximal procoagulant potential and were sensitized to thrombin.
Figure 16:
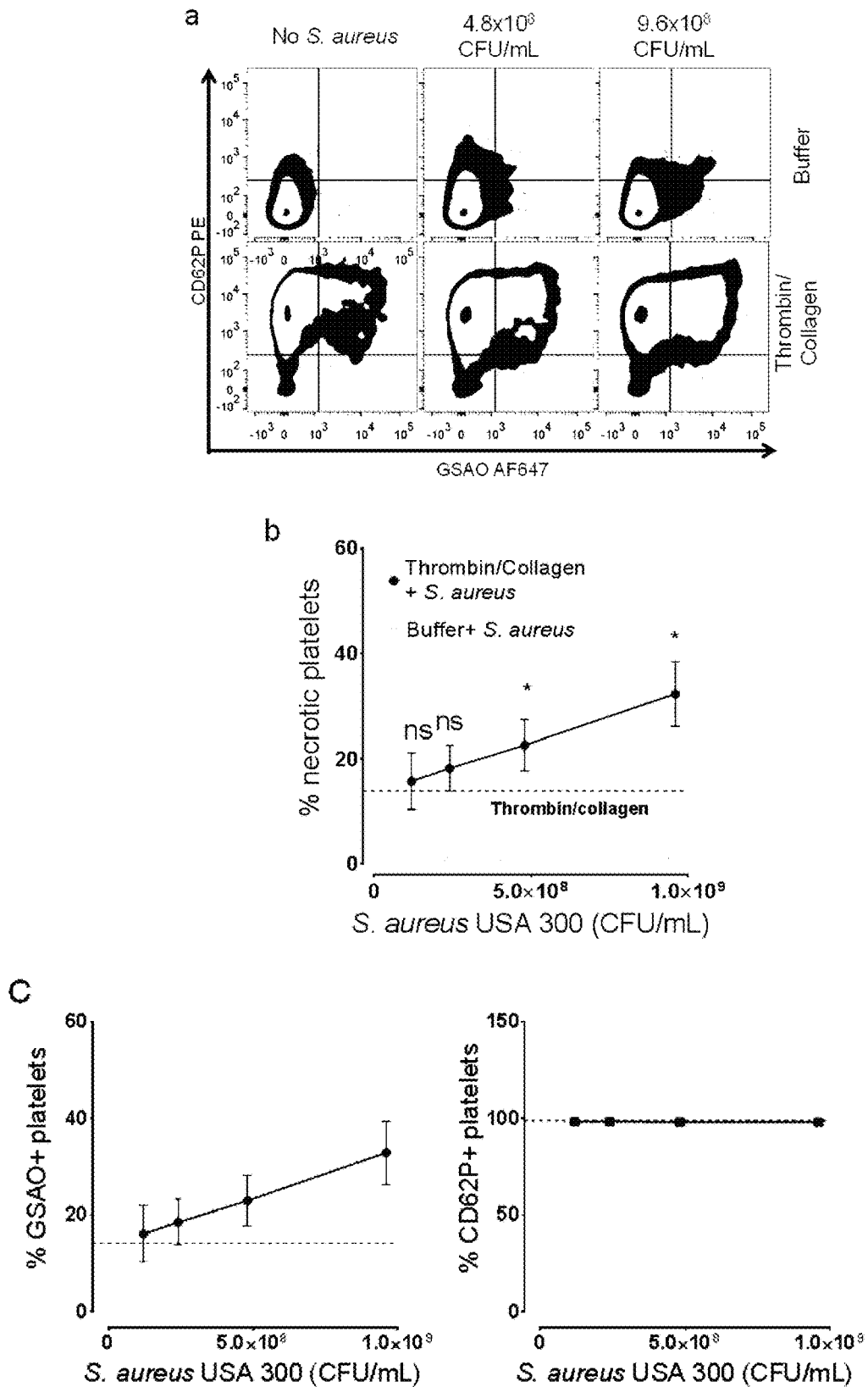
FIG. 16. *S. aureus* USA 300 potentiates generation of necrotic platelets in response to dual stimulation with thrombin and collagen. A. Effect of *S. aureus* on the size of necrotic platelet population on its own (upper panel) and in the presence of both thrombin (2 U/mL) and collagen (10 µg/mL) (lower panel). A representative example, n=3. B. Dual agonist induced platelet necrosis is amplified in a dose dependent manner by *S. aureus*. Results are shown as mean±SEM, n=3. One-tailed, paired t-test. C. Compared to stimulation with thrombin and collagen, bacteria induced further increase in GSAO-AF647 uptake by platelets (left panel), whilst the baseline CD62P expression (right panel), already near maximum, showed very little change.

Coronary Artery Disease is Associated with a Heightened Procoagulant Platelet Potential To examine the effect of CAD on procoagulant platelet potential, non-heparinized bloods from patients with exposure to either aspirin only or no antiplatelet medications within 7 days of the procedure were assayed. Compared to patients with no CAD, patients with CAD showed a heightened platelet procoagulant potential in response to thrombin or thrombin plus collagen (FIG. 15A). In contrast to patients with no CAD, platelets from CAD patients did not require additional stimulation with collagen to reach the maximal procoagulant potential and were sensitized to thrombin (FIG. 15B). There were no statistically significant differences between the groups in the absence of agonist stimulation.

REFERENCES

Prodan, C. I., Stoner, J. A., Cowan, L. D. & Dale, G. L. (2013) Higher coated-platelet levels are associated with stroke recurrence following nonlacunar brain infarction. *J. Cereb. Blood Flow Metab.* 33, 287-292.

Kirkpatrick, A. C., Tafur, A. J., Vincent, A. S., Dale, G. L., and Prodan, C. I. (2014) Coated-platelets improve prediction of stroke and transient ischaemic attack in asymptomatic internal carotid artery stenosis. *Stroke* 45, 2995-3001.

Grundler, K., Angstwurm, M., Hilge, R., Baumann, P., Annecke, T., Crispin, A., Sohn, H.-Y., Massberg, S., and Kraemer, B. (2014) Platelet mitochondrial membrane depolarization reflects disease severity in patients with sepsis and correlates with clinical outcome. *Crit Care* 18, R31.

Schoenwaelder, S. M. et al. (2009) Two distinct pathways regulate platelet phosphatidylserine exposure and procoagulant function. *Blood* 114, 663-666.

Jobe, S. M. et al. (2008) Critical role for the mitochondrial permeability transition pore and cyclophilin D in platelet activation and thrombosis. *Blood* 111, 1257-1265.

Bouchard, B. A., Paradis, A. K. & Brummel-Ziedins, K. E. (2011) Measurement of procoagulant platelet subpopulations in whole blood: development of an assay for population-based studies *Thromb. Res.* 127, 62-64.

Heemskerk, J. W., Vuist, W. M., Feijge, M. A., Reutelingsperger, C. P. & Lindhout, T. (1997) Collagen but not fibrinogen surfaces induce bleb formation, exposure of phosphatidylserine, and procoagulant activity of adherent platelets: evidence for regulation by protein tyrosine kinase-dependent Ca2+ responses. *Blood* 90, 2615-2625.

Park, D., Don, A. S., Massamiri, T., Karwa, A., Warner, B., Macdonald, J. Hemenway, C Naik, A., Kuan, K. T., Dilda, P. J., et al. (2011) Noninvasive imaging of cell death using an hsp90 ligand. *J Am Chem Soc.* 133, 2832-2835.

Park, D., Xie, B. W., Van Beek, E. R., Blankevoort, V., Que, 1., Lowik, C. W. G. M., and Hogg, P. J. (2013) Optical Imaging of Treatment-Related Tumor Cell Death Using a Heat Shock Protein-90 Alkylator. *Molecular Pharmaceutics* 10, 3882-3891.

Xie, B. W. et al. (2013) Optical imaging of cell death in traumatic brain injury using a heat shock protein-90 alkylator. *Cell death & disease* 4, e473.

Bevers E. M Comfurius P., van Rijn J. L., Hemker H. C., Zwaal R. F. (1982) Generation of prothrombin-converting activity and the exposure of phosphatidylserine at the outer surface of platelets. *Eur J Biochem.* 122(2), 429-436.

Fager A. M., Wood J. P Bouchard B. A., Feng P., Tracy P. B. (2010) Properties of procoagulant platelets: defining and characterizing the subpopulation binding a functional prothrombinase. *Arterioscler Thromb Vasc Biol.* 30(12), 2400-2407.

Dilda P. J., Decollogne S., Weerakoon L., et al. (2009) Optimization of the antitumor efficacy of a synthetic mitochondrial toxin by increasing the residence time in the cytosol. *J Med Chem.* 52(20), 6209-6216.

Dilda P J, Ramsay E. E., Corti A, Pompella A, Hogg P. J. (2008) Metabolism of the tumor angiogenesis inhibitor 4-(N—(S-Glutathionylacetyl)amino)phenylarsonous acid. *J Biol Chem.* 2008; 283(51):35428-35434.

Hagenbuch B., Meier P. J. (2003) The superfamily of organic anion transporting polypeptides. *Biochim Biophys Acta.* 1609(1), 1-18.

Niessen J., Jedlitschky G., Grube M., et al. (2009) Human platelets express organic anion-transporting peptide 2B1, an uptake transporter for atorvastatin. *Drug Metab Dispos.* 37(5), 1129-1137.

Kobayashi D., Nozawa T., Imai K., Nezu J., Tsuji A., Tamai I. (2003) Involvement of human organic anion transporting polypeptide OATP-B (SLC21A9) in pH-dependent transport across intestinal apical membrane. *J Pharmacol Exp Ther.* 306(2), 703-708.

Nakagawa, T. et al. (2005) Cyclophilin D-dependent mitochondrial permeability transition regulates some necrotic but not apoptotic cell death. *Nature* 434, 652-658.

McCormack, J. G., Halestrap, A. P. & Denton, R. M. (1990) Role of calcium ions in regulation of mammalian intramitochondrial metabolism. *Physiol. Rev.* 70, 391-425.

Falati S., Gross P., Merrill-Skoloff G., Furie B. C., Furie B. (2002) Real-time in vivo imaging of platelets, tissue factor and fibrin during arterial thrombus formation in the mouse. *Nat Med.* 8(10), 1175-1181.

Dubois C, Panicot-Dubois L, Gainor J F, Furie B C, Furie B. (2007) Thrombin-initiated platelet activation in vivo is vWF independent during thrombus formation in a laser injury model. *J Clin Invest.* 2007; 117(4):953-960.

Dubois C., Panicot-Dubois L., Merrill-Skoloff G., Furie B., Furie B. C. (2006) Glycoprotein VI-dependent and -independent pathways of thrombus formation in vivo. *Blood.* 107(10), 3902-3906.

Voronov R. S., Stalker T. J Brass L. F., Diamond S. L. (2013) Simulation of intrathrombus fluid and solute transport using in vivo clot structures with single platelet resolution. *Ann Biomed Eng.* 41(6), 1297-1307.

Stalker T. J., Traxler E. A., Wu J., et al. (2013) Hierarchical organization in the hemostatic response and its relationship to the platelet-signaling network. *Blood.* 121(10), 1875-1885.

Dale G. L., Friese P., Batar P., et al. (2002) Stimulated platelets use serotonin to enhance their retention of procoagulant proteins on the cell surface. *Nature.* 415 (6868), 175-179.

Abaeva A. A., Canault M., Kotova Y. N., et al. (2013) Procoagulant platelets form an alpha-granule protein-covered "cap" on their surface that promotes their attachment to aggregates. *J Biol Chem.* 288(41), 29621-29632.

Bratosin D., Mitrofan L., Palii C., Estaquier J., Montreuil J. (2005) Novel fluorescence assay using calcein-AM for the determination of human erythrocyte viability and aging. *Cytometry A.* 66(1), 78-84.

Hemker H. C., Giesen P., Al Dieri R., et al. (2003) Calibrated automated thrombin generation measurement in clotting plasma. *Pathophysiol Haemost Thromb.* 33(1), 4-15.

Schinzel A. C., Takeuchi O., Huang Z., et al. (2005) Cyclophilin D is a component of mitochondrial permeability transition and mediates neuronal cell death after focal cerebral ischemia. *Proc Natl Acad Sci USA.* 102(34), 12005-12010.

Tiedt R., Schomber T., Hao-Shen H/, Skoda R. C. (2007) Pf4-Cre transgenic mice allow the generation of lineage-restricted gene knockouts for studying megakaryocyte and platelet function in vivo. *Blood.* 109(4), 1503-1506.

Bolte S., Cordelieres F. P. (2006) A guided tour into subcellular colocalization analysis in light microscopy. *J Microsc.* 224(Pt 3), 213-232.

The invention claimed is:

1. A process for identifying and determining the proportion of procoagulant and apoptotic platelets in a platelet-containing whole blood sample, wherein platelets in the whole blood sample have not been isolated or enriched, the process comprising:

contacting a platelet with an agonist comprising thrombin; contacting the platelet with a compound of the structural formula

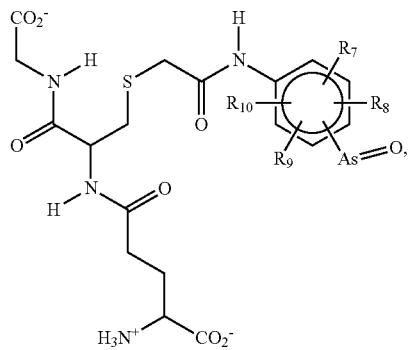

wherein $R_7$ to $R_{10}$ are independently selected from the group consisting of hydrogen, $C_1$-$C_5$ alkyl, $C_6$-$C_{12}$ aryl, halogen, hydroxy, amino, nitro, carboxy, $C_1$-$C_5$ alkoxy, —OS(O)$_2$R$_3$ and —NHC(O)CH$_2$Q wherein Q is halogen, —OS(O)$_2$CH$_3$, —OS(O)$_2$C$_6$H$_5$ and —OS(O)$_2$-p tolyl; and wherein, when any one of $R_7$ to $R_{10}$ is $C_1$-$C_5$ alkyl, $C_6$-$C_{12}$ aryl, $C_1$-$C_5$ alkoxy, —OS(O)$_2$R$_3$ it is capable of forming a fused ring with the phenylene; and further wherein, at least one of $R_7$ to $R_{10}$ is $C_1$-$C_5$ alkyl, $C_6$-$C_{12}$ aryl, $C_1$-$C_5$ alkoxy, or —OS(O)$_2$R$_3$, in combination with at least any one other of $R_7$ to $R_{10}$, is capable of forming a fused ring with the phenylene, determining whether the platelet is labelled by the compound, and determining whether the platelet is positive or negative for P-selectin expression, wherein a platelet which is labelled by the compound and is positive for P-selectin expression is identified as a procoagulant platelet, and a platelet which binds to the compound and is negative for P-selectin expression is identified as an apoptotic platelet, further comprising determining the proportion of procoagulant or apoptotic platelets in the sample.

2. The process of claim 1, wherein said platelet-containing sample is derived from a patient.

3. The process of claim 1, wherein $R_7$ to $R_{10}$ are independently selected from the group consisting of hydrogen, halogen, hydroxy, amino, nitro, cyano, carboxy, $C_1$-$C_5$ alkoxy, methyl, ethyl, isopropyl, tert-butyl, phenyl and —NHC(O)CH$_2$Q wherein Q is halogen, —OS(O)$_2$CH$_3$, —OS(O)$_2$C$_6$H$_5$ or —OS(O)$_2$-p tolyl; and wherein the arsenoxide (—As=O) group is at the 4-position of the phenylene ring.

4. The process of claim 1 wherein the compound is represented by Formula (VI):

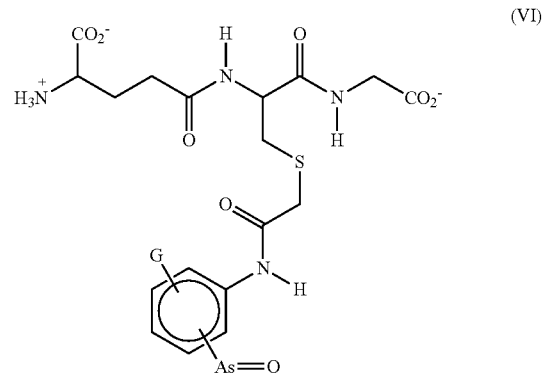

wherein G is selected from the group consisting of: hydrogen, halogen, hydroxy, amino, nitro, carboxy, $C_1$-$C_5$ alkoxy, $C_1$-$C_5$ alkyl and $C_6$-$C_{12}$ aryl and —NHC(O)CH$_2$Q wherein Q is halogen, —OS(O)$_2$CH$_3$, —OS(O)$_2$C$_6$H$_5$ or —OS(O)$_2$-p tolyl.

5. The process of claim 4, wherein G is selected from the group consisting of: hydrogen, halogen, hydroxy, amino, nitro, carboxy, $C_1$-$C_5$ alkoxy, methyl, ethyl, iso-propyl, tert-butyl, phenyl, and —NHC(O)CH$_2$Q wherein Q is halogen, —OS(O)$_2$CH$_3$, —OS(O)$_2$C$_6$H$_5$ or —OS(O)$_2$-p tolyl.

6. The process according to claim 1, wherein the compound is GSAO:

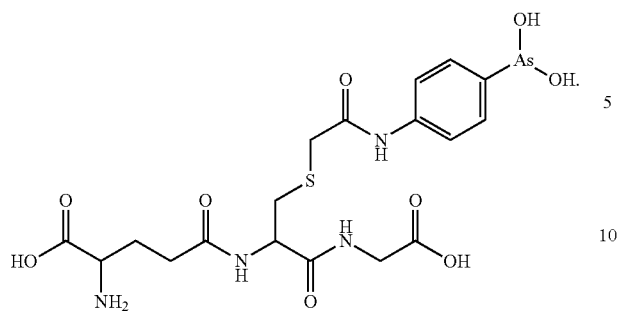
7. The process according to claim 1, wherein the volume of the platelet-containing whole blood sample is less than about 100 μL.